United States Patent
Foster et al.

(10) Patent No.: US 10,251,543 B2
(45) Date of Patent: Apr. 9, 2019

(54) OPTOMETRY APPARATUS AND METHOD FOR SUBJECTIVE MEASUREMENT USING OPTOMETRIC CHART

(71) Applicant: Kabushiki Kaisha TOPCON, Tokyo (JP)

(72) Inventors: Robert Foster, Oakland, NJ (US); Mutsutaka Ishihara, Tokyo (JP); Wataru Umeji, Tokyo (JP)

(73) Assignee: Kabushiki Kaisha TOPCON, Tokyo (JP)

( * ) Notice: Subject to any disclaimer, the term of this patent is extended or adjusted under 35 U.S.C. 154(b) by 70 days.

(21) Appl. No.: 14/694,188

(22) Filed: Apr. 23, 2015

(65) Prior Publication Data
US 2015/0342454 A1  Dec. 3, 2015

Related U.S. Application Data

(60) Provisional application No. 62/003,772, filed on May 28, 2014.

(51) Int. Cl.
| | |
|---|---|
| *A61B 3/032* | (2006.01) |
| *A61B 3/18* | (2006.01) |
| *A61B 3/103* | (2006.01) |

(52) U.S. Cl.
CPC .............. *A61B 3/032* (2013.01); *A61B 3/103* (2013.01)

(58) Field of Classification Search
CPC .......... A61B 3/032; A61B 3/036; A61B 3/103
See application file for complete search history.

(56) References Cited

U.S. PATENT DOCUMENTS

| | | | |
|---|---|---|---|
| 4,465,348 A | 8/1984 | Lang et al. | |
| 6,135,596 A * | 10/2000 | Yoshida | A61B 3/152 351/200 |
| 2002/0042580 A1 | 4/2002 | Alster et al. | |
| 2003/0081176 A1* | 5/2003 | Stewart | A61B 3/024 351/223 |

(Continued)

FOREIGN PATENT DOCUMENTS

| | | |
|---|---|---|
| JP | 2000-126128 A | 5/2000 |
| JP | 2003265412 A | 9/2003 |
| JP | 2004-097377 A | 4/2004 |

(Continued)

OTHER PUBLICATIONS

Extended European Search Report for EP Application No. 15169025.2 dated Oct. 6, 2015.

(Continued)

*Primary Examiner* — William R Alexander
*Assistant Examiner* — Ephrem Z Mebrahtu
(74) *Attorney, Agent, or Firm* — Pearne & Gordon LLP

(57) ABSTRACT

An optometry apparatus includes an eye chart presentation optical system that presents an optometric chart to an eye to be examined as a subjective eye chart for subjective measurement and a control unit that controls the eye chart presentation optical system to present the optometric chart. The control unit executes an instant presentation of the optometric chart by controlling the eye chart presentation optical system to finish presenting the optometric chart when an instant presentation time has elapsed after starting presenting the optometric chart.

13 Claims, 21 Drawing Sheets

(56) References Cited

U.S. PATENT DOCUMENTS

| | | | |
|---|---|---|---|
| 2004/0046934 A1* | 3/2004 | Sponsel | A61B 3/032 351/200 |
| 2004/0075814 A1 | 4/2004 | Alster et al. | |
| 2005/0018132 A1* | 1/2005 | Fukuma | A61B 3/0075 351/200 |
| 2008/0018858 A1 | 1/2008 | Kanazawa et al. | |
| 2008/0309879 A1* | 12/2008 | Hirji | A61B 3/032 351/223 |
| 2012/0162606 A1* | 6/2012 | Nakamura | A61B 3/032 351/221 |
| 2012/0212706 A1* | 8/2012 | Chou | A61B 3/0033 351/223 |
| 2013/0194317 A1* | 8/2013 | Guillon | A61B 3/022 345/690 |
| 2015/0201832 A1 | 7/2015 | Palanker | |
| 2016/0374551 A1 | 12/2016 | Palanker | |

FOREIGN PATENT DOCUMENTS

| | | |
|---|---|---|
| JP | 2004-510478 A | 4/2004 |
| JP | 2006-246992 A | 9/2006 |
| JP | 2013-526920 A | 6/2013 |
| WO | 2014022850 A1 | 2/2014 |

OTHER PUBLICATIONS

Japanese Office Action for Japanese Patent Application No. 2015-029519 dated Oct. 9, 2018.
Japanese Office Action for Japanese Patent Application No. 2015-029519 dated Jan. 29, 2019.

* cited by examiner

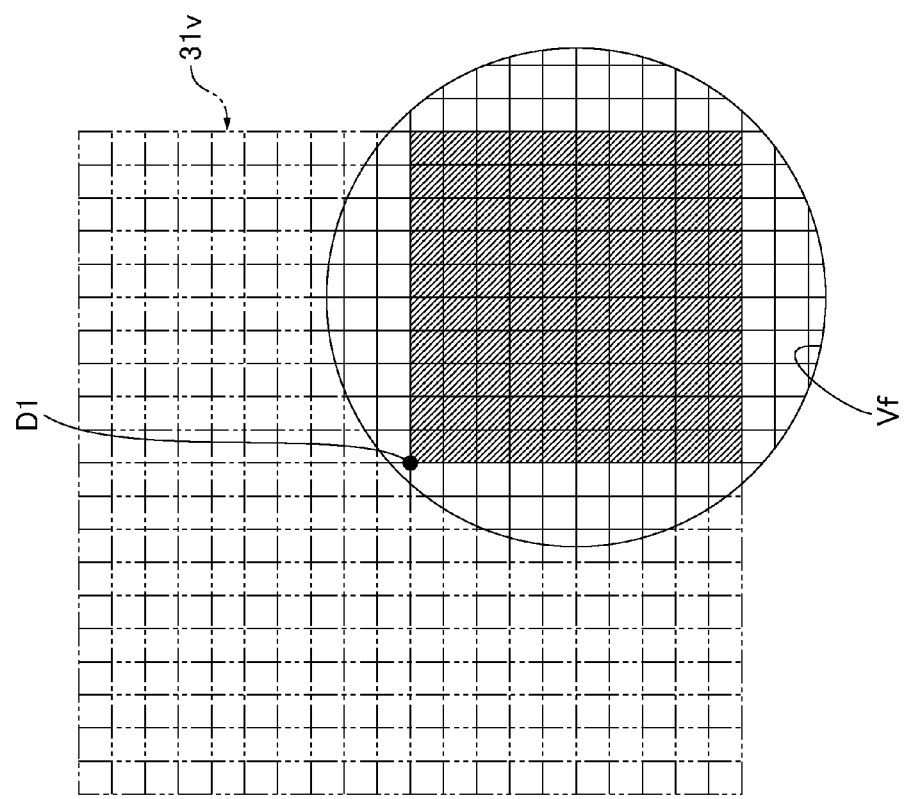
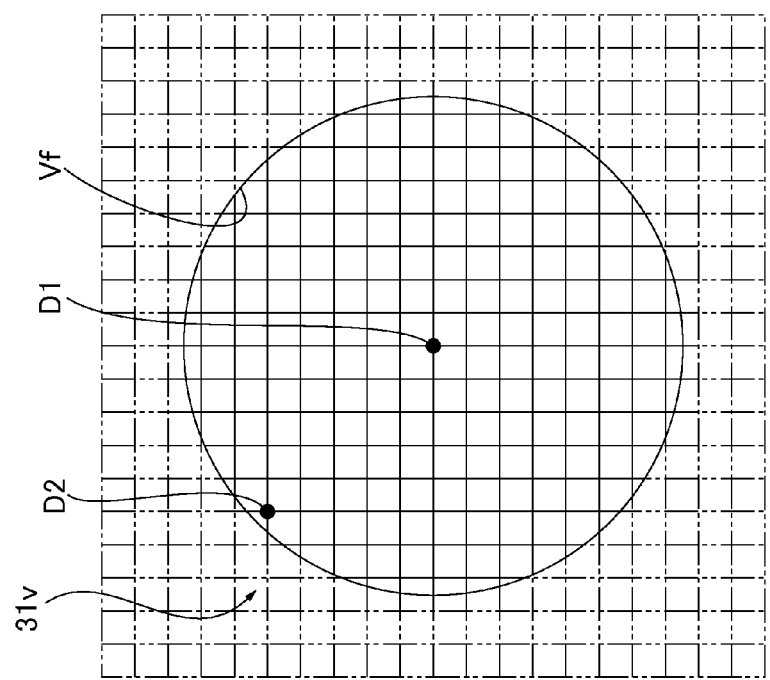

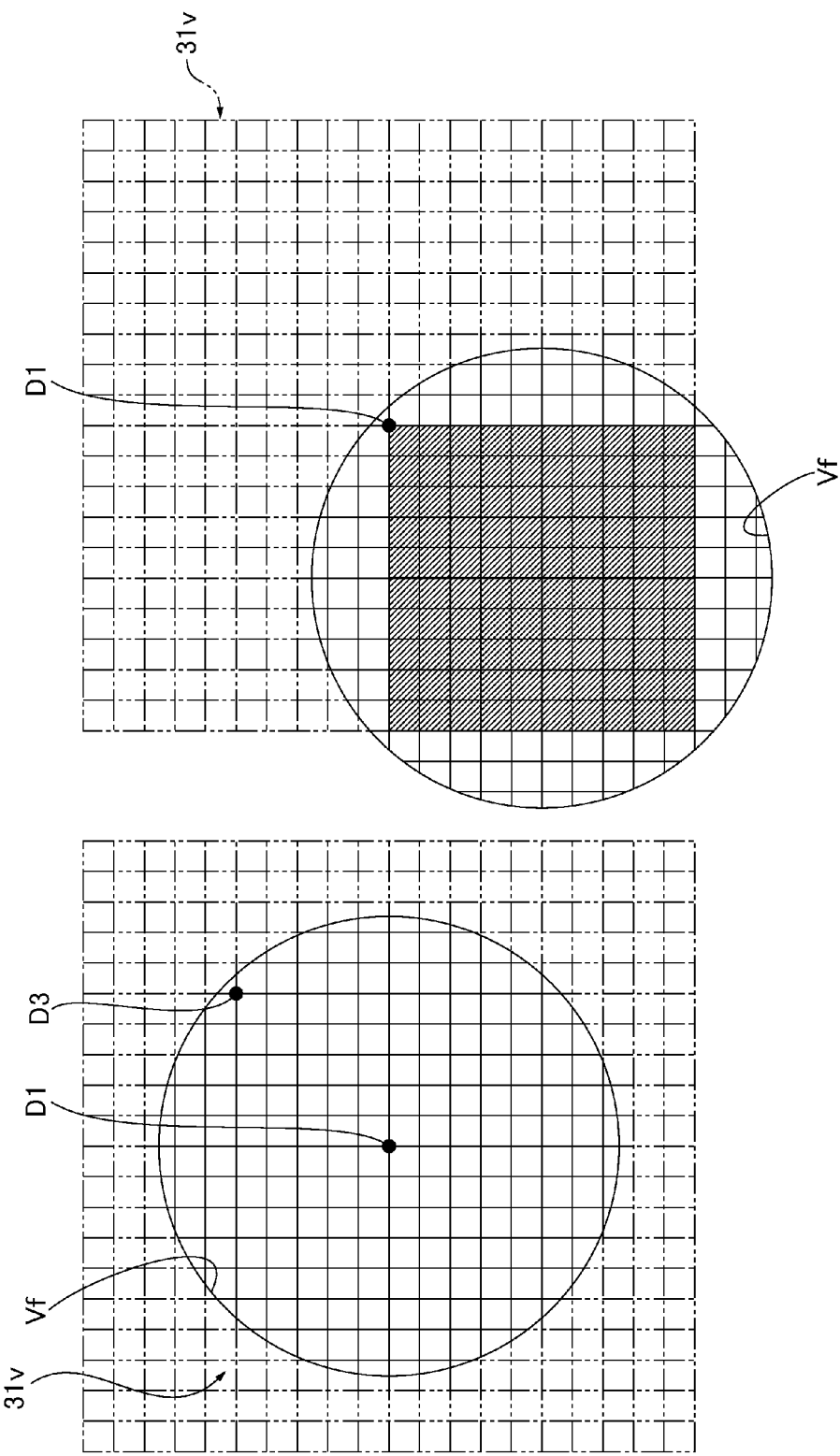

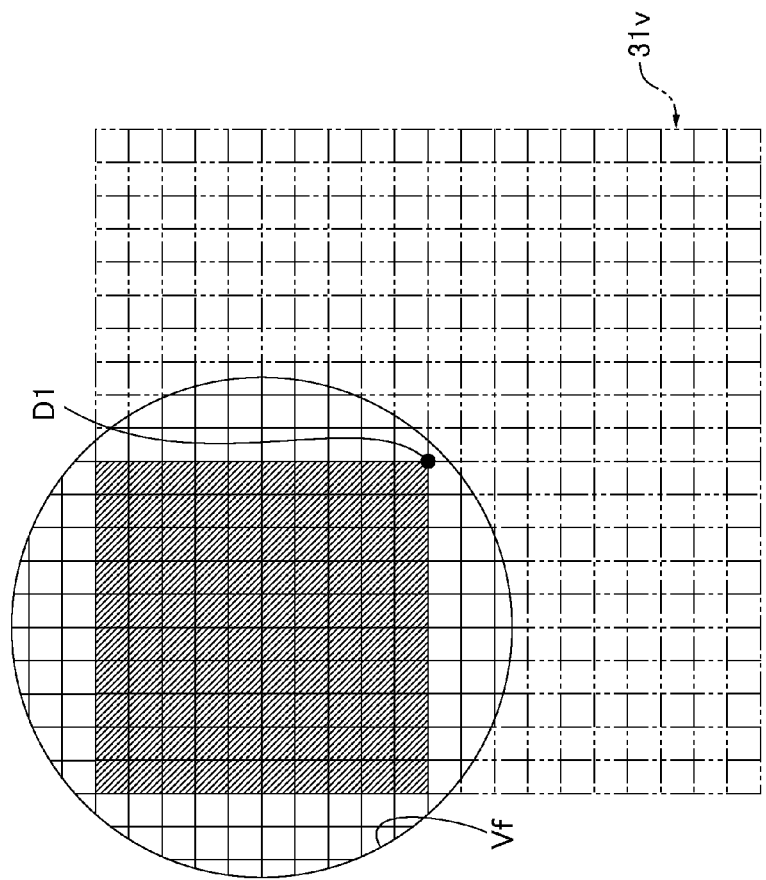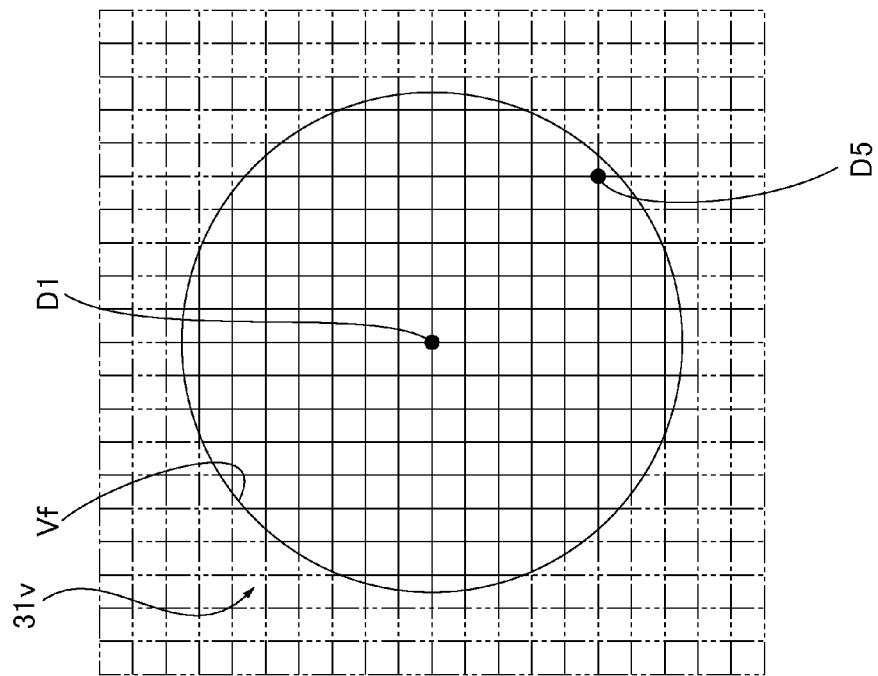

OPTOMETRY APPARATUS AND METHOD FOR SUBJECTIVE MEASUREMENT USING OPTOMETRIC CHART

CROSS-REFERENCE TO RELATED APPLICATIONS

The present application is based on and claims priority to provisional patent application No. 62/003,772, filed May 28, 2014, the disclosure of which is hereby incorporated by reference herein in its entirety.

BACKGROUND

Technical Field

The present invention relates to an optometry apparatus and a method for subjective measurement, particularly to an optometry apparatus to conduct subjective measurement using an optometric chart and a method for subjective measurement using the same.

Description of Related Art

An optometry apparatus to conduct ophthalmological examination or ocular refractive power examination for measuring optical characteristics of an eye to be examined has conventionally been known. As is taught by, for example, Japanese Laid-Open Patent Applications No. 2003-265412 (Document 1), the ophthalmological examination is a so-called subjective measurement (subjective diagnosis), i.e., measurement conducted based on responses or reactions of a subject (patient) against optometric charts.

SUMMARY

As is known, an eye forms an image by imaging incident light on its retina, and a person recognizes the formed image. However, the person usually does not recognize the image as formed on the retina but recognizes the image that has been slightly and appropriately corrected in his/her brain. Hence, the subject (patient) may give responses to the examiner in accordance with the corrected image (i.e., not an image as formed on the retina in accordance with the incident light) when conducting subjective measurement by having the subject gaze an optometric chart. If the subjective measurement is conducted based on the corrected image, it is difficult to acquire accurate measurement results in the subjective measurement.

To solve the above problems, it is an object of the present invention to provide an optometry apparatus capable of conducting subjective measurement using an optometric chart accurately.

To achieve the above object, an aspect of the present invention provides an optometry apparatus including an eye chart presentation optical system that presents an optometric chart to an eye to be examined, and a control unit that controls the eye chart presentation optical system to present the optometric chart. The control unit executes instant presentation of the optometric chart by controlling the eye chart presentation optical system to finish presenting the optometric chart when an instant presentation time has elapsed after the eye chart presentation optical system starts presenting the optometric chart.

To achieve the above object, another aspect of the present invention provides a subjective measurement method for measuring ocular characteristics of an eye to be examined of a subject by presenting an optometric chart to the eye and determining how the subject sees the presented optometric chart. The method includes a step for starting presentation of the optometric chart, a step for determining whether or not an instant presentation time elapses after the presentation starts, and a step for finishing the presentation of the optometric chart when it is determined that the instant presentation time has elapsed.

BRIEF DESCRIPTION OF DRAWINGS

FIG. 10A is a schematic view showing a field of view of the eye when a subject gazes a first peripheral gazing point.

FIG. 10B is a schematic view showing a corresponding field of view of the eye when the first peripheral gazing point is replaced with the central gazing point in FIG. 10A.

FIG. 11A is a schematic view showing a field of view of the eye when a subject gazes a second peripheral gazing point.

FIG. 11B is a schematic view showing a corresponding field of view of the eye when the second peripheral gazing point is replaced with the central gazing point in FIG. 11A.

FIG. 13A is a schematic view showing a field of view of the eye when a subject gazes a fourth peripheral gazing point.

FIG. 13B is a schematic view showing a corresponding field of view of the eye when the fourth peripheral gazing point is replaced with the central gazing point in FIG. 13A.

DETAILED DESCRIPTION

Hereinafter, an optometry apparatus to conduct subjective measurement using an optometric chart and a method for subjective measurement using the optometric chart will be explained with reference to the drawings.

EXAMPLE 1

Figure 1:
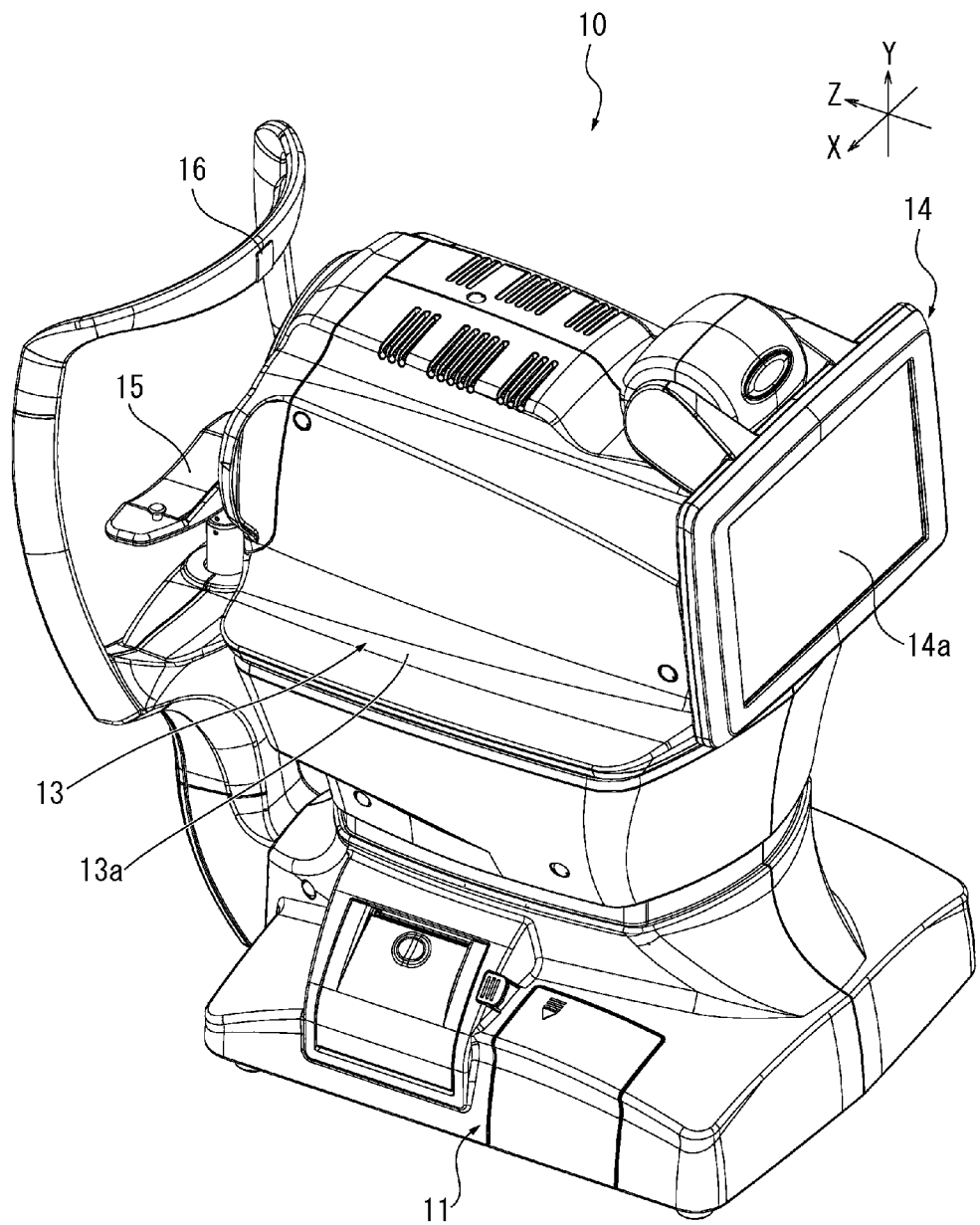
FIG. 1 is an overall view schematically showing an optometry apparatus, specifically an ocular refractive power measurement apparatus, according to Example 1 of the present invention.
Figure 2:
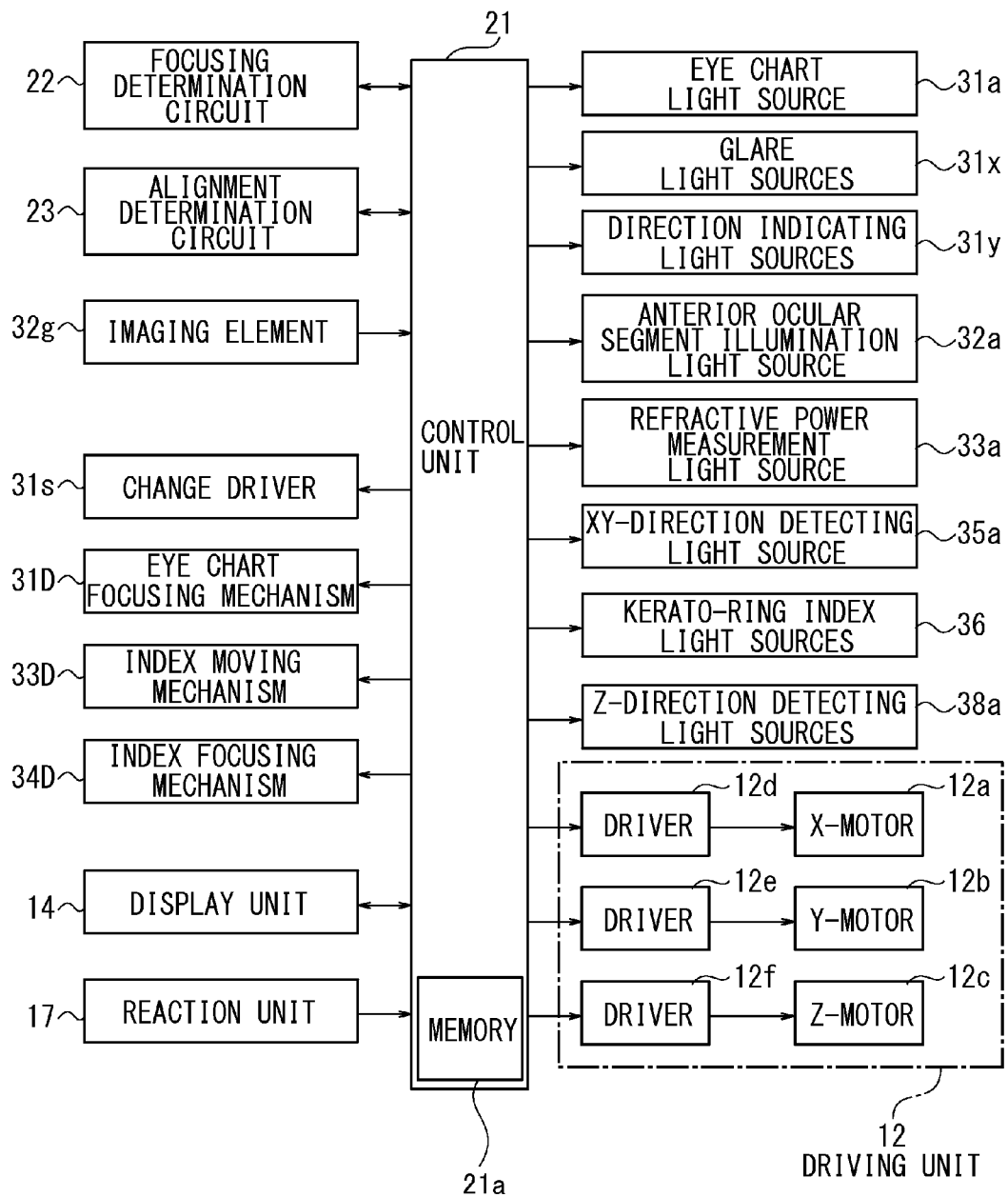
FIG. 2 is a block diagram of the ocular refractive power measurement apparatus according to Example 1.
Figure 3:
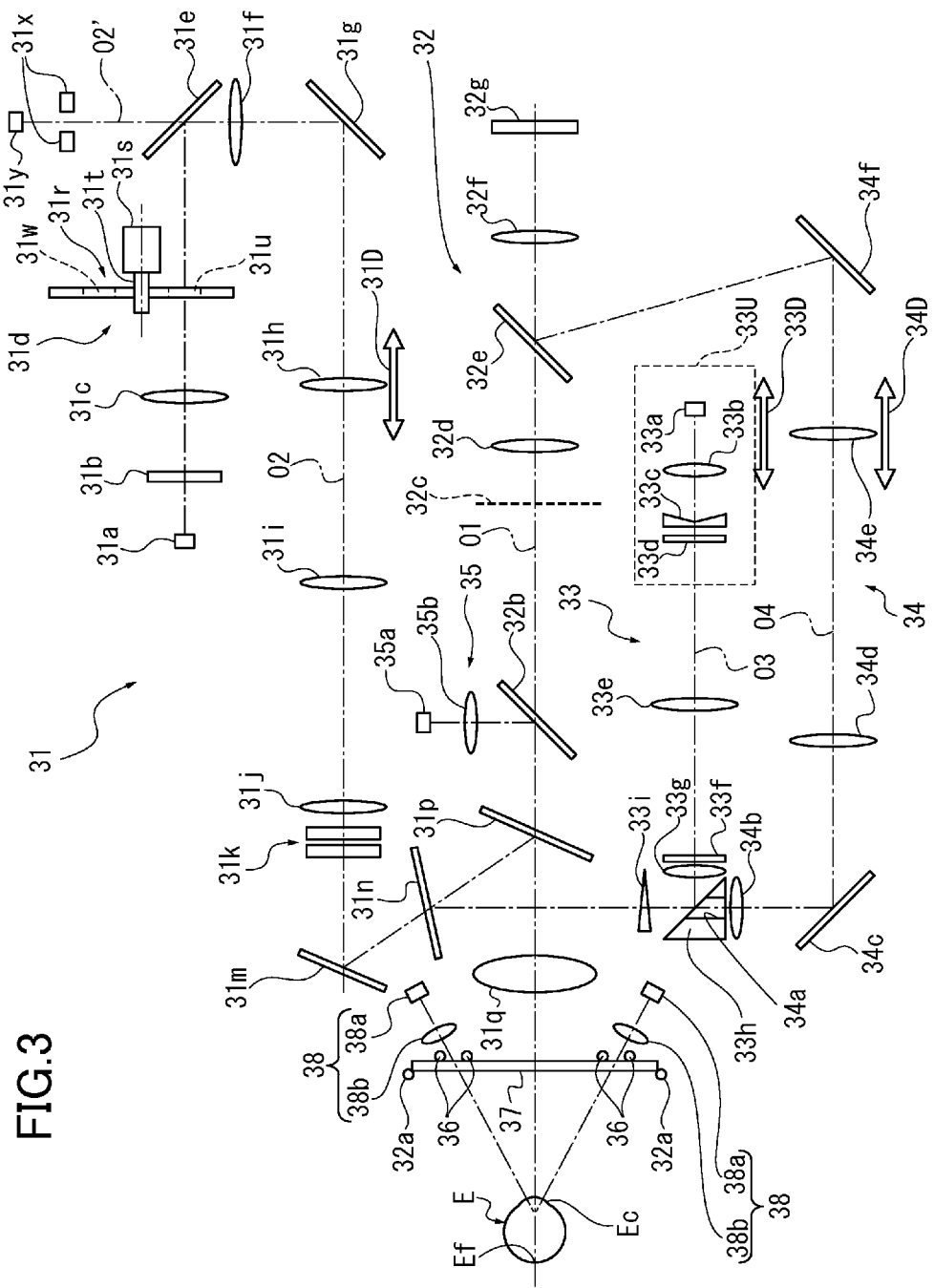
FIG. 3 is an explanatory view for explaining an optical arrangement of the ocular refractive power measurement apparatus according to Example 1.

An optometry apparatus, specifically an ocular refractive power measurement apparatus 10 according to Example 1 will be explained with reference to FIGS. 1 to 13. The ocular refractive power measurement apparatus 10 shown in FIG. 1 typically measures ocular refractive power of an eye to be examined E. The ocular refractive power measurement apparatus 10 has an objective measurement mode, which measures optical characteristics (ocular characteristics) including the ocular refractive power of the eye E in objective measurement (objective diagnosis), and a subjective measurement mode, which measures the optical characteristics (ocular characteristics) including the ocular refractive power of the eye E in subjective measurement (subjective diagnosis). Further, the ocular refractive power measurement apparatus 10 is adapted to execute (conduct) a subjective measurement method using an optometric chart of the present invention. Note that the eye E (with its ocular fundus Ef and cornea Ec (anterior ocular segment)) is schematically illustrated in FIG. 3

The ocular refractive power measurement apparatus 10 is equipped with a base 11 and a main body 13 which is movably connected to the base 11 via a driving unit 12. Optical systems (shown in FIG. 3) are installed inside the main body 13; and a display (display unit) 14, chin rest 15, and forehead pad 16 are installed outside the main body 13.

Figure 6:
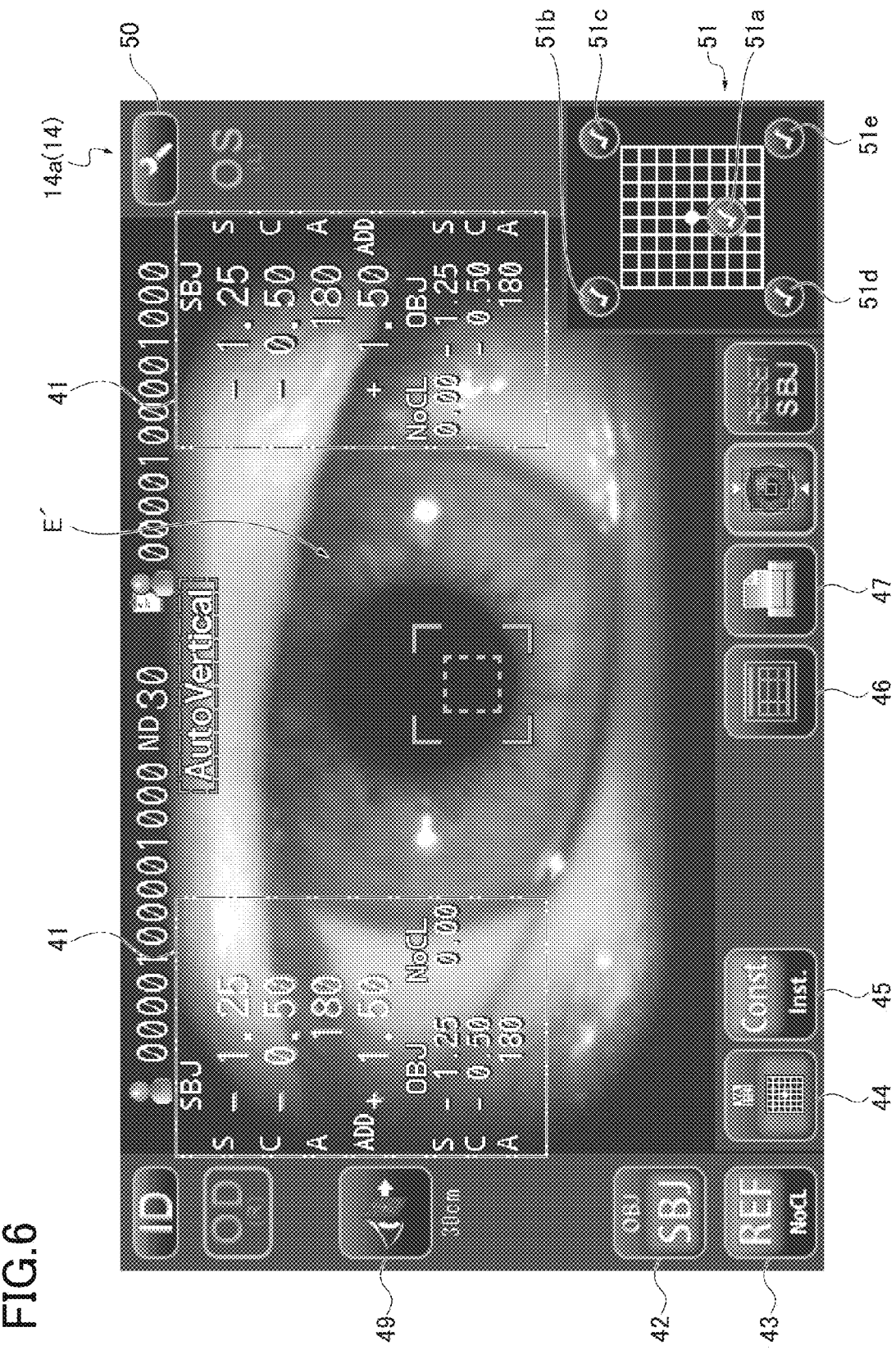
FIG. 6 is an explanatory view for explaining contents displayed on a screen of a display unit when conducting subjective measurement with continuous presentation of the grid chart.
Figure 7:
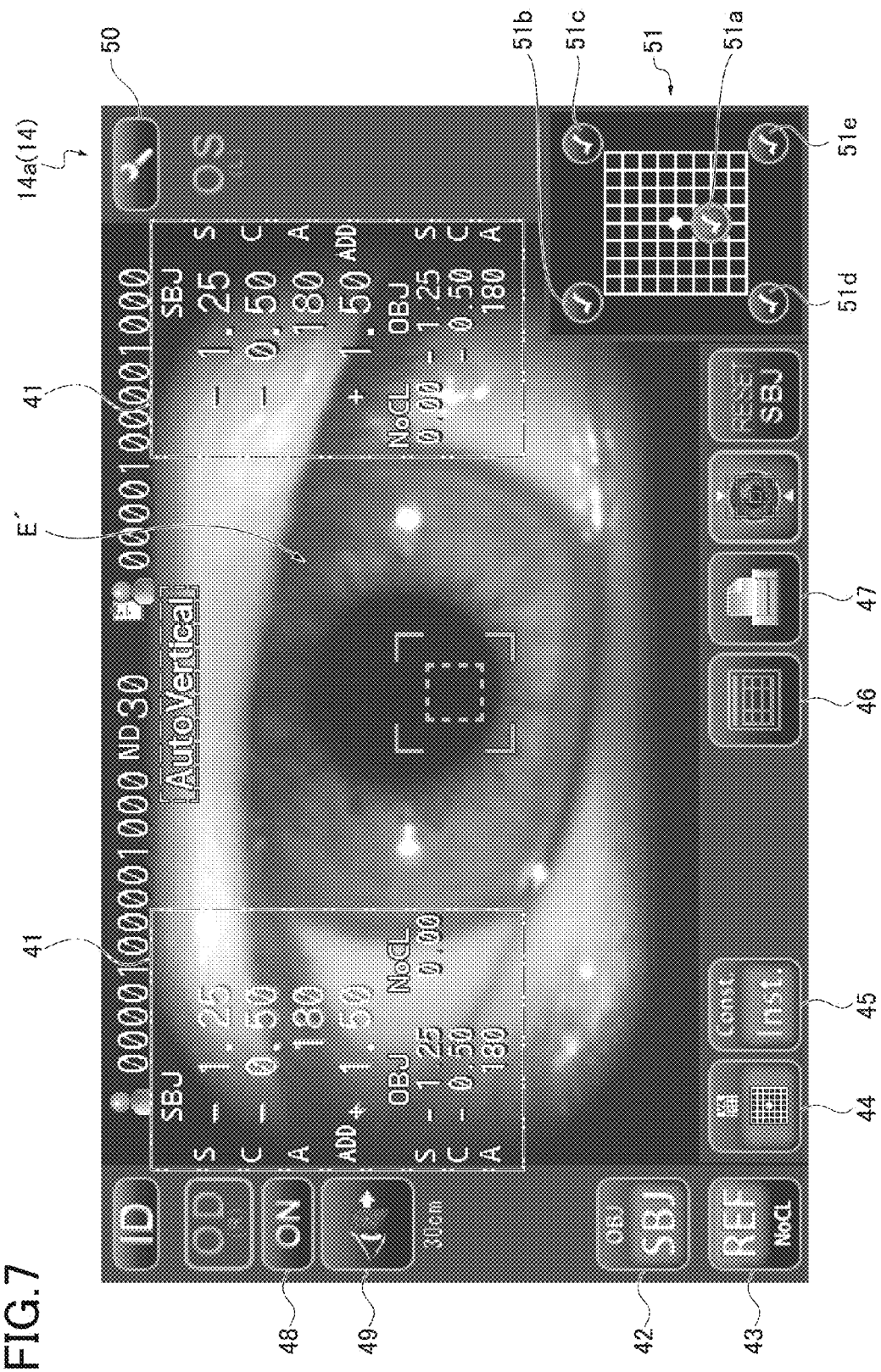
FIG. 7 is an explanatory view for explaining contents displayed on the screen of the display unit when conducting the subjective measurement with instant presentation of the grid chart.

The display unit 14 is a liquid crystal display and controlled by a control unit 21 (explained later, shown in FIG. 2) to display an image of the anterior ocular segment (corner Ec) of the eye to be examined E, examination results, and the like on a screen 14a (shown in FIGS. 6 and 7). The display unit 14 of Example 1 is designed to have a touch panel screen such that an examiner can manipulate (operate) the screen 14a of the display unit 14 to measure the optical characteristics (ocular characteristics) including the ocular refractive power, to image the anterior ocular segment (cornea Ec), to move the main body 13, to switchover between the subjective measurement mode and the objective measurement mode, to change an eye chart for subjective measurement, and the like. The display unit 14 displays icons for the abovementioned manipulations (shown in FIGS. 6 and 7) on the screen 14a, and the examiner can perform those manipulations by touching the icons. Note that it is also possible to provide switches on the base 11, main body 13, and/or display unit 14 to perform the measurements. Similarly, it is possible to provide a control lever and a switch on the base 11, main body 13, and/or display unit 14 to move the main body 13.

The chin rest 15 and forehead pad 16 are firmly installed at the base 11 to fix the face of the subject (patient), i.e., a position of the eye to be examined E, with respect to the main body 13 during the measurements. The chin rest 15 is a place to rest the chin of the subject, and the forehead pad 16 is a place to abut the forehead of the subject. When the face of the subject is fixed by the chin rest 15 and forehead pad 16, the eye E of the subject faces to a kerato-ring pattern 37 and an objective lens 31q (shown in FIGS. 3 and 5). Accordingly, the ocular refractive power measurement apparatus 10 can perform the measurements (objective measurement and subjective measurement) of the eye E appropriately.

In the ocular refractive power measurement apparatus 10, the display unit 14 (specifically, the screen 14a thereof) is generally provided on the examiner's side, while the chin rest 15 and the forehead pad 16 are provided on the subject's side. The display 14 is rotatably connected to the main body 13 and able to turn the screen 14a to the opposite side (i.e., the subject's side), sideways (X-axis direction), and the like. The main body 13 can be moved relatively to the base 11, i.e., relatively to the eye to be examined E (face of the subject) fixed by the chin rest 15 and forehead pad 16 by using the driving unit 12.

The driving unit 12 is adapted to move the main body 13 relatively to the base 11 in the up-and-down direction (Y-axis direction), the forward-and-backward direction (Z-axis direction), and the left-and-right direction (X-axis direction). Note the upside in the up-and-down direction (Y-axis direction), the subject's side in the forward-and-backward direction (Z-axis direction), and the near side of FIG. 1 in the left-and-right direction (X-axis direction) are defined as positive sides respectively (see arrows illustrated in FIG. 1). In Example 1, the driving unit 12 includes an X-axis motor 12a, a Y-axis motor 12b, and a Z-axis motor 12c together with corresponding X, Y, and Z drivers 12d, 12e, 12f.

The X-axis motor 12a moves the main body 13 relatively to the base 11 in the X-axis direction (left-and-right direction). The X-axis motor 12a is driven by controlling the X-axis driver 12d through the control unit 21.

The Y-axis motor 12b moves the main body 13 relatively to the base 11 in the Y-axis direction (up-and-down direction). The Y-axis motor 12b is driven by controlling the Y-axis driver 12e through the control unit 21.

The Z-axis motor 12c moves the main body 13 relatively to the base 11 in the Z-axis direction (forward-and-backward direction). The Z-axis motor 12c is driven by controlling the Z-axis driver 12f through the control unit 21.

Accordingly, the control unit 21 controls the driving unit 12 to move the main body 13 relatively to the chin rest 15 and forehead pad 16 fixed to the base 11.

The control unit 21 configures an electric control system of the ocular refractive power measurement apparatus 10 to integrally control each unit of the ocular refractive power measurement apparatus 10 in accordance with programs preinstalled into an internal memory 21a. As explained later, the control unit 21 adjusts a position of the main body 13 based on detection results (signals thereof) of a focusing determination circuit 22 and an alignment determination circuit 23. The control unit 21 also displays an image acquired by an imaging element 32g of an anterior ocular segment observation optical system 32 (shown in FIG. 3) on the screen 14a of the display unit 14. Further, the control unit 21 is connected to an eye chart light source 31a, glare light sources 31x, direction indicating light sources 31y, anterior ocular segment illumination light sources 32a, a refractive power measurement light source 33a, an XY-direction detecting light source 35a, kerato-ring index light sources 36, and Z-direction detecting light sources 38a through corresponding drivers (driving mechanism) and controls turning on/off each light source.

The control unit 21 is further connected to a change driver 31s of an eye chart change unit 31d (shown in FIG. 3, explained later) to change an eye chart held by a turret unit 31r (shown in FIG. 3). Furthermore, the control unit 21 controls an eye chart focusing mechanism 31D to appropriately move a focusing lens 31h (shown in FIG. 3, explained later), controls an index moving mechanism 33D to appropriately move an index unit 33U (shown in FIG. 3), and controls an index focusing mechanism 34D to appropriately move a focusing lens 34e (shown in FIG. 3). The control unit 21 also controls a driver (not shown) to adjust a relative position and an integral position of a pair of lenses of a VCC lens 31k (shown in FIG. 3, explained later). Further, the control unit 21 opens and closes a shutter 32c (shown in FIG. 3, explained later). The control unit 21 is connected to a reaction unit 17 (explained later) and displays information corresponding to manipulation of the reaction unit 17 on the screen 14a to notify the examiner. Note that any means to notify the examiner about the reactions can be applied as long as the reaction can be recognized by the examiner. The notification may be made by a sound or vibration. Besides, the control unit 21 stores the information corresponding to the manipulation of the reaction unit 17 into the memory 21a by relating to the currently executing measurement.

Next, the configuration of the control system of the ocular refractive power measurement apparatus 10 is explained with reference to FIG. 2. As illustrated in FIG. 2, the ocular refractive power measurement apparatus 10 includes, in addition to the above control unit 21, a focusing determination circuit 22, and an alignment determination circuit 23. The control unit 21 receives signals based on a light flux received by the imaging element 32g, specifically signals representing an image of the anterior ocular segment E' (shown in FIGS. 6 and 7) of the eye to be examined E, a ring index image for measuring ocular refractive power, a kerato-ring index image, a bright point image of an XY-alignment index light, and a bright point image for detecting the Z-axis direction. The control unit 21 generates image signals in accordance with the signals of the light flux received by the imaging element 32g and displays an image representing the image signals on the screen 14a (shown in FIGS. 6 and 7). The control unit 21 appropriately executes the abovementioned operations in accordance with the manipulation of the examiner inputted to the display unit 14 or with the program installed in the memory 21a.

The focusing determination circuit 22 determines whether or not the optical structure (main body 13) of the ocular refractive power measurement apparatus 10 is focused on the ocular fundus Ef (shown in FIG. 3) of the eye to be examined E. Specifically, it determines whether or not a gap in the forward-and-backward direction (Z-axis direction) is within an acceptable range. The focusing determination circuit 22 uses the kerato-ring index image, which is formed from the kerato-ring index light sources 36 and is acquired by the imaging element 32g, and the bright point image for detecting the Z-axis direction, which is formed by a Z-direction detection light projection system 38 (explained later) and is acquired by the imaging element 32g, to determine the focusing (the gap). The focusing determination circuit 22 then outputs the determination results (signals) to the control unit 21. The control unit 21 moves the main body 13 relatively to the base 11 in the Z-axis direction (forward-and-backward direction) based on the determination results inputted from the focusing determination circuit 22 until the control unit 21 receives a signal representing completion of the focusing (i.e., the gap being within the acceptable range) from the focusing determination circuit 22. With this, the control unit 21 can automatically perform Z-alignment.

The alignment determination circuit 23 determines whether or not a gap in the XY direction between a main optical axis O1 of the optical structure (main body 13) of the ocular refractive power measurement apparatus 10 and an optical axis of the eye to be examined E is within an allowable range. The gap may represent a difference and a direction in the left-and-right direction (X-axis direction) and a difference and a direction in the up-and-down direction (Y-axis direction). The alignment determination circuit 23 uses signals representing the XY-alignment index light (the bright point image), which is formed by an XY-alignment light projection optical system 35 (explained later) and is acquired by the imaging element 32g, to determine the gap. The alignment determination circuit 23 then outputs the determination results (signals) to the control unit 21. The control unit 21 moves the main body 13 relatively to the base 11 in the X-axis direction (left-and-right direction) and Y-axis direction (up-and-down direction) based on the determination results inputted from the alignment determination circuit 23 until the control unit 21 receives a signal representing that the gap is within the allowable range from the alignment determination circuit 23. With this, the control unit 21 can automatically perform XY-alignment.

The main body 13 includes the optical systems of the ocular refractive power measurement apparatus 10 inside a casing 13a. The ocular refractive power measurement apparatus 10 according to Example 1 is adapted to measure the ocular refractive power (i.e., spherical power, cylindrical power, cylinder axis angle, and the like) and shape of the cornea Ec of the eye E. To be specific, the ocular refractive power measurement apparatus 10 is adapted to measure the ocular refractive power of the eye E and the shape of the cornea Ec of the eye E by the objective measurement mode and adapted to measure the ocular refractive power of the eye E by the subjective measurement mode. The subjective measurement is conducted based on responses or reactions of the subject (patient), and the objective measurement is not conducted based on the response or reactions of the subject.

Next, the optical systems of the ocular refractive power measurement apparatus 10 are explained with reference to FIG. 3. As illustrated in FIG. 3, the ocular refractive power measurement apparatus 10 is equipped with an eye chart projection optical system 31, the anterior ocular segment observation optical system 32, a refractive power measurement light projection optical system 33, a refractive power measurement light receiving optical system 34, and the XY-alignment light projection optical system 35.

The eye chart projection optical system 31 projects an eye chart (fixation eye chart) onto the ocular fundus Ef of the eye E to fix or fog the eye E. The optical system 31 also projects an eye chart (subjective eye chart) onto the ocular fundus Ef of the eye E to ask the subject how he/she sees the projected eye chart in the subjective measurement mode. The anterior ocular segment observation optical system 32 observes the anterior ocular segment (cornea Ec) of the eye E. The refractive power measurement light projection optical system 33 projects a patterned light flux (measurement light flux) as a ring index onto the ocular fundus Ef of the eye E to measure the ocular refractive power of the eye E. The refractive power measurement light receiving optical system 34 receives the ring index that has been reflected by the ocular fundus Ef of the eye E with the imaging element 32g. The refractive power measurement light projection optical system 33 and the refractive power measurement light receiving optical system 34 configure a corneal shape and ocular refractive power measurement optical system (explained later) together with the anterior ocular segment observation optical system 32 and the kerato-ring index light sources 36 (explained later). The XY-alignment light projection optical system 35 projects an index light onto the eye E to detect the alignment in the XY direction.

The eye chart projection optical system 31 has the eye chart light source 31a, a color correction filter 31b, a collimator lens 31c, the eye chart change unit 31d, a half mirror 31e, a relay lens 31f, a mirror 31g, the focusing lens 31h, a relay lens 31i, a field lens 31j, the variable cross cylinder lens 31k (hereinafter called "VCC lens 31k"), a mirror 31m, dichroic filters 31n, 31p, and the objective lens 31q on an optical axis O2.

The eye chart change unit 31d changes the eye chart to be projected onto the ocular fundus Ef of the eye to be examined E by the eye chart projection optical system 31, and includes the turret unit 31r and change driver 31s. The turret unit 31r rotates around a rotary shaft 31t and holds a plurality of eye charts in the rotation direction. The eye chart change unit 31d is controlled by the control unit 21 to rotate the turret unit 31r around the rotary shaft 31t and to change a rotating posture of the turret unit 31r. That is to say, the eye chart change unit 31d is controlled by the control unit 21 to position one of the plural eye charts on the optical axis O2. Each of the plural eye charts of Example 1 passes light (light flux) emitted from the eye chart light source 31a and corrected by the color correction filter 31b such that a corresponding eye chart image is presented to the ocular fundus Ef of the eye E by the eye chart projection optical system 31 (explained later).

The turret unit 31r of Example 1 holds a landscape chart 31u, a grid chart 31v (shown in FIG. 4), and a visual acuity test chart 31w. The landscape chart 31u is an eye chart for fixing the eye of the subject (i.e., a fixation eye chart), and the landscape includes a point that is easily gazed by the subject. Note that although the landscape chart 31u is exemplified as the fixation eye chart in Example 1, it should not be limited thereto.

Figure 4:
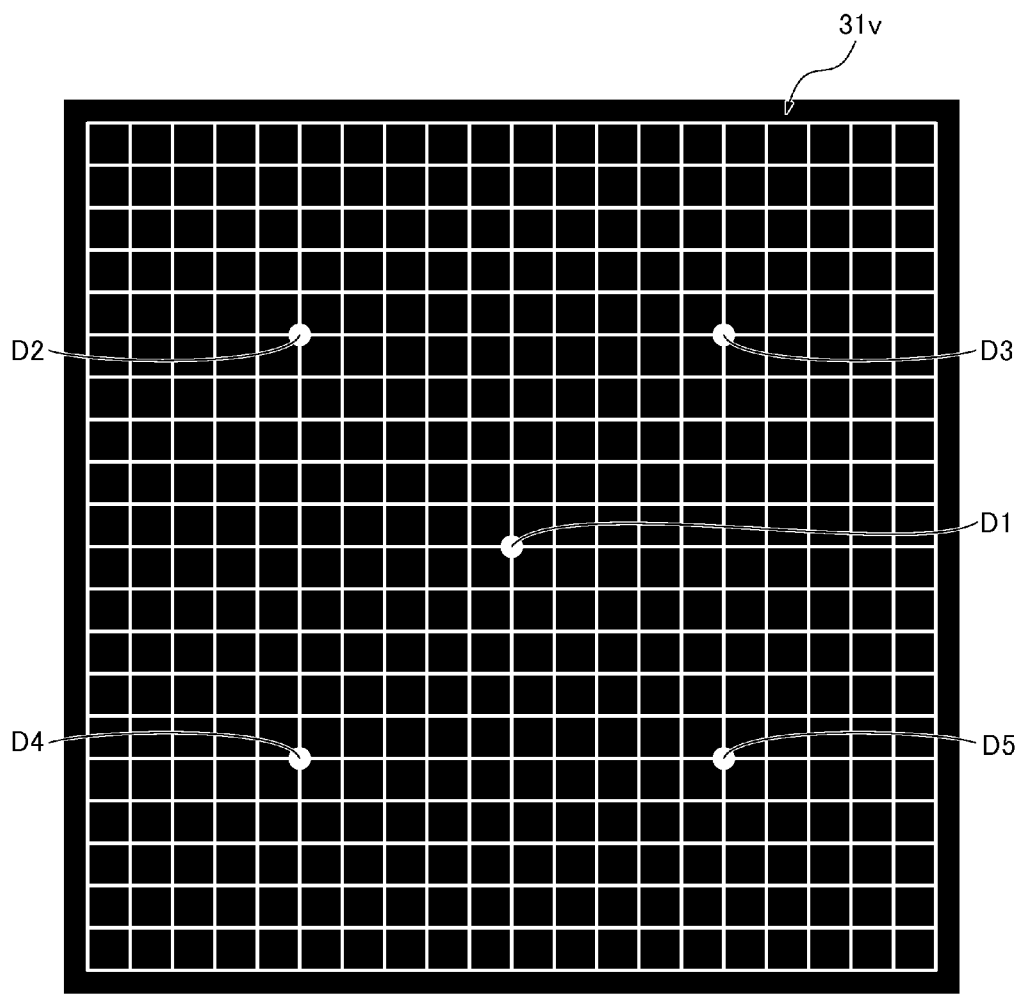
FIG. 4 is an explanatory view for explaining a grid chart (Amsler grid chart) used by the ocular refractive power measurement apparatus according to Example 1.

As illustrated in FIG. 4, the grid chart 31v is a so-called Amsler grid chart having a latticed pattern and is used for conducting a grid chart test (Amsler grid test) as the subjective measurement to ask how the subject sees the latticed pattern. That is to say, the grid chart 31v functions as an eye chart gazed by the subject for the subjective measurement (i.e., a subjective eye chart) and is used as an optometric chart to measure the optical characteristics (ocular characteristics) of the eye to be examined E. The grid chart 31v (Amsler grid chart) of Example 1 is configured such that the light (light flux), which has been emitted from the eye chart light source 31a and corrected by the color correction filter 31b, passes through the lines of the latticed pattern, i.e., the lines forming the pattern are lighted by the light flux, and the other portions are not lighted by the light flux. Note that the grid chart 31v may be configured such that the light flux passes through the other portions and the lines forming the pattern become dark.

The grid chart 31v of Example 1 has twenty boxes in each of the vertical and horizontal directions. The grid chart 31v of Example 1 has a central gazing point D1 in the center of the grid chart 31v and four peripheral gazing points (D2 to D5) surrounding the central gazing point D1. The four peripheral gazing points are each separated from the central gazing point (center) D1 by five boxes in the vertical and horizontal directions. The peripheral gazing point on the upper left is defined as D2, the peripheral gazing point on the upper right as D3, the peripheral gazing point on the lower left as D4, and the peripheral gazing point on the lower right as D5. To be specific, the peripheral gazing point D2 is positioned in the center of the upper left area, the peripheral gazing point D3 in the center of the upper right area, the peripheral gazing point D4 in the center of the lower left area, and the peripheral gazing point D5 in the center of the lower right area when the grid chart 31v is divided into the four areas by the vertical and horizontal lines passing through the central gazing point D1. By using the grid chart 31v (Amsler grid chart) for subjective measurement, i.e., for the grid chart test (Amsler grid chart test), it can determine that the eye to be examined E possibly has a disorder in the center (macular) of the retina (ocular fundus) Ef, or a disorder around the retina if the subject sees a wavy line, braking line, or blurred line in the latticed pattern.

The visual acuity test chart 31w is a subjective eye chart used to conduct a visual acuity test by asking the subject how he/she sees the test chart 31w. Letters such as alphabets and hiragana (Japanese characters), and Landolt rings are written on the visual acuity test chart 31w, and the sizes of these letters and rings are progressively graded in accordance with visual acuity values. Accordingly, the visual acuity test chart 31w functions as an eye chart to be gazed by the subject for the subjective measurement (i.e., subjective eye chart) and is used as an optometric chart to measure the optical characteristics (ocular characteristics, i.e., visual acuity) of the eye to be examined E. The visual acuity test chart 31w blocks the light (light flux), which has been emitted from the eye chart light source 31a and corrected by the color correction filter 31b, at the portions with the letters and rings, while passes the light (light flux) through the other portions. Hence, the portions with the letters and rings become dark and the other portions become bright on the visual acuity test chart 31w. Note that the visual acuity test chart 31w may pass the light at the portions with the letters and rings and blocks the light at the other portions.

Although not shown, the turret unit 31r may hold at least one of a polarized red-green (R&G) test chart, a precision stereoscopic test chart, a stereoscopic test chart, a cross phoria test chart, an aniseikonia test chart, a cyclophoria test chart, and the like. These charts also function as eye charts to be gazed by the subject for the subjective measurement (i.e., subjective eye charts) and are used as optometric charts to measure the optical characteristics (ocular characteristics) of the eye to be examined E. These charts also block the light (light flux), which has been emitted from the eye chart light source 31a and corrected by the color correction filter 31b, at the portions with corresponding letters, while passes the light (light flux) through the other portions. Hence, the portions with the letters become dark and the other portions become bright on the charts. Note that the visual acuity test chart 31w may pass the light at the portion with the letters and rings and blocks the light at the other portions.

As shown in FIG. 3, the eye chart light source 31a is a light source for projecting the eye chart held and positioned on the optical axis O2 by the turret unit 31r onto the eye to be examined E, and is configured by a white LED in Example 1. The eye chart focusing mechanism 31D is driven by the control unit 21 to move the focusing lens 31h to an arbitrary position on the optical axis O2 of the eye chart projection optical system 31 so as to fix/fog the eye E. The pair of lenses of the VCC lens 31k are rotated individually. The cylindrical power changes when these lenses are rotated in the opposite direction from each other. The cylinder axis angle changes when these lenses are rotated integrally in the same direction. A driver (not shown) of the VCC lens 31k is driven by the control unit 21 (shown in FIG. 2) to adjust the cylindrical power and cylinder axis angle for an astigmatic test. The dichroic filter 31p and objective lens 31q are disposed on the main optical axis O1 of the anterior ocular segment observation optical system 32 (an optical arrangement of the ocular refractive power measurement apparatus 10). Hence, the eye E of the subject, whose face is fixed by the chin rest 15 and forehead pad 16, is positioned on the main optical axis O1 in the ocular refractive power measurement apparatus 10 when conducting the measurement.

The eye chart projection optical system 31 additionally has the glare light sources 31x on an optical axis O2'. The optical axis O2' is an optical axis extending a part of the optical axis O2, which passes through the mirror 31g and the half mirror 31e via the relay lens 31f, from the half mirror 31e to the direction indicating light sources 31y. The glare light sources 31x project glare light onto the eye to be examined E, and are configured by LEDs in Example 1. The glare light sources 31x are controlled by the control unit 21 (shown in FIG. 2) to be lightened for a glare test. The glare test is conducted to detect a cataract on the eye E. A glare light flux emitted from the glare light sources 31x passes through the half mirror 31e and is guided along the optical axis O2 of the eye chart projection optical system 31. The glare light flux then proceeds to the eye E together with a target light flux (explained later).

In the eye chart projection optical system 31, the eye chart light source 31a emits white light, and the white light is corrected into a desired color by the color correction filter 31b. The corrected light is collimated into a parallel beam by the collimator lens 31c and passes through the eye chart to be the target light flux. In the eye chart projection optical system 31, the target light flux is then reflected by the half mirror 31e and the mirror 31g after passing through the relay lens 31f, so as to be guided to the focusing lens 31h. In the eye chart projection optical system 31, the target light flux passes through the focusing lens 31h, relay lens 31i, field lens 31j, and VCC lens 31k and is reflected by the mirror 31m. The reflected target light flux passes through the dichroic filter 31n and is guided to the dichroic filter 31p. The target light flux is further reflected by the dichroic filter 31p and is guided to the main optical axis O1 of the anterior ocular segment observation optical system 32, thereby proceeding to the eye E through the objective lens 31q. As a result, the eye chart projection optical system 31 can present (project) the eye chart that is positioned on the optical axis O2 by the eye chart change unit 31d to the eye E on the main optical axis O1 of the anterior ocular segment observation optical system 32 (the optical arrangement of the ocular refractive power measurement apparatus 10). In other words, the eye chart projection optical system 31 functions as an eye chart presentation optical system to present the optometric chart to the eye E as a subjective eye chart to be gazed for the subjective measurement.

When the grid chart 31v (shown in FIG. 4) is positioned on the optical axis O2 of the eye chart projection optical system 31, the grid chart 31v is presented to the eye to be examined E under a condition equivalent to a predetermined size and a distance of 30 to 40 cm (30 cm in Example 1) from the eye E. Further, the eye chart projection optical system 31 can decrease the size of the grid chart 31v presented to the eye E. Specifically, the eye chart projection optical system 31 can install a masking member on the turret unit 31r of the eye chart change unit 31d or on the optical path detachably to decrease the size of the presented grid chart 31v. Note that it may preinstall the grid chart 31v of different sizes at the turret unit 31r instead of installing the masking member.

The eye chart projection optical system 31 fixes the sight line of the subject by having the subject gaze the fixation eye chart, i.e., the target light flux projected onto the eye to be examined E through the landscape chart 31u. Further, the eye chart projection optical system 31 fogs the eye E by moving the focusing lens 31h from a position where the eye E is fixed to a position where the fixation eye chart becomes out of focus. Additionally, the eye chart projection optical system 31 conducts the subjective measurement by having the subject gaze the target light flux projected as a subject eye chart onto the eye E through the optometric chart (grid chart 31v or the like). Details of the subjective measurement using the grid chart 31v will be explained later. The optical system 31 can perform a visual acuity test with the visual acuity test chart 31w, and perform other tests in accordance with the presented optometric charts.

The anterior ocular segment observation optical system 32 has anterior ocular segment illumination light sources 32a, has a half mirror 32b, the shutter 32c, a relay lens 32d, a dichroic filter 32e, an imaging lens 32f, and the imaging element 32g on the main optical axis O1, and shares the objective lens 31q and dichroic filter 31p with the eye chart projection optical system 31. The imaging element 32g is a two-dimensional solid state imaging device, particularly a CCD imaging sensor in Example 1.

The anterior ocular segment illumination light sources 32a directly illuminate the anterior ocular segment (cornea Ec) of the eye to be examined E when lighted. A plurality of the illumination light sources 32a (only two of them are shown in FIG. 3) are disposed around the below-mentioned kerato-ring pattern 37 in the main body 13 at the end of the subject's side in the forward-and-backward direction (positive side in the Z-axis direction).

In the anterior ocular segment observation optical system 32, the illumination light sources 32a emit illumination light flux to illuminate the anterior ocular segment (cornea Ec) of the eye to be examined E, and the objective lens 31q acquires the illumination light fluxes reflected by the anterior ocular segment. The anterior ocular segment observation optical system 32 opens the shutter 32c to clear the optical path on the main optical axis O1 at this time. In the anterior ocular segment observation optical system 32, the reflected illumination light flux passes through the dichroic filter 31p and the half mirror 32b via the objective lens 31q. The illumination light flux then passes through the relay lens 32d and the dichroic filter 32e and is formed into an image on the imaging element 32g (specifically, on the light-receiving surface of the imaging element 32g) by the imaging lens 32f. The imaging element 32g outputs imaging signals in accordance with the formed (acquired) image to the control unit 21 (shown in FIG. 2). The control unit 21 displays an image of the anterior ocular segment (cornea Ec) on the display unit 14 (shown in FIG. 1 or the like.) in accordance with the inputted image signals. Accordingly, the anterior ocular segment observation optical system 32 forms the image of the anterior ocular segment (cornea Ec) on the light-receiving surface of the imaging element 32g and to display the image of the anterior ocular segment (anterior ocular segment image E') on the display unit 14. Note that the anterior ocular segment illumination light sources 32a of the anterior ocular segment observation optical system 32 may be turned off and the shutter 32c may shut the optical path on the main optical axis O1 when an ocular refractive power measurement is conducted after the alignment has been performed.

The refractive power measurement light projection optical system 33 includes the refractive power measurement light source 33a, a collimator lens 33b, a conical prism 33c, a refractive power measurement ring 33d, a relay lens 33e, an aperture ring 33f, a field lens 33g, a holed prism 33h, and a rotary prism 33i on an optical axis O3 and shares the dichroic filters 31n, 31p and the objective lens 31q with the eye chart projection optical system 31. The refractive power measurement light source 33a and the aperture ring 33f are located in optically conjugate positions, and the refractive power measurement ring 33d and the ocular fundus Ef of the eye E are located in optically conjugate positions. The refractive power measurement light source 33a, collimator lens 33b, conical prism 33c, and refractive power measurement ring 33d configure the index unit 33U. The index unit 33U is moved by the index moving mechanism 33D along the optical axis O3 of the refractive power measurement light projection optical system 33.

In the refractive power measurement light projection optical system 33, a light flux emitted from the refractive power measurement light source 33a is collimated into a parallel beam by the collimator lens 33b and is guided to the refractive power measurement ring 33d through the conical prism 33c. The parallel beam is formed into a patterned light flux representing a ring index for measuring ocular refractive power by passing through the ring pattern formed on the ring 33d. The patterned light flux is guided to the holed prism 33h through the relay lens 33e, aperture ring 33f, and field lens 33g. The patterned light flux is then reflected by the reflective surface of the holed prism 33h toward the dichroic filter 31n via the rotary prism 33i. Further, the patterned light flux is reflected by the dichroic filters 31n, 31p and is guided onto the main optical axis O1 of the anterior ocular segment observation optical system 32 (the optical arrangement of the ocular refractive power measurement apparatus 10). Further, the patterned light flux is imaged on the ocular fundus Ef of the eye E by the objective lens 31q. Accordingly, the refractive power measurement light projection optical system 33 can project the patterned light flux, which represents the ring index for measuring ocular refractive power, as the measurement light onto the ocular fundus Ef of the eye E on the main optical axis O1 of the anterior ocular segment observation optical system 32 (the optical arrangement of the ocular refractive power measurement apparatus 10).

Figure 5:
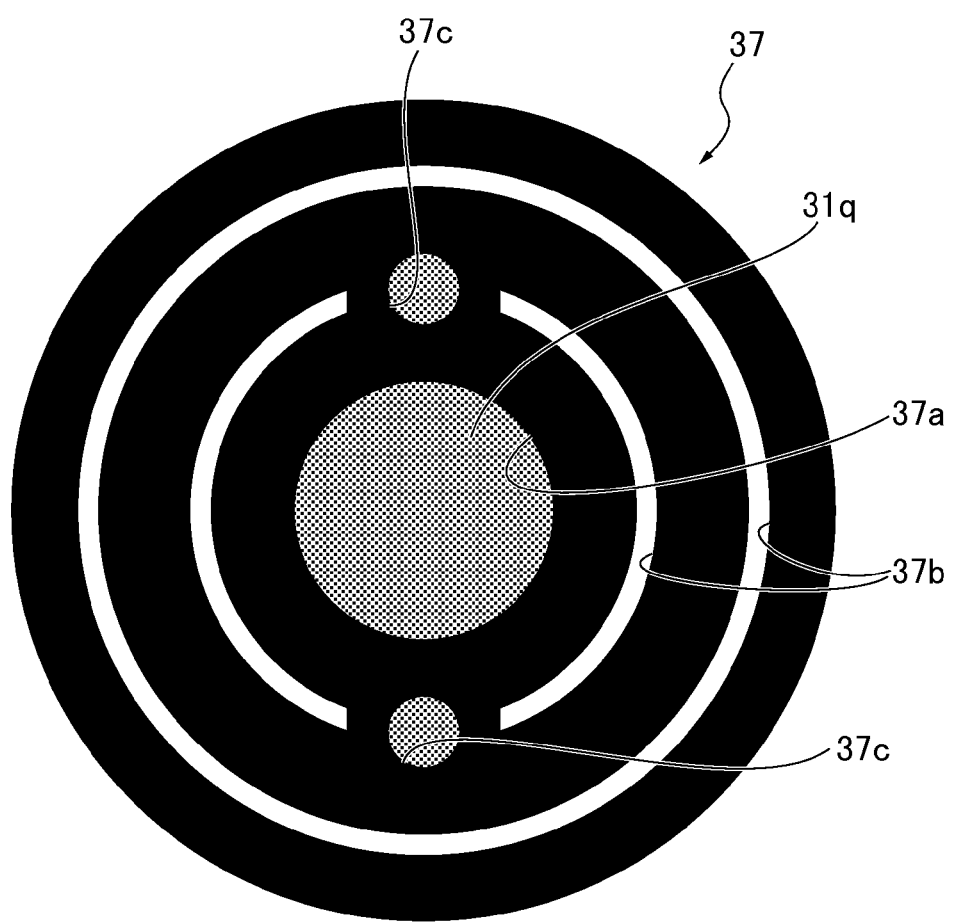
FIG. 5 is an explanatory view for explaining a kerato-ring pattern used by the ocular refractive power measurement apparatus according to Example 1.

The refractive power measurement light projection optical system 33 also includes the kerato-ring index light sources 36 at the front side of the objective lens 31q. The kerato-ring index light sources 36 are disposed on the kerato-ring (ring for measuring the corneal shape) pattern 37 with a predetermined distance from the eye to be examined E and are coaxially provided with the main optical axis O1 of the anterior ocular segment observation optical system 32. As shown in FIG. 5, the kerato-ring pattern 37 is substantially a flat plate shape and includes a center hole 37a, plurality of slits 37b provided coaxially with the main optical axis O1, and light transmission holes 37c symmetrically provided with respect to the main optical axis O1. The center of the center hole 37a coincides with the main optical axis O1 so that the objective lens 31q is exposed through the center hole 37a. The kerato-ring index light sources 36 are positioned corresponding to the slits 37b of the kerato-ring pattern 37 such that light fluxes (measurement light) are projected onto the eye E (cornea Ec) through the corresponding slits 37b and formed into the kerato-ring index on the cornea Ec. The kerato-ring index (light fluxes) is then reflected by the cornea Ec of the eye E and imaged on the imaging element 32g by the anterior ocular segment observation optical system 32. Accordingly, the anterior ocular segment observation optical system 32 can display the kerato-ring index image together with the image of the anterior ocular segment (cornea Ec) on the display unit 14.

Further, the Z-direction detection light projection system 38 is provided on the back side of the kerato-ring pattern 37 in the refractive power measurement light projection optical system 33, as shown in FIG. 3. The Z-direction detection light projection system 38 has Z-direction detecting light sources 38a and condenser lenses 38b positioned corresponding to the light transmission holes 37c of the kerato-ring pattern 37 (shown in FIG. 5). The Z-direction detection light projection system 38 condenses light fluxes emitted from the Z-direction detecting light sources 38a by the corresponding condenser lenses 38b, and guides the condensed light fluxes to the eye to be examined E through the corresponding light transmission holes 37c of the kerato-ring pattern 37 (shown in FIG. 5) so as to form bright points for detecting Z-axis direction. The Z-direction detection light projection system 38 uses the formed bright points for detecting Z-axis direction together with the kerato-ring index formed by the kerato-ring index light sources 36 to adjust the position in the frontward-and-backward direction (Z-axis direction), i.e., to perform the Z-alignment. Accordingly, the examiner can perform the Z-alignment by moving the main body 13 to appropriately adjust the relative positions of the bright points and the kerato-ring index. Further, as described above, in the automatic alignment mode, the focusing determination circuit 22 can measure the gap between the eye E and the main body 13 in the Z-axis direction using the signals sent from the imaging element 32g that are generated based on the relative positions of the bright points and the kerato-ring index. The control unit 21 then controls the Z-axis driver 12f to appropriately move the main body 13 in the Z-axis direction in accordance with the measured gap to perform the Z-alignment.

The refractive power measurement light receiving optical system 34 includes a hole 34a of the holed prism 33h, a field lens 34b, a mirror 34c, a relay lens 34d, a focusing lens 34e, and a mirror 34f on an optical axis O4, shares the objective lens 31q, and dichroic filters 31p, 31n with the eye chart projection optical system 31, shares the rotary prism 33i with the refractive power measurement light projection optical system 33, and shares the dichroic filter 32e, imaging lens 32f, and imaging element 32g with the anterior ocular segment observation optical system 32. The index focusing mechanism 34D is controlled by the control unit 21 (shown in FIG. 2) to appropriately move the focusing lens 34e along the optical axis O4 of the optical system 34 so as to focus on the anterior ocular segment (cornea Ec) of the eye to be examined E.

In the refractive power measurement light receiving optical system 34, the patterned light flux, which has been guided to the ocular fundus Ef by the refractive power measurement light projection optical system 33 and reflected by the ocular fundus Ef, is condensed by the objective lens 31q and is guided to the rotary prism 33i after reflecting the condensed patterned light by the dichroic filters 31p, 31n. The reflected patterned light flux is then guided to the hole 34a of the holed prism 33h via the rotary prism 33i. The reflected patterned light flux passed through the hole 34a is reflected by the mirror 34c after passing through the field lens 34b and guided to the focusing lens 34e through the relay lens 34d. The position of the focusing lens 34e on the optical axis O4 is adjusted such that an imaging point of the reflected patterned light flux (i.e., the ring index for measuring ocular refractive power) is set on the light-receiving surface of the imaging element 32g. The reflected patterned light flux is then reflected by the mirror 34f after passing through the focusing lens 34e and further reflected by the dichroic filter 32e toward the main optical axis O1 of the anterior ocular segment observation optical system 32 (the optical arrangement of the ocular refractive power measurement apparatus 10). The reflected patterned light flux, i.e., the ring index for measuring ocular refractive power, is imaged on the light-receiving surface of the imaging element 32g by the imaging lens 32f. The imaging element 32g outputs image signals in accordance with the acquired image to the control unit 21 (shown in FIG. 2). The control unit 21 displays an image of the ring index for measuring ocular refractive power on the display unit 14 (shown in FIG. 1) based on the inputted image signals.

The XY-alignment light projection optical system 35 includes the XY-direction detecting light source 35a and a condenser lens 35b, shares the half mirror 32b with the anterior ocular segment observation optical system 32, and shares the dichroic filter 31p and objective lens 31q with the eye chart projection optical system 31. The XY-direction detecting light source 35a is a spot light source forming an XY-alignment index light flux and configured with an LED.

In the XY-alignment light projection optical system 35, the XY-alignment index light flux emitted from the XY-direction detecting light source 35a is condensed by the condenser lens 35b and reflected by the half mirror 32b toward the main optical axis O1 of the anterior ocular segment observation optical system (the optical arrangement of the ocular refractive power measurement apparatus 10). The XY-alignment index light flux passes through the dichroic filter 31p and is guided to the objective lens 31q. The XY-alignment index light flux passed through the objective lens 31q is then projected onto the cornea Ec of the eye to be examined E. The XY-alignment index light flux projected onto the eye E (cornea Ec) is reflected by the cornea Ec of the eye E and projected onto the imaging element 32g by the anterior ocular segment observation optical system 32 so as to be formed into a bright point image representing the XY-alignment index image. The XY-alignment light projection optical system 35 can perform the XY-alignment to adjust the position of the main body 13 in the X and Y-axis directions by using the formed bright point image (XY-alignment index image). Specifically, the examiner can perform the XY-alignment by moving the main body 13 to locate the bright point image (XY-alignment index image), within a preset alignment mark. In the automatic alignment mode, the alignment determination circuit 23 can measure the gap between the eye E and the main body 13 in the X-axis direction and Y-axis direction using the XY-alignment index image. The control unit 21 then controls the X-axis driver 12d and Y-axis driver 12e to move the main body 13 in the X and Y-axis directions in accordance with the measured gap to perform the XY-alignment.

Next, an overall operation to measure the ocular refractive power (spherical power, cylindrical power, cylinder axis angle, and the like) and the shape of the corner Ec of the eye to be examined E using the ocular refractive power measurement apparatus 10 according to Example 1 will be explained. Note the following operation of the ocular refractive power measurement apparatus 10 is executed by the control unit 21 (shown in FIG. 2).

First, the examiner turns on a power switch of the apparatus 10 and manipulates the display unit 14 to conduct the objective measurement. The ocular refractive power measurement apparatus 10 then turns on the anterior ocular segment illumination light sources 32a of the anterior ocular segment observation optical system 32 and displays an image of the anterior ocular segment (cornea Ec) on the display unit 14. As described above, the ocular refractive power measurement apparatus 10 then moves the main body 13 with respect to the base 11 to perform the alignments in the up-and-down direction (Y-axis direction), left-and-right direction (X-axis direction), and forward-and-backward direction (Z-axis direction).

The ocular refractive power measurement apparatus 10 next turns on the refractive power measurement light source 33a of the refractive power measurement light projection optical system 33 to project the patterned light flux representing the ring index for measuring ocular refractive power onto the ocular fundus Ef of the eye to be examined E. In the ocular refractive power measurement apparatus 10, the ring index for measuring ocular refractive power is reflected by the ocular fundus Ef and is imaged on the imaging element 32g by the refractive power measurement light receiving optical system 34. The imaging element 32g outputs imaging signals in accordance with the acquired image to the control unit 21 (shown in FIG. 2). The control unit 21 displays an image of the ring index for measuring ocular refractive power on the display unit 14 (shown in FIG. 1) based on the inputted image signals. The control unit 21 then measures the ocular refractive power, i.e., the spherical power, cylindrical power, and cylinder axis angle, using the displayed image (specifically, using the image signals inputted from the imaging element 32g). The detail of how to measure the ocular refractive power (i.e., the spherical power, cylindrical power, and cylinder axis angle) is identical to that of a conventionally known technique, and thus it is not explained herewith.

Further, the ocular refractive power measurement apparatus 10 turns on the kerato-ring index light sources 36 of the refractive power measurement light projection optical system 33 to project the kerato-ring index onto the cornea Ec of the eye to be examined E. The ocular refractive power measurement apparatus 10 then forms the kerato-ring index, which has been reflected by the cornea Ec of the eye E, on the imaging element 32g by the anterior ocular segment observation optical system 32. The imaging element 32g outputs image signals in accordance with the acquired image to the control unit 21 (shown in FIG. 2). The control unit 21 displays an image of the kerato-ring index on the display unit 14 (shown in FIG. 1) based on the inputted image signals. The control unit 21 then measures the shape of the cornea Ec based on the image displayed on the display unit 14 (image signals from the imaging element 32g). The detail of how to measure the shape of the cornea Ec is identical to that of a conventionally known technique, and thus it is not explained herewith. Accordingly, the kerato-ring index light sources 36 of the refractive power measurement light projection optical system 33 in the ocular refractive power measurement apparatus 10 function as an ocular characteristics measurement light projection optical system to project another measurement light onto the eye E for measuring the ocular characteristics of the eye E other than the ocular refractive power. Further, the anterior ocular segment observation optical system 32 functions as the ocular characteristics measurement light receiving optical system to receive the another measurement light that is reflected by the eye E.

The ocular refractive power measurement apparatus 10 can measure the ocular refractive power (i.e., spherical power, cylindrical power, cylinder axis angle, and the like) and the shape of the cornea Ec of the both eyes by executing the above operation for the both eyes of the subject. The ocular refractive power measurement apparatus 10 can execute the abovementioned measurement without having the subject close or cover his/her eye that is not to be examined.

Next, a characteristic configuration of the ocular refractive power measurement apparatus 10 according to Example 1 of the present invention will be explained mainly with reference to FIGS. 6 to 13. FIG. 6 shows a situation after conducting the objective measurement and illustrates contents displayed on the display unit 14 (screen 14a) when conducting the subjective measurement with the continuous presentation of the grid chart 31v. FIG. 7 also shows a situation after conducting the objective measurement and illustrates contents displayed on the display unit 14 (screen 14a) when conducting the subjective measurement with the instant presentation of the grid chart 31v.

As explained above, the ocular refractive power measurement apparatus 10 can conduct the subjective measurement using the optometric chart (e.g., grid chart 31v) by having the subject gaze the target light flux passing through the optometric chart (the grid chart 31v (Amsler grid chart)).

The apparatus 10 can perform continuous presentation and instant presentation of the optometric chart such as the grid chart 31v. The continuous presentation means the apparatus 10 keeps presenting the optometric chart to the eye E (subject) during the subjective measurement. On the other hand, the instant presentation means the apparatus 10 presents the optometric chart to the eye E (subject) only for a moment (for an instant presentation time). This is performed because of the following reason.

A subject (human being) commonly forms an image by imaging the light, which is incident on the eye to be examined E, on the retina (ocular fundus) Ef and transmits nerve signals representing the formed image to his/her brain. However, the brain may not recognize the image exactly as the one representing the transmitted nerve signals, but recognize the image after appropriately correcting it in the brain. In the subjective measurement, it determines how the subject sees and recognizes the optometric chart. Accordingly, how the subject sees and recognizes the optometric chart may not represent the exact image formed on the retina (ocular fundus) Ef based on the light incident on the eye. Rather, it may represent the image corrected in his brain. For example, in the grid chart test (Amsler grid chart test), the subject may recognize that he/she sees an appropriate latticed pattern by unintentionally correcting the image in his/her brain even if the image formed on the retina (ocular fundus) Ef actually has a wavy line, braking line, or blurred line. Consequently, it is difficult to accurately measure the ocular refractive power at the eye E by simply conducting the subjective measurement with the optometric chart.

Therefore, the ocular refractive power measurement apparatus 10 of Example 1 of the present invention is configured to present the optometric chart to the eye to be examined E (subject) only for a moment (for an instant presentation time) when conducting the subjective measurement (subjective measurement with the instant presentation). This is because an action in which the subject corrects the image representing the transmitted nerve signals in his/her brain and recognizes the corrected image as what he/she sees occurs when the subject sees an image for a certain time or longer. In other words, if the optometric chart is presented to the eye E (subject) only for a moment, the subject cannot correct the image representing the transmitted nerve signals in his/her brain to recognize the image, and recognizes the image exactly as formed on the retina (ocular fundus) Ef. Accordingly, the ocular refractive power measurement apparatus 10 of Example 1 of the present invention sets the instant presentation time to prevent the subject's brain from correcting the image representing the transmitted nerve signals. To be specific, the instant presentation time is initially set to be 0.25 second as a preferred example and can be modified from 0.01 second as the lower limit to 2.00 second as the upper limit. With this, the ocular refractive power measurement apparatus 10 can accurately measure the ocular refractive power of the eye E (in accordance with the optometric chart) by presenting the grid chart 31v only for the instant presentation time.

Further, as explained above, the ocular refractive power measurement apparatus 10 of Example 1 of the present invention is configured to present the optometric chart continuously to the eye to be examined E (subject) (continuous presentation) to conduct the subjective measurement (subjective measurement with continuous presentation). This is performed because of the following reason. In the conventional ocular refractive power measurement apparatuses, an optometric chart, for example, the visual acuity test chart 31w (shown in FIG. 3) is continuously presented to the eye E (subject) to determine how the subject sees the visual acuity test chart 31w in the subjective measurement. That is to say, some examiners may prefer this conventional testing process. Hence, the apparatus 10 of Example 1 is also configured to conduct the subjective measurement with the continuous presentation. Specifically, the ocular refractive power measurement apparatus 10 can switch between the continuous presentation and the instant presentation by using a presentation mode switching icon 45 (shown in FIGS. 6 and 7).

The ocular refractive power measurement apparatus 10 includes the direction indicating light sources 31y on the optical axis O2' of the eye chart projection optical system 31 and the reaction unit 17 (shown in FIG. 2). One of the direction indicating light sources 31y forms a bright point to indicate a direction to present the optometric chart to the eye to be examined E (subject). In Example 1, the direction indicating light sources 31y form the bright point at a position corresponding to the center of the optometric chart (the central gazing point D1 (shown in FIG. 4)). Accordingly, the ocular refractive power measurement apparatus 10 can form the bright point in the position corresponding to the center (central gazing point D1 (shown in FIG. 4)) of the optometric chart by the direction indicating light sources 31y even before presenting the optometric chart to the eye E. The bright point formed in the position corresponding to the central gazing point D1 functions as a presentation position marker.

Further, the ocular refractive power measurement apparatus 10 is configured to form bright points also at the positions corresponding to the four corners (peripheral gazing points D2 to D5 (shown in FIG. 4)) of the grid chart 31v by the direction indicating light sources 31y. As explained later, the ocular refractive power measurement apparatus 10 needs to have the subject gaze the four corners of the grid chart 31v (peripheral gazing points D2 to D5 (shown in FIG. 4)). Accordingly, the ocular refractive power measurement apparatus 10 can also form bright points at the positions corresponding to the four corners in the grid chart 31v (peripheral gazing points D2 to D5) respectively by the direction indicating light sources 31y. The bright points formed at the positions corresponding to the peripheral gazing points D2 to D5 also function as the presentation position markers. Although not shown, in Example 1, a plurality of the direction indicating light sources 31y are installed at predetermined positions respectively to form the bright points at the positions corresponding to the four corners respectively. Note that the bright points may be formed at the positions corresponding to the four corners by using a single direction indicating light source 31y together with a light shielding plate, or the like, and therefore it should not be limited thereto. Further, as long as the bright points can be formed at the positions corresponding to the four corners, the locations of the direction indicating light sources 31y should not be limited to the ones of Example 1. When the light sources are disposed in another optical system, this optical system also functions as the eye chart presentation optical system.

The direction indicating light sources 31y are turned on by the control unit 21 prior to conducting the subjective measurement with the instant presentation, i.e., prior to turning the eye chart light source 31a on to present the optometric chart only for the instant presentation time. Note the direction indicating light sources 31y may be turned on constantly or intermittently (i.e., flashing). With this, the ocular refractive power measurement apparatus 10 can form the bright points at the position corresponding to the central position (central gazing point D1 (shown in FIG. 4)) and at the positions corresponding to the four corners (peripheral gazing points D2 to D5 (shown in FIG. 4)) of the grid chart 31v as the presentation position markers prior to presenting the optometric chart.

The reaction unit 17 is manipulated by the subject, i.e., is used to input the signals in response to how the subject sees the optometric chart in the subjective measurement. The reaction unit 17 of Example 1 includes a manipulation lever on the main body 13 and is connected to the control unit 21. The manipulation lever of the reaction unit 17 can be pressed toward the main body 13 and tilted toward the front-and-rear direction and right-and-left direction thereof. As explained, the control unit 21 displays information representing the manipulations inputted to the reaction unit 17 on the screen 14a of the display unit 14 to notify the examiner. The control unit 21 can determine ON/OFF states set by the subject by detecting the manipulation of pressing the manipulation lever toward the main body 13 in the reaction unit 17. Specifically, the subject presses the manipulation lever toward the main body 13 to set the ON state when the subject sees a wavy line, braking line, or blurred line in the latticed pattern during the subjective measurement using the grid chart 31v. With this, the examiner can quickly determine the condition of the subject. Further, the control unit 21 (shown in FIG. 2) can determine to which direction the subject tilts the manipulation lever. Specifically, the subject tilts the manipulation lever to input a direction to which the visual acuity test chart 31w indicates in the subjective measurement. Accordingly, the examiner can quickly determine the direction indicated by the subject. Note although the reaction unit 17 of Example 1 is configured to be applied for the subjective measurements using the grid chart 31v and visual acuity test chart 31w. How to manipulate the reaction unit 17 should be modified based on what kind of optometric charts are installed.

In the ocular refractive power measurement apparatus 10, the display unit 14 is controlled by the control unit 21 (shown in FIG. 2) to display icons on the screen 14a for selecting (switching) the operations by using the function of the touch panel, as shown in FIGS. 6 and 7. Measurement results 41 of Example 1 represent values of the ocular refractive power measured by the subjective measurement and values of the ocular refractive power measured by the objective measurement. In the examples shown in FIGS. 6 and 7, the measurement results 41 are displayed on the right side and left side of the screen, and the values on the left side show the measurement results of a right eye to be examined E, while the values on the right side show the measurement results of the left eye to be examined E.

The icons of Example 1 are an objective/subjective switching icon 42, a measurement mode selecting icon 43, a chart changing icon 44, the presentation mode switching icon 45, a results displaying icon 46, and a printing icon 47.

The objective/subjective switching icon 42 is used to switchover between the objective measurement and the subjective measurement. If the objective/subjective switching icon 42 is touched in the situation illustrated in FIG. 6 or 7, the measurement is switched from the subjective measurement to the objective measurement since FIGS. 6 and 7 show the situations where the subjective measurement is being conducted.

The measurement mode selecting icon 43 is used to select a measurement mode from a refractive mode for measuring the ocular refractive power, cornea-mode for measuring the shape of the cornea Ec, and a refractive-cornea mode for measuring the both. The measurement mode selecting icon 43 is adapted to select a measurement mode of the objective measurement. Accordingly, the icon does not have any function in the situations shown in FIGS. 6 and 7.

The chart changing icon 44 is used to change the subjective eye chart projected onto the eye to be examined E. Specifically, the chart changing icon 44 of Example 1 is used to switch between the grid chart 31v (Amsler grid chart) and the visual acuity test chart 31w. In the situations shown in FIGS. 6 and 7, the chart changing icon 44 indicates that the grid chart 31v has been selected, and the eye chart is changed from the grid chart 31v to the visual acuity test chart 31w when the chart changing icon 44 is touched.

The presentation mode switching icon 45 is used to select the mode for the subjective measurement from the instant presentation and the continuous presentation. The presentation mode switching icon 45 shown in FIG. 6 of Example 1 indicates that the continuous presentation is being conducted for the subjective measurement, and the presentation mode is switched to the instant presentation when the icon 45 is touched. On the other hand, the presentation mode switching icon 45 shown in FIG. 7 of Example 1 indicates that the instant presentation is being conducted for the subjective measurement, and the presentation mode is switched to the continuous presentation when the icon 45 is touched.

The results displaying icon 46 is used to select whether or not displaying the measurement results 41 of the objective measurement. Since the measurement results 41 are displayed in the situations shown in FIGS. 6 and 7, the measurement results 41 disappear when the icon 46 is touched.

The printing icon 47 is used to print out the whole image displayed on the screen 14*a* of the display unit 14 or the contents (measurement results) showing the measurement results 41 displayed thereon.

Additionally, a presentation start icon 48, a chart distance displaying icon 49, and a setting icon 50 are displayed on the screen 14*a* of the display unit 14, as shown in FIG. 7. The presentation start icon 48 is used to start the instant presentation of the optometric chart. That is to say, the presentation start icon 48 functions as an instant presentation starter. In the ocular refractive power measurement apparatus 10, the control unit 21 (shown in FIG. 2) does not turn on the eye chart light source 31*a* until the presentation start icon 48 is touched when conducting the subjective measurement with the instant presentation. The control unit 21 turns on the eye chart light source 31*a* when the presentation start icon 48 is touched and turns off the light source 31*a* after the instant presentation time has elapsed. Accordingly, the ocular refractive power measurement apparatus 10 can present the optometric chart to the eye to be examined E (subject) only for the instant presentation time from the moment the presentation start icon 48 is touched. The presentation start icon 48 is displayed on the screen 14*a* when the subjective measurement is conducted with the instant presentation and is not displayed on the screen 14*a* when the subjective measurement is conducted with the continuous presentation (shown in FIG. 6).

The chart distance displaying icon 49 shows a distance between the presented grid chart 31*v* and the eye to be examined E when the subjective measurement is conducted using the grid chart 31*v* (i.e., when the grid chart test is conducted). The chart distance displaying icons 49 of FIGS. 6 and 7 show that the grid chart 31*v* is presented to the eye E under a condition equivalent to the distance of 30 cm from the eye E. The chart distance displaying icon 49 is displayed on the screen 14*a* when the subjective measurement is conducted (regardless of whether the continuous presentation or instant presentation is selected).

The setting icon 50 is used to set the basic setting and or other settings of the ocular refractive power measurement apparatus 10. Hence, the setting icon 50 is always displayed on the screen 14*a*. For example, the control unit 21 (shown in FIG. 2) switches the display screen on the screen 14*a* from an initial screen, i.e., the screen displayed before the measurement mode is selected, to a screen for the basic setting when the setting icon 50 is touched. In the basic setting, the control unit 21 retrieves data of past measurement results performed on the subject (patient) and applies the results to each setting for each measurement. In a case of the subjective measurement using the optometric chart, for example, the data can be the instant presentation time, and positions where the subject sees a wavy line, braking line, or blurred line in the past subjective measurement using the grid chart 31*v* (grid chart test), (i.e., in which gazing point the subject sees such abnormalities). The data also can be the visual acuity measured in the subjective measurement using the visual acuity test chart 31*w*. Further, the control unit 21 (shown in FIG. 2) switches the display screen from a screen for conducting a measurement to a screen for changing the settings of the measurement when the setting icon 50 is touched. In the setting screen, the setting icon 50 is adapted to adjust the instant presentation time when the subjective measurement with the instant presentation using the optometric chart is conducted. As explained above, the instant presentation time of Example 1 is initially set to 0.25 second, but the examiner can increase or decrease the time to an arbitrary value. In Example 1, the lower limit value (shortest time) of the instant presentation time is, for example, 0.01 second, and the upper limit value (longest time) thereof is, for example, 2.00 seconds. Note that the lower limit value (shortest time) should be set to the minimum time in which a human being can recognize light, and thus should not be limited thereto. Further, the upper limit value (longest time) should be set to the maximum time such that it can prevent his/her brain from correcting the image representing the transmitted nerve signals, and thus should not be limited thereto. As explained above, the setting icon 50 (and the setting screen) functions as an instant presentation time setting unit for setting the instant presentation time for the instant presentation.

Further, as shown in FIGS. 6 and 7, a chart test assisting icon 51 is displayed on the screen 14*a* of the display unit 14 to assist the grid chart test. The chart test assisting icon 51 includes five check marks 51*a*-51*e* that correspond to the five gazing points (D1 to D5 (shown in FIG. 4)) of the grid chart 31*v* respectively and are displayed on an icon shaped like the grid chart 31*v* (Amsler grid chart). Specifically, the check mark 51*a* corresponds to the central gazing point D1, the check mark 51*b* to the peripheral gazing point D2, the check mark 51*c* to the peripheral gazing point D3, the check mark 51*d* to the peripheral gazing point D4, and the check mark 51*e* to the peripheral gazing point D5. Each check mark 51*a*-51*e* changes its form to easily be recognized when touched. In Example 1, the icon changes its color.

Figure 8:
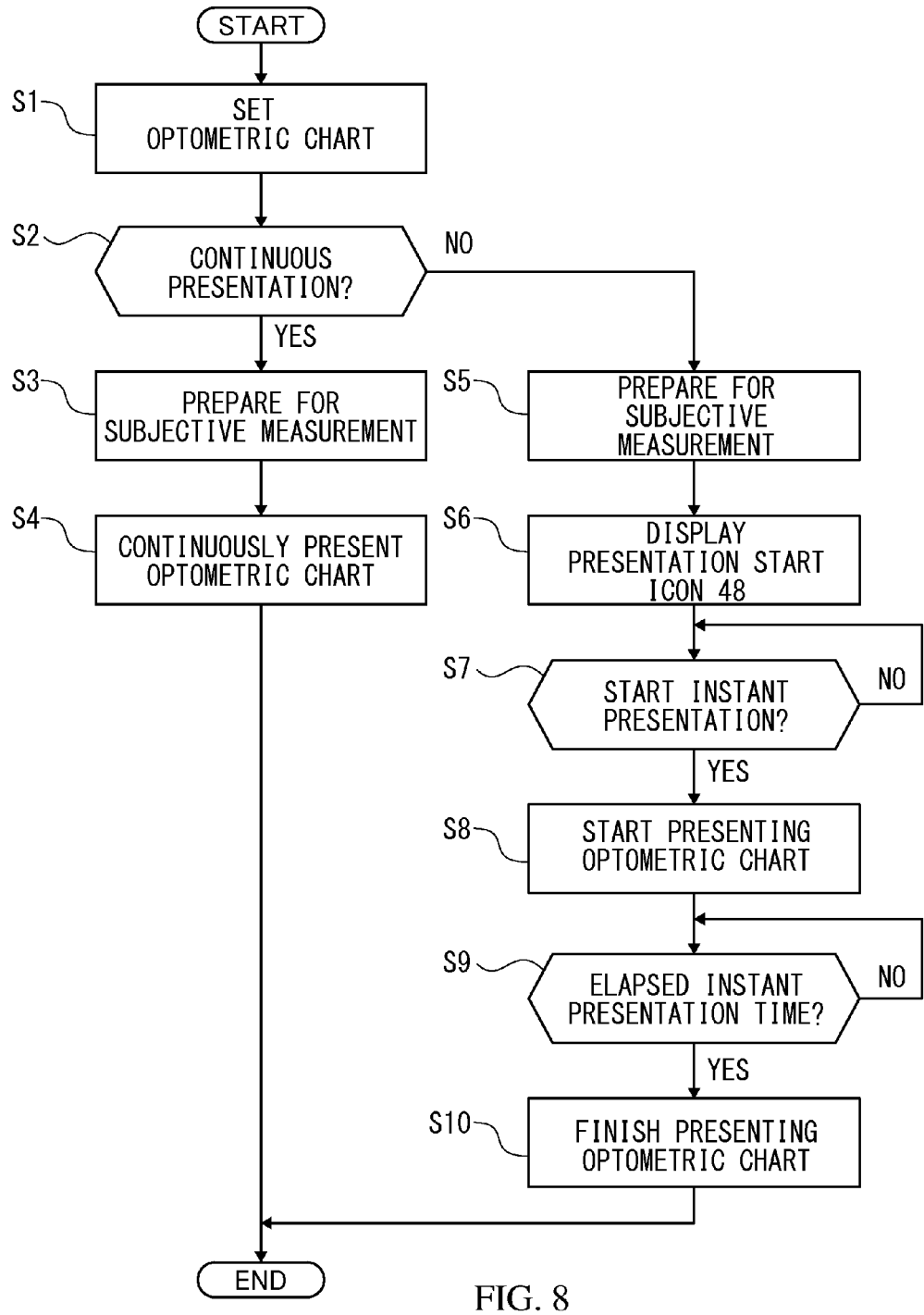
FIG. 8 is a flowchart showing a process or a method of the subjective measurement conducted by a control unit according to Example 1.

Next, process of the subjective measurement according to Example 1 of the present invention is explained with reference to FIG. 8. FIG. 8 is a flowchart showing the subjective measurement executing process (subjective measurement executing method) executed by the control unit 21 of Example 1. In accordance with program stored in the internal memory 21*a* (shown in FIG. 2) or in an external memory of the control unit 21. The subjective measurement executing process (subjective measurement executing method) is basically executed to conduct the subjective measurement with the instant presentation of the optometric chart, but is executed to conduct it with both the instant presentation and the continuous presentation in Example 1.

In the following, each step of FIG. 8 flowchart of the subjective measurement executing process (subjective measurement executing method) is explained. FIG. 8 flowchart is executed when the subjective measurement using the optometric chart is conducted. That is to say, FIG. 8 flowchart is commenced when the examiner touches the objective/subjective switching icon 42 to conduct the subjective measurement.

In Step S1, the control unit 21 sets the optometric chart to be used, and the program proceeds to Step S2. In Step S1, the control unit 21 determines the selected optometric chart and drives the change driver 31*s* of the eye chart change unit 31*d* to rotate the turret unit 31*r*, thereby positioning the selected optometric chart on the optical axis O2 of the eye chart projection optical system 31. In Example 1, the determination of which optometric chart is selected is made in response to the manipulation of the chart changing icon 44 (shown in FIGS. 6 and 7) on the display unit 14.

Following to Step S1, the control unit 21 determines whether or not the continuous presentation is selected in Step S2. When the result is YES, the program proceeds to Step S3, while the result is NO, the program proceeds to Step S5. This determination in Step S2 is made in response to the manipulation of the presentation mode switching icon 45 (shown in FIGS. 6 and 7) on the display unit 14.

Following to the determination of selecting the continuous presentation in Step S2, the control unit 21 performs a preparation for conducting the subjective measurement using the optometric chat in Step S3. The program then proceeds to Step S4. In Step S3, the control unit 21 adjusts the alignment of the main body 13 with respect to the eye to be examined E in the same manner as measuring the shape of the cornea Ec and the ocular refractive power of the eye E. Note that this alignment may be skipped if the subjective measurement using the optometric chart is conducted after measuring the shape of the cornea Ec of the eye E or the ocular refractive power since the alignment has already been adjusted. Further, if the ocular refractive power of the eye E has previously been measured, the control unit 21 controls the eye chart focusing mechanism 31D to move the focusing lens 31h along the optical axis O2 of the eye chart projection optical system 31 based on the measurement results so as to adjust the focus. With this, the control unit 21 simulatingly moves the optometric chart to a position where the ocular power of the eye E becomes appropriate to see far objects or to a position where the ocular power becomes appropriate to see near objects. Additionally, if the subjective measurement for the visual acuity test using the visual acuity test chart 31w has previously been conducted, the control unit 21 controls the eye chart focusing mechanism 31D to move the focusing lens 31h along the optical axis O2 of the eye chart projection optical system 31 based on the measurement results of the visual acuity test so as to adjust the focus.

Following to Step S3, the control unit 21 continuously presents the optometric chart selected in Step S1 to the eye to be examined E (subject) in Step S4. The program then finishes the subjective measurement executing process (subjective measurement executing method). In Step S4, the control unit 21 presents the optometric chart to the eye E (subject) until the subjective measurement using the optometric chart is finished. In Example 1, presenting the optometric chart is achieved by lighting the eye chart light source 31a of the eye chart projection optical system 31 and projecting the target light flux onto the eye E as the optometric chart positioned on the optical axis O2 so as to present (project) the optometric chart on the main optical axis O1.

Following to the determination of selecting the instant presentation in Step S2, the control unit 21 performs a preparation for conducting the subjective measurement using the optometric chat in Step S5. The process in Step S5 is identical to the preparation for the continuous presentation using the same. Hence, the control unit 21 adjusts the alignment of the main body 13 with respect to the eye to be examined E, moves the optometric chart on the optical axis O2, and adjusts the focus with respect to the optometric chart in the same manner as Step S3. Additionally, the control unit 21 turns on the direction indicating light source 31y of the eye chart projection optical system 31 to form a bright point at one of the positions corresponding to the gazing points (points D1 to D5 in FIG. 4) as the presentation position marker. For the grid chart 31v, the position to form the bright point is decided in accordance with the gazing point of the grid chart 31v (D1 to D5) which is about to be gazed (explained later). For the grid chart 31v, the check marks 51a-51e of the chart test assisting icon 51 may function to turn on/off the corresponding light sources 31y such that the examiner can select the position to form the bright point, or the position may be selected by using the setting icon 50 when setting the instant presentation.

Following to Step S5, the control unit 21 displays the presentation start icon 48 (instant presentation starter) on the screen 14a of the display unit 14 for starting the instant presentation of the optometric chart (shown in FIG. 7) in Step S6.

Following to Step S6, the control unit 21 determines whether or not starting the instant presentation of the optometric chart is commanded in Step S7. The program proceeds to Step S8 when the determination result is YES, while returns to Step S7 when the result is NO. In Example 1, the determination is made by determining whether or not the presentation start icon 48 displayed on the display unit 14 is touched by the examiner. The determination of Step S7 is repeated until the presentation start icon 48 is touched, and the program proceeds to Step S8 for starting the instant presentation when the icon 48 is touched.

Following to Step S7, the control unit 21 starts presenting the optometric chart selected in Step S1 to the eye to be examined E (subject) in Step S8. In Example 1, the presentation of the optometric chart is achieved by turning on the eye chart light source 31a of the eye chart projection optical system 31 and projecting the target light flux onto the eye E as the optometric chart on the optical axis O2 so as to present (project) the optometric chart to the eye E on the main optical axis O1. Note the direction indicating light sources 31y may be turned off to stop forming the bright point when the eye chart light source 31a is turned on. It can prevent the bright point from disturbing the recognition of the optometric chart if the light sources 31y stop forming the bright point. On the other hand, it becomes easy to recognize the optometric chart by gazing the position of the bright point if the light sources 31y are kept on. Accordingly, whether or not to keep forming the bright point should be decided in accordance with a type of the selected optometric chart and a way to recognize it.

Following to Step S8, the control unit 21 determines whether or not the instant presentation time has elapsed in Step S9. The program proceeds to Step S10 when the determination result is YES, while the program repeats the Step S9 when the determination result is NO. In Step S9, the control unit 21 determines whether or not the optometric chart has been presented for the instant presentation time by determining whether or not the instant presentation time has elapsed after the control unit 21 starts the presentation of the optometric chart in Step S8. The control unit 21 repeats the determination of Step S9 until the instant presentation time has elapsed, and the program proceeds to Step S10 when it is determined that the instant presentation time has elapsed.

Following to Step S9, the control unit 21 finishes presenting the optometric chart to the eye to be examined E (subject) and terminates the subjective measurement executing process (subjective measurement executing method). In Example 1, the control unit 21 finishes presenting the optometric chart by turning off the eye chart light source 31a of the eye chart projection optical system 31.

Next, operation of the ocular refractive power measurement apparatus 10 according to Example 1 of the present invention for conducting the subjective measurement (grid chart test) using, for example, the grid chart 31v (Amsler grid chart) will be explained. The following operation of the ocular refractive power measurement apparatus 10 is executed by the control unit 21 (shown in FIG. 2). Note that although the following operation for the subjective measurement is explained using the grid chart 31v, this is only an example. The operation is basically the same even when using the visual acuity test chart 31w.

First, the control unit 21 commences the subjective measurement executing process shown in FIG. 8 flowchart when the examiner touches the objective/subjective switching icon 42 on the display unit 14. Next, the program proceeds to Step S1 of FIG. 8 flowchart, in which the control unit 21 drives the change driver 31s of the eye chart change unit 31d to rotate the turret unit 31r, thereby positioning the grid chart 31v on the optical axis O2 of the eye chart projection optical system 31 when the examiner touches the chart changing icon 44 on the display unit 14 to select the grid chart 31v (Amsler grid chart). Next, the program proceeds to Step S2 and Step S3 of FIG. 8 flowchart, in which the control unit 21 adjusts the alignment of the main body 13 with respect to the eye to be examined E and adjusts the focus with respect to the grid chart 31v when the examiner touches the presentation mode switching icon 45 on the display unit 14 to conduct the subjective measurement with the continuous presentation of the grid chart 31v. The program then proceeds to Step S4 of FIG. 8 flowchart, in which the control unit 21 projects the target light flux onto the eye E as the grid chart 31v positioned on the optical axis O2 by turning on the eye chart light source 31a of the eye chart projection optical system 31 so as to continuously present (project) the grid chart 31v to the eye E on the main optical axis O1.

In the subjective measurement with the continuous presentation of the grid chart 31v (Amsler grid chart), i.e., in the grid chart test, the subject informs the examiner that he/she sees a wavy line, braking line, or blurred line in the latticed pattern by pressing the manipulation lever of the reaction unit 17 (shown in FIG. 2) to set the ON state when the subject sees them. Accordingly, the examiner determines that the eye E possibly has a disorder in the center (macular) of the retina (ocular fundus) Ef or a disorder around the retina when the reaction unit 17 is set to the ON state.

Further, the program proceeds from Step S2 to Step S5 and Step S6 of FIG. 8 flowchart, in which the control unit 21 adjusts the alignment of the main body 13 with respect to the eye to be examined E, adjusts the focus with respect to the grid chart 31v, presents the presentation position marker, and displays the presentation start icon 48 (instant presentation starter) on the display unit 14 (shown in FIG. 7) when the examiner touches the presentation mode switching icon 45 on the display unit 14 to conduct the subjective measurement with the instant presentation using the grid chart 31v. The program then proceeds to Step S7 and Step S8 of FIG. 8 flowchart, in which the control unit 21 turns on the eye chart light source 31a of the eye chart projection optical system 31 to project the target light flux onto the eye E as the grid chart 31v positioned on the optical axis O2 so as to start the instant presentation (projection) of the grid chart 31v to the eye E when the examiner touches the presentation start icon 48. The program then proceeds to Step S9 and Step S10 of FIG. 8 flowchart, in which the control unit 21 turns off the eye chart light source 31a of the eye chart projection optical system 31 to finish presenting the grid chart 31v (i.e., finishes the instant presentation) when it is determined that the instant presentation time has elapsed.

In the subjective measurement with the instant presentation using the grid chart 31v (Amsler grid chart), i.e., in the grid chart test, the subject informs the examiner that he/she sees a wavy line, braking line, or blurred line in the lattice pattern by pressing the manipulation lever of the reaction unit 17 (shown in FIG. 2) to set the ON state in the same manner as measuring the continuous presentation. The examiner determines that the eye to be examined E possibly has a disorder in the center (macular) of the retina (ocular fundus) Ef or a disorder around the retina when the reaction unit 17 is set to the ON state.

As explained above, the ocular refractive power measurement apparatus 10 can conduct the subjective measurement using, for example, the grid chart 31v (Amsler grid chart) i.e., grid chart test, with both the instant presentation and the continuous presentation. Here, the determination of a possibility for having a disorder in the center (macular) of the retina (ocular fundus) Ef or a disorder around the retina of the eye to be examined E should be made in the same manner for both the instant presentation and the continuous presentation. Only the difference between the instant presentation and the continuous presentation is, as explained above, whether or not excluding the influence of correcting the image representing the transmitted nerve signals in the subject's brain.

Figure 9:
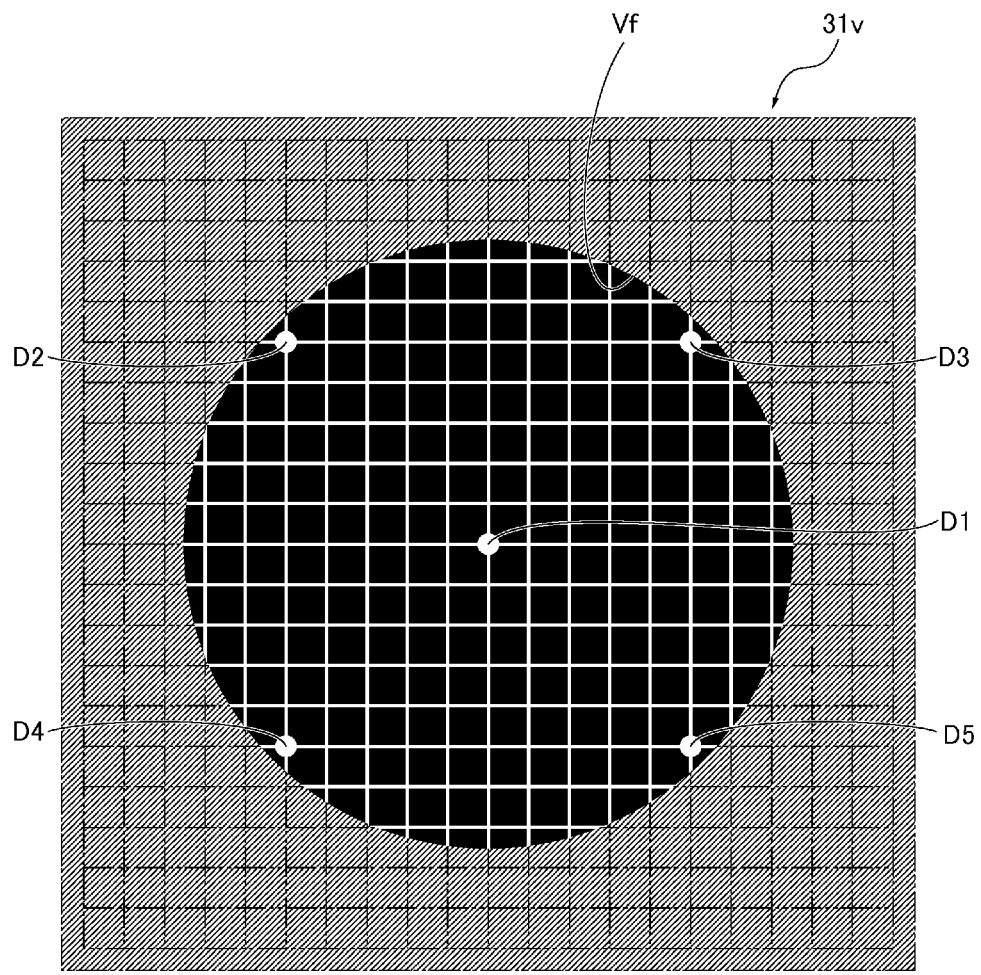
FIG. 9 is a schematic view showing a field of view of an eye to be examined on the grid chart presented by a target projection optical system.

As illustrated in FIG. 9, the ocular refractive power measurement apparatus 10 shows only the grid chart 31v of within a range of a predetermined distance from the center of the grid chart 31v regardless of the instant presentation or the continuous presentation. That is to say, the grid chart 31v (shown in FIG. 4) is presented to the eye to be examined E under the condition equivalent to the predetermined size and the distance of 30 to 40 cm (30 cm in Example 1) from the eye E in the eye chart projection optical system 31. Unavoidably, the field of view Vf of the eye E becomes limited in the eye chart projection optical system 31. Hence, it becomes difficult to show the subject the entire grid chart 31v. Therefore, the subject can see only a part of the grid chart 31v that is within the range of the predetermined distance from the center of the grid chart 31v. Note that the range of the predetermined distance from the center of the grid chart 31v (i.e., field of view Vf) corresponds to the center (macular) of the retina (ocular fundus) Ef of the eye E gazing the central gazing point D1. In an example shown in FIG. 9, the field of view Vf represents the area enclosed by the circle and indicated by the solid lines. Note that FIG. 9 schematically shows an image of how the grid chart 31v is seen through the ocular refractive power measurement apparatus 10 to assist understanding of the field of view Vf. Additionally, the grid chart 31v has a plurality of peripheral gazing points (D2 to D5) in the peripheral edge of the field of view Vf of the eye chart projection optical system 31. The eye E (subject) recognizes the outside of the field of view Vf as darkness (in FIG. 9, illustrated by hatching).

In the subjective measurement using the grid chart 31v (Amsler grid chart), i.e., in the grid chart test, it determines that the gazing eye to be examined E possibly has a disorder in the center (macular) of the retina (ocular fundus) Ef if the subject sees a wavy line, breaking line, or blurred line in the lattice pattern. In the grid chart test, a wavy line, breaking line, or blurred line are frequently found in vicinity of the center of the field of view, i.e., in the center (macular) of the retina (ocular fundus) Ef of the eye E. Therefore, it is expected that the determination of the disorder should be reliable enough even if the subject can only see the part of the grid chart 31v that is within the range of the predetermined distance from the center of the grid chart 31v (i.e., the area corresponding to the center (macular) of the retina (ocular fundus) Ef).

As explained, the ocular refractive power measurement apparatus 10 can present a part of the grid chart 31v (Amsler grid chart) corresponding to the center (macular) of the retina (ocular fundus) Ef to the eye to be examined E by using the eye chart projection optical system 31. With this, it becomes possible to determine whether or not the eye E possibly has a disorder in the center (macular) of the retina (ocular fundus) Ef by determining how the subject sees the chart as explained above when gazing the central gazing point D1 as a fixation target.

Additionally, the ocular refractive power measurement apparatus 10 according to Example 1 of the present invention is equipped with the grid chart 31*v* having four peripheral gazing points (D2 to D5) surrounding the central gazing point D1. Accordingly, the apparatus 10 uses each of the peripheral gazing point (D2 to D5) as the fixation target to determine if the subject sees a wavy line, breaking line, or blurred line in the lattice pattern in the grid chart test using the grid chart 31*v*. With this, the ocular refractive power measurement apparatus 10 determines how the subject sees areas outside the area within the range of the predetermined distance from the center of the grid chart 31*v*. As a result, the apparatus 10 can make substantially the same determination as a determination made by showing the entire grid chart 31*v* to the subject.

As explained above, the grid chart 31*v* is divided into four areas by the vertical and horizontal lines passing through the central gazing point D1 (central position), and the four peripheral gazing points (D2 to D5) are positioned at the centers of the divided areas respectively. Also, since the peripheral gazing points (D2 to D5) are positioned in the peripheral edge of the field of view Vf of the eye chart projection optical system 31, the peripheral gazing point D2 is positioned at an upper left part of the peripheral edge in the field of view Vf as shown in FIG. 10A. Accordingly, a part of the grid chart 31*v* inside the field of view Vf that is located in the lower right with respect to the peripheral gazing point D2 appears when the peripheral gazing point D2 is used as the fixation target. Based on this field of view Vf, the apparatus 10 shifts the central gazing point D1 to the position of the peripheral gazing point D2 so as to change the situation equivalent to the one having the subject gaze the central gazing point D1. In other words, the situation having the subject gaze the peripheral gazing point D2 can be considered to be equivalent to a situation shown in FIG. 10B in which the field of view Vf is shifted to the lower right of the grid chart 31*v*. Hence, the divided lower right area of the grid chart 31*v* (the hatches portion) is entirely located inside the field of view Vf. Therefore, by determining how the subject sees the grid chart 31*v* using the peripheral gazing point D2, it can consider that the apparatus 10 can determine how the subject sees the lower right area of the grid chart 31*v*. Accordingly, it can determine whether or not the eye to be examined E possibly has a disorder in the lower right area (the lower left area when the eye E is looked from the front).

Similarly, it can be considered that the apparatus 10 has determined how the subject sees the divided lower left area of the grid chart 31*v* as shown in FIG. 11B when the peripheral gazing point D3 is used as the fixation target to determine how the subject sees the grid chart 31*v* as shown in FIG. 11A. With this, it can determine whether or not the eye to be examined E possibly has a disorder in the lower left area (the lower right area when the eye E is looked from the front).

Figure 12B:
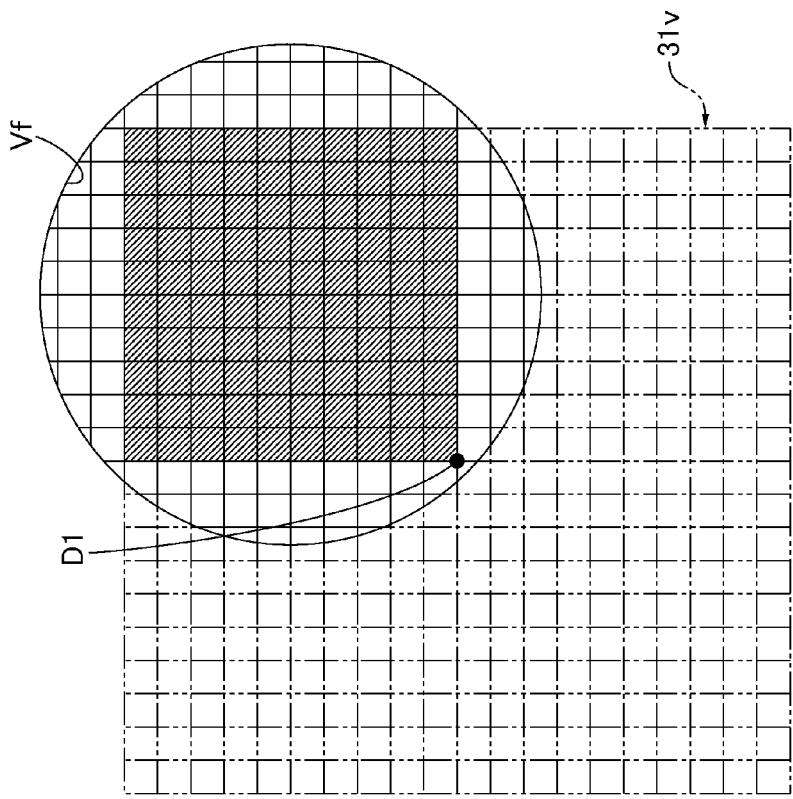
FIG. 12B is a schematic view showing a corresponding field of view of the eye when the third peripheral gazing point is replaced with the central gazing point in FIG. 12A.
Figure 12A:
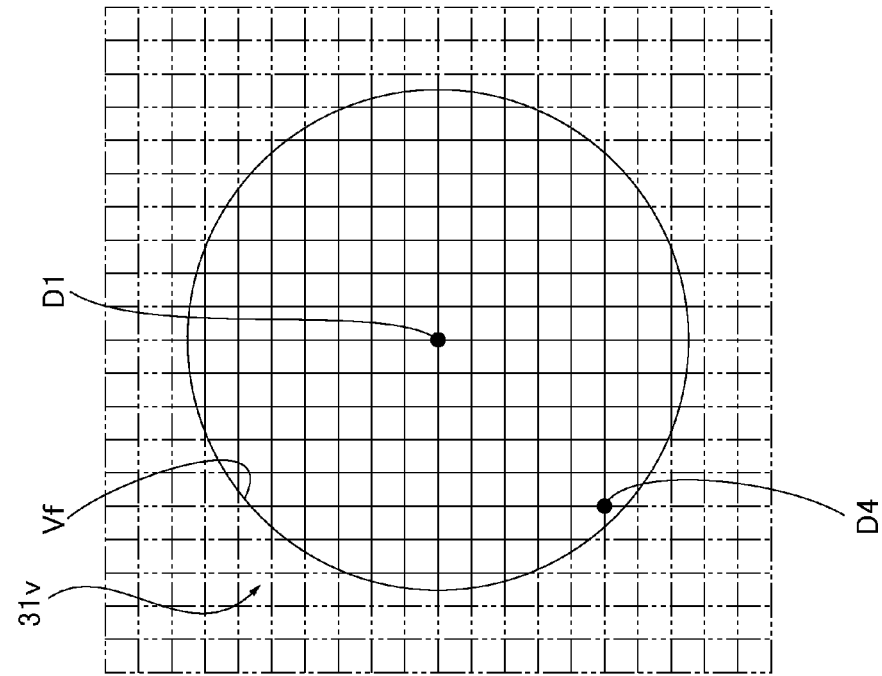
FIG. 12A is a schematic view showing a field of view of the eye when a subject gazes a third peripheral gazing point.

Similarly, it can be considered that the apparatus 10 has determined how the subject sees the upper right area of the grid chart 31*v* as shown in FIG. 12B when the peripheral gazing point D4 is used as the fixation target to determine how the subject sees the grid chart 31*v* as shown in FIG. 12A. With this, it can determine whether or not the eye to be examined E possibly has a disorder in the upper right area (the upper left area when the eye E is looked from the front).

Similarly, it can be considered that the apparatus 10 has determined how the subject sees the upper left area of the grid chart 31*v* as shown in FIG. 13B when the peripheral gazing point D5 is used as the fixation target to determine how the subject sees the grid chart 31*v* as shown in FIG. 13A. With this, it can determine whether or not the eye to be examined E possibly has a disorder in the upper left area (the upper right area when the eye E is looked from the front).

As explained above, the ocular refractive power measurement apparatus 10 uses these four peripheral gazing points (D2 to D5) as the fixation target one by one to determine how the subject sees the grid chart 31*v*. With this, it can make substantially the same determination as a determination made when showing the entire grid chart 31*v* to determine how the subject sees the entire grid chart by using the central gazing point D1. Consequently, it can determine whether or not the eye to be examined E possibly has a disorder in its entire area, and further determine at which part of the eye E possibly has the disorder. Note that the examiner selects and changes the gazing points (D1 to D5) to be gazed by the subject as the fixation target. Specifically, the examiner asks the subject to gaze one of the gazing points (D1 to D5), and the subject gazes the asked gazing point (D1 to D5) such that the selection and change of the gazing points are made. Here, the ocular refractive power measurement apparatus 10 may be equipped with a gazing point changing unit manipulated by the examiner such that the apparatus 10 can recognize which gazing point (D1 to D5) is being gazed in the subjective measurement (grid chart test) currently conducted. For the apparatus 10 configured as above, it is preferable to turn on a light source corresponding to the selected gazing point and turn off the other light sources when turning on one of the gazing points (D1 to D5) in response to the manipulation inputted to the gazing point changing unit. With this, the ocular refractive power measurement apparatus 10 can automatically determine at which gazing point (D1 to D5) the subject is gazing when he/she manipulates the reaction unit 17, i.e., when the subject detects an abnormality. As a result, it can easily determine at which part of the eye E possibly has a disorder.

In the ocular refractive power measurement apparatus 10, the examiner touches the check mark 51*a* of the chart test assisting icon 51 (shown in FIG. 6) to change its form (i.e., its color) when the subject detects an abnormality by gazing the central gazing point D1 (i.e., when the subject presses the manipulation lever of the reaction unit 17 to set the ON state as he/she saw a wavy line, breaking line, or blurred line in the latticed pattern). Similarly, the examiner touches the check mark 51*b* (shown in FIG. 6) when the subject is gazing the peripheral gazing point D2, touches the check mark 51*c* (shown in FIG. 6) when the subject is gazing the peripheral gazing point D3, touches the check mark 51*d* (shown in FIG. 6) when the subject is gazing the peripheral gazing point D4, and touches the check mark 51*e* (shown in FIG. 6) when the subject is gazing the peripheral gazing point D5 respectively. With this, the ocular refractive power measurement apparatus 10 shows at which gazing point (D1 to D5) the subject was gazing as the fixation target when he/she detected the abnormality. Therefore, the ocular refractive power measurement apparatus 10 can easily determine in which area (vicinity of the center, or other divided areas) of the grid chart 31*v* the subject detected the abnormality, thereby enabling of easy determination of at which part of the eye E possibly has a disorder.

The ocular refractive power measurement apparatus 10 can determine at which part of the eyes E possibly has a disorder by conducting the abovementioned subjective measurement (grid chart test) for both eyes.

As mentioned above, the ocular refractive power measurement apparatus 10 according to Example 1 is configured to conduct the subjective measurement by presenting the optometric chart to the eye to be examined E only for the instant presentation time. With this, the ocular refractive power measurement apparatus 10 can prevent the brain from correcting the image representing the transmitted nerve signals and recognizing the corrected image as what the subject sees. Instead, it can determine how the subject sees the optometric chart based on the real image formed on the retina (ocular fundus) Ef. Therefore, the ocular refractive power measurement apparatus 10 can properly conduct the subjective measurement in accordance with the type of the selected optometric chart.

Further, the ocular refractive power measurement apparatus 10 is configured to present (project) the optometric chart to the eye to be examined E on the main optical axis O1 of the anterior ocular segment observation optical system 32 (an optical configuration of the ocular refractive power measurement apparatus 10) by the eye chart projection optical system 31. The ocular refractive power measurement apparatus 10 then conducts the subjective measurement with the instant presentation of the optometric chart by turning on the eye chart light source 31*a* of the eye chart projection optical system 31 only for the instant presentation time. Accordingly, the ocular refractive power measurement apparatus 10 can present the optometric chart to the eye E only for the instant presentation time with a simple structure.

Furthermore, the ocular refractive power measurement apparatus 10 is configured to keep turning on the eye chart light source 31*a* of the eye chart projection optical system 31 to conduct the subjective measurement with the continuous presentation of the optometric chart. The ocular refractive power measurement apparatus 10 can switch between the instant presentation and the continuous presentation of the optometric chart by changing how to light up the eye chart light source 31*a*, i.e., whether leaving the light source 31*a* on or turning on the light source 31*a* only for the instant presentation time. In the ocular refractive power measurement apparatus 10, the instant presentation and the continuous presentation are switched by manipulating the presentation mode switching icon 45. Accordingly, the ocular refractive power measurement apparatus 10 can select the instant presentation or the continuous presentation with a simple structure and improve the usability of the apparatus 10 as it allows the user to conduct both the instant presentation and the continuous presentation freely.

The ocular refractive power measurement apparatus 10 is configured to start the instant presentation of the optometric chart to the eye to be examined E by turning on the eye chart light source 31*a* when the examiner touches the presentation start icon 48 (instant presentation starter). Specifically, the ocular refractive power measurement apparatus 10 can start the instant presentation of the optometric chart to the eye E when the examiner determines that the preparation for the subjective measurement has been completed and then manipulates the presentation start icon 48. With this, the examiner can start the instant presentation of the optometric chart using the ocular refractive power measurement apparatus 10 after informing the subject to start the presentation. As a result, it can prevent the duration time to present the optometric chart to the eye E from being less than the instant presentation time, thereby avoiding a situation in which the subject cannot recognize the optometric chart properly.

The ocular refractive power measurement apparatus 10 is configured to form the bright point at a position corresponding to one of the gazing points of the optometric chart (D1 to D5 shown in FIG. 4) as the presentation position marker to show a position for instantly presenting the optometric chart by turning on the direction indicating light sources 31*y* prior to starting the instant presentation of the optometric chart to the eye to be examined E. Accordingly, the ocular refractive power measurement apparatus 10 can fix the sight line of the eye E to the position (direction) where the optometric chart will be instantly presented by showing the bright point (presentation position marker) to the eye E (subject) even prior to presenting the optometric chart. With this, the ocular refractive power measurement apparatus 10 can further prevent the duration time to present the optometric chart to the eye E from being less than the instant presentation time, thereby avoiding a situation in which the subject cannot recognize the optometric chart properly.

In the ocular refractive power measurement apparatus 10, the subject can inform the examiner how he/she sees the optometric chart by manipulating the manipulation lever of the reaction unit 17 (shown in FIG. 2). Accordingly, in the ocular refractive power measurement apparatus 10, the subject does not have to utter a sound in the subjective measurement using the optometric chart, thereby avoiding moving the subject's face. Hence, it becomes possible to conduct the subjective measurement using the optometric chart more accurately.

The ocular refractive power measurement apparatus 10 is configured to adjust the instant presentation time to instantly present the optometric chart to the eye to be examined E by using the instant presentation time setting unit (the setting icon 50 in Example 1). Accordingly, the ocular refractive power measurement apparatus 10 can have the subject sees the optometric chart and also appropriately prevent the subject's brain from correcting the image representing the transmitted nerve signals and recognizing the corrected image as what he/she sees by setting the instant presentation time in accordance with the type of the optometric chart and/or the subject.

The ocular refractive power measurement apparatus 10 is configured to include the optometric chart (the grid chart 31*v* and the visual acuity test chart in Example 1) and other eye charts (the landscape chart 31*u* in Example 1) in the turret unit 31*r* of the eye chart change unit 31*d*, and change the eye chart positioned on the optical axis O2 by rotating the turret unit 31*r* appropriately. With this, the ocular refractive power measurement apparatus 10 can conduct the subjective measurement with the instant presentation regardless of the type of the optometric chart. Therefore, the ocular refractive power measurement apparatus 10 can instantly present several eye charts to the eye E with a simple structure and improve the usability of the apparatus 10.

The ocular refractive power measurement apparatus 10 is configured to present (project) the grid chart 31*v* (Amsler grid chart) to the eye to be examined E as the optometric chart on the main optical axis O1 of the anterior ocular segment observation optical system 32 by the eye chart projection optical system 31. Accordingly, the ocular refractive power measurement apparatus 10 can set a predetermined distance between the grid chart 31*v* and the eye E and a predetermined position of the grid chart 31*v* (Amsler grid chart). With this, the ocular refractive power measurement apparatus 10 can appropriately conduct the subjective measurement (grid chart test) to determine whether or not the eye E possibly has a disorder.

The ocular refractive power measurement apparatus 10 is configured to present (project) the grid chart 31*v* (Amsler grid chart) to the eye to be examined E on the main optical axis O1 of the anterior ocular segment observation optical system 32 by the eye chart projection optical system 31. Accordingly, the ocular refractive power measurement apparatus 10 can conduct the subjective measurement using the grid chart 31v (grid chart test) without having the subject close or cover his/her eye that is not to be examined, i.e., in the same manner as the objective measurement for measuring the ocular refractive power. With this, the ocular refractive power measurement apparatus 10 can eliminate obstacles for the subject to gaze the gazing points and conduct the subjective measurement (grid chart test) properly, thereby appropriately determining whether or not the eye possibly has a disorder.

The ocular refractive power measurement apparatus 10 is configured to present the grid chart 31v to the eye to be examined E under the condition equivalent to the predetermined size and the predetermined distance (30 cm in Example 1) from the eye E by the eye chart projection optical system 31. Accordingly, the ocular refractive power measurement apparatus 10 can present the grid chart 31v (Amsler grid chart) to the eye E under a preferred condition to conduct the subjective measurement (grid chart test) using the grid chart 31v. With this, the ocular refractive power measurement apparatus 10 can conduct the subjective measurement (grid chart test) appropriately and determine whether or not the eye E possibly has a disorder.

The ocular refractive power measurement apparatus 10 is configured to present (project) the grid chart 31v (Amsler grid chart) to the eye to be examined E under the condition equivalent to the predetermined size and the predetermined distance (30 cm in Example 1) from the eye E on the main optical axis O1 by the eye chart projection optical system 31. In conventional subjective measurement using the Amsler grid chart, the subject needs to hold or locate the Amsler grid chart, which is made of a paper, or an electronic medium, or the like, at a position where the distance from the Amsler grid chart becomes a predetermined distance. As a result, the distance from the presented Amsler grid chart and the eye E may differ due to individual differences, or the subjective measurement may be conducted in a wrong way. In contrast, the ocular refractive power measurement apparatus 10 can present the grid chart 31v (Amsler grid chart) at the predetermined distance regardless of who the subject is, and can conduct the subjective measurement using the grid chart 31v (Amsler grid chart) appropriately.

If the ocular refractive power of the eye to be examined E has previously been measured, the ocular refractive power measurement apparatus 10 is configured to adjust the focus by driving the eye chart focusing mechanism 31D to move the focusing lens 31h along the optical axis O2 of the eye chart projection optical system 31 in accordance with the measurement results of the ocular refractive power. In other words, the grid chart 31v is simulatingly moved to a position where the ocular power of the eye E becomes appropriate to see far objects or to a position where the ocular power becomes appropriate to see near objects. In the subjective measurement using the Amsler grid chart, the subject typically needs to use eyeglasses for adjusting his/her eyes in accordance with his/her visual acuity such that it becomes difficult to accurately determine how the subject sees the latticed pattern. In contrast, the ocular refractive power measurement apparatus 10 can conduct the subjective measurement after adjusting the focus as explained above. Accordingly, it can have the subject (eye E) see the grid chart 31v (Amsler grid chart) without using the eyeglasses for adjusting the his/her eyes. The ocular refractive power measurement apparatus 10 can present the grid chart 31v (Amsler grid chart) under a condition close to an optical correction value for one of the eyes E and determine how the subject sees it. Therefore, the ocular refractive power measurement apparatus 10 can determine how the subject sees the grid chart 31v under the condition in which the subject should be able to see the grid chart (Amsler grid chart) clearly. Consequently, it becomes possible to conduct the subjective measurement (grid chart test) more appropriately, thereby enabling to determine whether or not the eye E possibly has a disorder more accurately. Note that this is also applied to other optometric charts.

As explained above, since the ocular refractive power measurement apparatus 10 is configured to conduct the subjective measurement after adjusting the focus, it can have the subject see the grid chart 31v (Amsler grid chart) without using the eyeglasses for adjusting his/her eyes. If the eyeglasses for adjusting the subject's eyes are used, the measurement may be affected by distortions caused by astigmatism or distortions of the lenses of the eyeglasses. In other words, the ocular refractive power measurement apparatus 10 can eliminate this influence and conduct the subjective measurement using the grid chart 31v (Amsler grid chart). As a result, the apparatus 10 can conduct the subjective measurement (grid chart test) more appropriately and determine whether or not the eye E possibly has a disorder more accurately. Note that this is also applicable to other optometric charts.

The ocular refractive power measurement apparatus 10 is configured to present a part of the grid chart 31v (Amsler grid chart) corresponding to the center (macular) of the retina (ocular fundus) Ef to the eye to be examined E. In other words, the ocular refractive power measurement apparatus 10 can draw the subject's attention to only the part of the grid chart 31v (Amsler grid chart) corresponding to the center (macular) of the retina (ocular fundus) Ef. Therefore, the ocular refractive power measurement apparatus 10 can determine whether or not the eye E possibly has a disorder in the area corresponding to the center (macular) of the retina (ocular fundus) Ef more accurately by using the grid chart 31v (Amsler grid chart).

The ocular refractive power measurement apparatus 10 is configured to have a plurality of peripheral gazing points (four in Example 1) around the central gazing point D1, which is located in the center of the grid chart 31v. Although the ocular refractive power measurement apparatus 10 can partially present the grid chart 31v (Amsler grid chart) to the eye to be examined E (subject) by using the eye chart projection optical system 31, the ocular refractive power measurement apparatus 10 can determine whether or not the eye E possibly has a disorder in an area larger than the size of the presented grid chart 31v by having the subject gaze each peripheral gazing point as the fixation target to determine how the subject sees the chart respectively.

The ocular refractive power measurement apparatus 10 is configured to have a plurality of peripheral gazing points (four in Example 1) in the peripheral edge of the field of view Vf of the eye chart projection optical system 31. Thus, the ocular refractive power measurement apparatus 10 can determine whether or not the eye to be examined E possibly has a disorder in the entire area of the eye E by using the grid chart 31v (Amsler grid chart) that is partially shown to the eye E (subject) in his/her field of view Vf.

In the ocular refractive power measurement apparatus 10, the grid chart 31v (Amsler grid chart) is configured to be in a square shape and is divided into four areas by vertical and horizontal lines through the central gazing point D1 (central position), and the four peripheral gazing points (D2 to D5) are provided at the centers of the divided areas respectively. The ocular refractive power measurement apparatus 10 uses these four peripheral gazing points (D2 to D5) as the fixation targets to determine how the subject sees the grid chart 31v respectively. Accordingly, the ocular refractive power measurement apparatus 10 can determine whether or not the eye to be examined E possibly has a disorder in the area corresponding to the entire grid chart 31v, which is four times larger than the area defined by each of the peripheral gazing points (D2 to D5). With this, the ocular refractive power measurement apparatus 10 can conduct the subjective measurement using the grid chart 31v (Amsler grid chart) more efficiently.

The ocular refractive power measurement apparatus 10 is configured to have the plurality of peripheral gazing points (four in Example 1) in the peripheral edge of the field of view Vf of the eye chart projection optical system 31, i.e., in the peripheral edge of an area corresponding to the center (macular) of the retina (ocular fundus) Ef in the grid chart 31v (Amsler grid chart). The ocular refractive power measurement apparatus 10 uses each of the peripheral gazing points as the fixation target to be gazed when conducting the subjective measurement using the grid chart 31v (Amsler grid chart). With this, the ocular refractive power measurement apparatus 10 can determine at which part of the eye to be examined E possibly has a disorder.

Specifically, in the ocular refractive power measurement apparatus 10, it can determine whether or not the eye E possibly has a disorder in the center (macular) of the retina (ocular fundus) Ef by using the central gazing point D1, in the lower right area (in the lower left area when the eye E is looked from the front) by using the peripheral gazing point D2, in the lower left area (lower right area when the eye E is looked from the front) by using the peripheral gazing point D3, in the upper right area (upper left area when the eye E is looked from the front) by using the peripheral gazing point D4, and in the upper left area (upper right area when the eye E is looked from the front) by using the peripheral gazing point D5. Accordingly, the ocular refractive power measurement apparatus 10 can individually determine a possibility for having a disorder in each part (area) in accordance with positions and the number of the gazing points. In other words, the ocular refractive power measurement apparatus 10 can conduct the subjective measurement using the grid chart 31v (Amsler grid chart) for each part (area) of the eye E in accordance with the positions and the number of the gazing points. With this, unlike the conventional subjective measurement, it can reliably determine at which part (area) of the eye E possibly has a disorder individually.

In the ocular refractive power measurement apparatus 10, the examiner touches the corresponding check marks (51a-51e) of the chart test assisting icon 51 to change its form when the subject detects an abnormality by gazing the gazing points (D1 to D5). With this, the ocular refractive power measurement apparatus 10 can easily check in which area (i.e., in vicinity of the center or in each of the divined areas) the subject has detected the abnormality, i.e., it can easily determine at which part of the eye to be examined E possibly has a disorder.

The ocular refractive power measurement apparatus 10 is configured to present the grid chart 31v (Amsler grid chart) to the eye to be examined E by passing light (light flux) from the eye chart light source 31a through the latticed pattern. Accordingly, the ocular refractive power measurement apparatus 10 can present the grid chart 31v to the eye E with a simple structure. In particular, in Example 1, the light (light flux) passes through the lines of the lattice pattern, i.e., the lines forming the pattern are lighted by the light flux, while the other portions are dark. Further, the part outside the field of view Vf is made dark. As a result, the apparatus 10 can present the grid chart 31v (Amsler grid chart) to the eye E (subject). With this, the ocular refractive power measurement apparatus 10 can clearly show the grid chart 31v (Amsler grid chart) to the eye E (subject) such that it can conduct the subjective measurement using the grid chart 31v (Amsler grid chart) (grid chart test) more appropriately to determine whether or not the eye E possibly has a disorder.

If the subjective measurement for the visual acuity test using the visual acuity test chart 31w has previously been conducted, the ocular refractive power measurement apparatus 10 adjusts the focus by driving the eye chart focusing mechanism 31D to move the focusing lens 31h along the optical axis O2 of the eye chart projection optical system 31 in accordance with the measurement results of the visual acuity test. Accordingly, the ocular refractive power measurement apparatus 10 can conduct the subjective measurement using the grid chart 31v (Amsler grid chart) after correcting the refraction. With this, the apparatus 10 can conduct the subjective measurement more appropriately, thereby enabling to determine the possibility for having a disorder more accurately.

In addition to the ocular refractive power, the ocular refractive power measurement apparatus 10 is configured to measure the shape of the cornea Ec of the eye to be examined E. With this, it can improve the usability of the ocular refractive power measurement apparatus 10.

The ocular refractive power measurement apparatus 10 is configured to decrease the size (area) of the grid chart 31v presented to the eye to be examined E. Accordingly, the apparatus 10 can draw the subject's attention to a narrower area. With this, it can conduct the subjective measurement using the grid chart 31v (Amsler grid chart) more appropriately, thereby determining whether or not the eye E possibly has a disorder more accurately.

The ocular refractive power measurement apparatus 10 is configured to conduct the subjective measurement executing process (subjective measurement executing method (FIG. 8 flowchart)) by using the optometric chart. Accordingly, the apparatus 10 can conduct the subjective measurement by presenting the optometric chart to the eye to be examined E only for the instant presentation time. With this, it can appropriately conduct the subjective measurement in accordance with the type of the optometric chart.

In the subjective measurement executing process (subjective measurement executing method), the apparatus 10 conducts the subjective measurement by presenting the optometric chart to the eye to be examined E only for the instant presentation time. Accordingly, it can appropriately conduct the subjective measurement in accordance with the type of the optometric chart.

Consequently, the ocular refractive power measurement apparatus 10 of Example 1 according to the optometry apparatus of the present invention can conduct the subjective measurement using the optometric chart appropriately.

Figure 14:
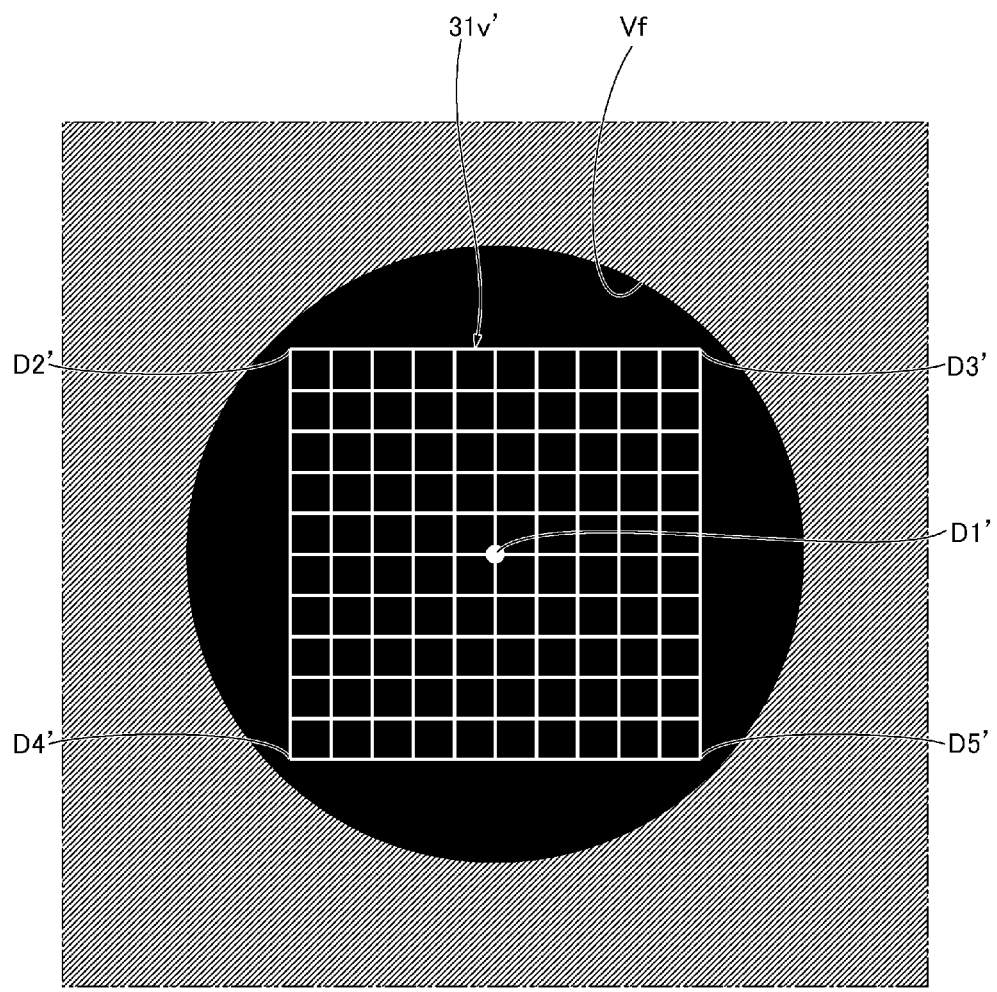
FIG. 14 is a schematic view showing another example of a field of view of the eye on the grid chart presented by the target projection optical system.

In Example 1, the grid chart 31v of the eye chart projection optical system 31 is configured to be larger than the field of view Vf of the eye to be examined E. However, as explained, the part of the grid chart 31v corresponding to the outside of the field of view Vf cannot be shown to (recognized by) the subject in the eye chart projection optical system 31. Hence, the grid chart 31v may be replaced with the grid chart 31v' (shown in FIG. 14) that can fit to inside the field of view Vf. As illustrated in FIG. 14, the grid chart 31v' is square shape, is surrounded by the four peripheral gazing points (D2 to D5) of the abovementioned grid chart 31v, and has ten boxes in each of the vertical and horizontal directions. The grid chart 31v' has a central gazing point D1' in the central position thereof but does not have peripheral gazing points. In the grid chart 31v', the four corners of the latticed pattern correspond to the peripheral gazing points (D2 to D5) of the grid chart 31v. That is to say, the four corners of the latticed pattern can represent peripheral gazing points (D2'-D5') since they can easily be used and recognized as the fixation targets in the grid chart 31v'. With this, the grid chart 31v' installed in the eye chart change unit 31d (to be specific, the turret unit 31r thereof) becomes smaller. As a result, it can decrease the size of the ocular refractive power measurement apparatus 10 with the same effects as Example 1 explained above. The ocular refractive power measurement apparatus 10 configured as explained also can determine at which gazing point (D1'-D5') is gazed by the subject during the subjective measurement (grid chart test) by using the abovementioned gazing point changing unit, which is controlled by the examiner. Note that the positions of the peripheral gazing points should not be limited as illustrated in FIG. 14. The grid chart 31v' may have peripheral gazing points (D2 to D5) in the same manner as the grid chart 31v, or may have peripheral gazing points at different positions. Further, the peripheral gazing points and the central gazing point may be formed by a plurality of light sources (e.g., LEDs), or the like as long as they can achieve the same results as the above gazing points (D1 to D5). It is, though, preferable for the gazing points to easily be used, recognized, and gazed as the fixation targets. The apparatus 10 can conduct the subjective measurement with the instant presentation using the grid chart 31v' by turning on the eye chart light source 31a of the eye chart projection optical system 31 only for the instant presentation time and can achieve the same effect.

Further, in Example 1, the apparatus 10 is equipped with the presentation start icon 48 as the instant presentation starter to perform the instant presentation of the optometric chart. However, it should not be limited thereto. For instance, a mechanical switch can be provided at the main body 13 or the display unit 14.

Further, although it is configured such that the instant presentation of the optometric chart is started when the presentation start icon 48 is touched, the configuration should not be limited thereto. For instance, the instant presentation may automatically be started when the automatic alignment with respect to the eye to be examined E is completed.

Further, it may be configured to preset a presentation-standby time and automatically start the instant presentation of the optometric chart when the presentation-standby time elapses after a prearranged manipulation has made. In this configuration, the prearrange manipulation can be a manipulation of starting the subjective measurement using the optometric chart, and the apparatus 10 starts counting the elapsed time once the manipulation is made. Accordingly, the apparatus 10 automatically starts the instant presentation when the counted elapsed time reaches to the presentation-standby time. Here, the control unit 21 may display the presentation-standby time in a count-down mode on the screen 14a of the display unit 14. With this, it becomes easy to know when the instant presentation starts, thereby improving the usability of the apparatus 10. Specifically, the examiner can know the remaining time till the instant presentation after making the manipulation for starting the subjective measurement. Hence, the examiner can explain the subject about the measurement (inspection) to be conducted and perform the preparations such as alignments for the subjective measurement using the optometric chart. Note that it is preferably configured such that the presentation-standby time is adjustable.

In Example 1, it is configured such that the instant presentation of the optometric chart is started when the presentation start icon 48 (instant presentation starter) is touched, and the instant presentation is automatically terminated when the instant presentation time has elapsed. However, it may be configured such that the optometric chart is presented to the subject while the examiner is touching (holding down) the presentation start icon 48 (instant presentation starter). In this case, the examiner can conduct the subjective measurement with the instant presentation using the optometric chart by releasing his/her finger from the presentation start icon 48 when the instant presentation time elapses after he/she starts touching the presentation start icon 48. Further, the examiner can conduct the subjective measurement with the continuous presentation by continuously touching the presentation start icon 48. Note this can be applied to the case using a switch instead of the presentation start icon 48.

In Example 1, it is configured such that the examiner can set the instant presentation time to instantly present the optometric chart in the setting screen, which appears when the setting icon 50 used as the instant presentation setting unit is touched. However, the instant presentation setting unit may be displayed on the screen 14a of the display unit 14 as one of icons used for the subjective measurement together with the other icons (icons 42-49 shown in FIG. 7), and should not be limited to the configuration of Example 1. In this case, the instant presentation time setting unit is displayed on the screen 14a of the display unit 14 as an icon when conducting the subjective measurement with the instant presentation. Accordingly, the examiner does not need to manipulate the display for opening the setting screen. As a result, the examiner can set the instant presentation time immediately by touching the icon, thereby improving the usability of the apparatus 10.

In Example 1, it is configured such that the subject presses the manipulation lever of the reaction unit 17 to set the ON state when the subject sees a wavy line, breaking line, or blurred line in the latticed pattern during the subjective measurement using the grid chart 31v. However, the subject may not be able to see the grid chart 31v itself in the subjective measurement with the instant presentation regardless of how he/she sees it. That is to say, since the grid chart 31v is presented only for the instant presentation time, the subject may not be able to see the grid chart 31v depends on his/her dynamic vision. Therefore, the reaction unit 17 may be configured to be manipulated not only when the subject sees a wavy line, breaking line, or blurred line but also when the subject cannot see the latticed pattern (i.e., grid chart 31v). This is achieved by, for example, having two manipulation levers, having two switches, or having one manipulation lever adapted to be pressed toward two directions. With this, the subject can inform the examiner that he/she detects an abnormality in his/her view while seeing the grid chart 31v or he/she simply cannot see the grid chart 31v by manipulating the reaction unit 17, thereby conducting the subjective measurement using the optometric chart more accurately. Note that this can be applied to other subjective measurements using other optometric charts such as the visual acuity test chart 31w.

In Example 1, it is configured such that the direction indicating light sources 31y form the bright points at the position corresponding to the central position of the grid chart 31v (central gazing point D1) and the positions corresponding to the four corners of the grid chart 31v (peripheral gazing points D2 to D5). However, as long as the presentation position marker can indicate a position for presenting the optometric chart to the eye to be examined E (subject), the shape, position, and form of the marker may be modified in accordance with the type of the optometric chart. For example, the marker can be a frame-shaped light that surrounds the position for presenting the optometric chart, i.e., in case of the grid chart 31v, the marker can illuminate the outer frame of the chart 31v, or the like, and therefore should not be limited to the configuration of Example 1. In this case, the light source to form the presentation position marker may be a different light source from the direction indicating light sources 31y and installed in a different optical system from the eye chart projection optical system 31. With this, the configuration for forming the presentation position marker also functions as the eye chart presentation optical system.

In Example 1, it is configured such that light (light flux) from the eye chart light source 31a passes through the eye chart of the eye chart projection optical system 31 to present the optometric chart to the eye to be examined E. However, a liquid crystal display or the like may be used, and thus it should not be limited to the configuration of Example 1.

In Example 1, it is configured such that the refractive power measurement light projection optical system 33 and the refractive power measurement light receiving optical system 34 are used to conduct the objective measurement for measuring the ocular refractive power. However, as long as the optometry apparatus can measure the optical characteristics of the eye to be examined regardless of the objective measurement or the subjective measurement and can instantly present the optometric chart, it should not be limited thereto.

EXAMPLE 2

Next, a subjective optometry apparatus 60 according to Example 2 of the present invention will be explained with reference to FIGS. 15 to 22. The subjective optometry apparatus 60 of Example 2 executes the subjective measurement method, which uses the optometric chart and is basically identical to the method executed by the ocular refractive power measurement apparatus 10 (shown in FIG. 8) of Example 1. Here, the same components and processes as Example 1 are shown by the same reference characters, and their detailed explanations will be omitted. The subjective optometry apparatus 60 can present a grid chart 31v (shown in FIGS. 4, 9, 14, and the like) as one of eye charts 65 (optometric charts) to the subject 101 (eye to be examined E).

Figure 15:
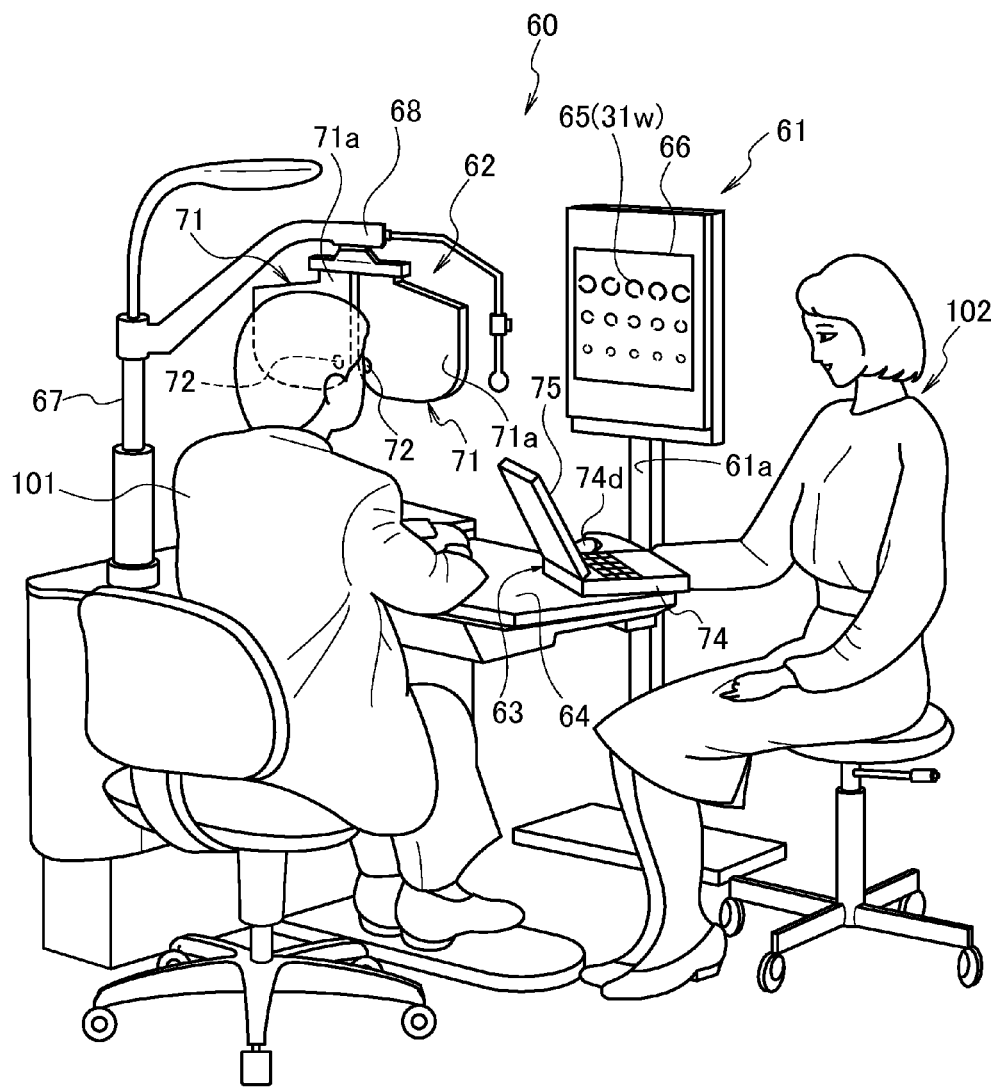
FIG. 15 is an overall view schematically showing an optometry apparatus for subjective measurement according to Example 2 of the present invention.

Also, the subjective optometry apparatus 60 of Example 2 can be used to determine a refractive power of lenses for making eyeglasses. As shown in FIG. 15, the subjective optometry apparatus 60 is equipped with an eye chart presentation unit 61, a correction unit 62, a controller 63, and an optometric table 64.

The eye chart presentation unit 61 is adapted to present the eye charts 65 to the eye to be examined of the subject 101, and the height thereof is changeable by a support pole 61a. The eye charts 65 are presented to the eye to be examined E for a visual function test, and the eye charts 65 for the subjective measurement are basically identical to the optometric chart used for the ocular refractive power measurement apparatus 10 of Example 1. FIG. 15 shows an example in which the visual acuity test chart 31w is presented to the subject 101. The eye chart presentation unit 61 includes a display board 66 to display the eye charts 65. On the display board 66, images including the eye charts 65 are displayed by the calculation control circuit 76 (shown in FIG. 18) as explained later (shown in FIGS. 19 and 20), and the types of the eye charts 65 displayed thereon can be selected using the controller 63. The eye chart presentation unit 61 (the display board 66) is controlled by the calculation control circuit 76 to present each of the eye charts 65 only for the instant presentation time or continuously. Accordingly, the eye chart presentation unit 61 (the display board 66) can present the eye charts 65 to the eye E of the subject 101 instantly and continuously.

The optometric table 64 is disposed between the eye chart presentation unit 61 and the subject 101. The controller 63 is put on the optometric table 64. The optometric table 64 has a support pole 67 that is extendable vertically and a support arm 68 that is rotatable around the support pole 67. The support arm 68 is horizontally extended from the top of the support pole 67 and has the correction unit 62 at a horizontal part of the arm 68.

Figure 21:
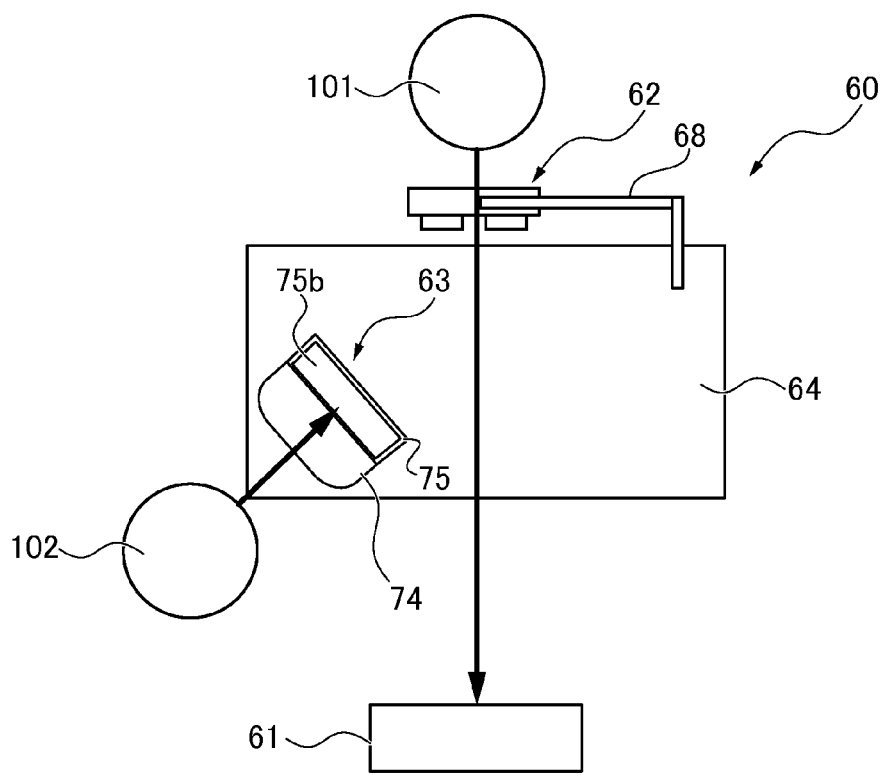
FIG. 21 is a schematic view showing a situation in far-sight examination using the subjective optometry apparatus according to Example 2.

The correction unit 62 is provided to correct a visual function of the eye to be examined E of the subject 101 and is positioned between the subject 101 (eye to be examined) and the eye chart presentation unit 61 by the support pole 67 and the support arm 68 (shown in FIG. 21 and the like). The correction unit 62 includes a symmetric phoropter 71. The phoropter 71 has a housing 71a to accommodate optical members to correct the visual function of the eye E, and the housing 71a has optometric windows 72. The optometric windows 72 are provided corresponding to the eyes E of the subject 101 such that the subject 101 can see the eye chart presentation unit 61 (to be specific, the display board 66 thereof) through the windows 72 via the optical members accommodated in the phoropter 71. The right and left sides of the phoropter 71 are configured such that the relative distance is adjustable, i.e., the phoropter 71 can be moved closer to each other or can be moved away from each other. Accordingly, the correction unit 62 can adjust the interoptical axis distance between the optometric windows 72 to the pupillary distance of the both eyes E of the subject 101.

Figure 16:
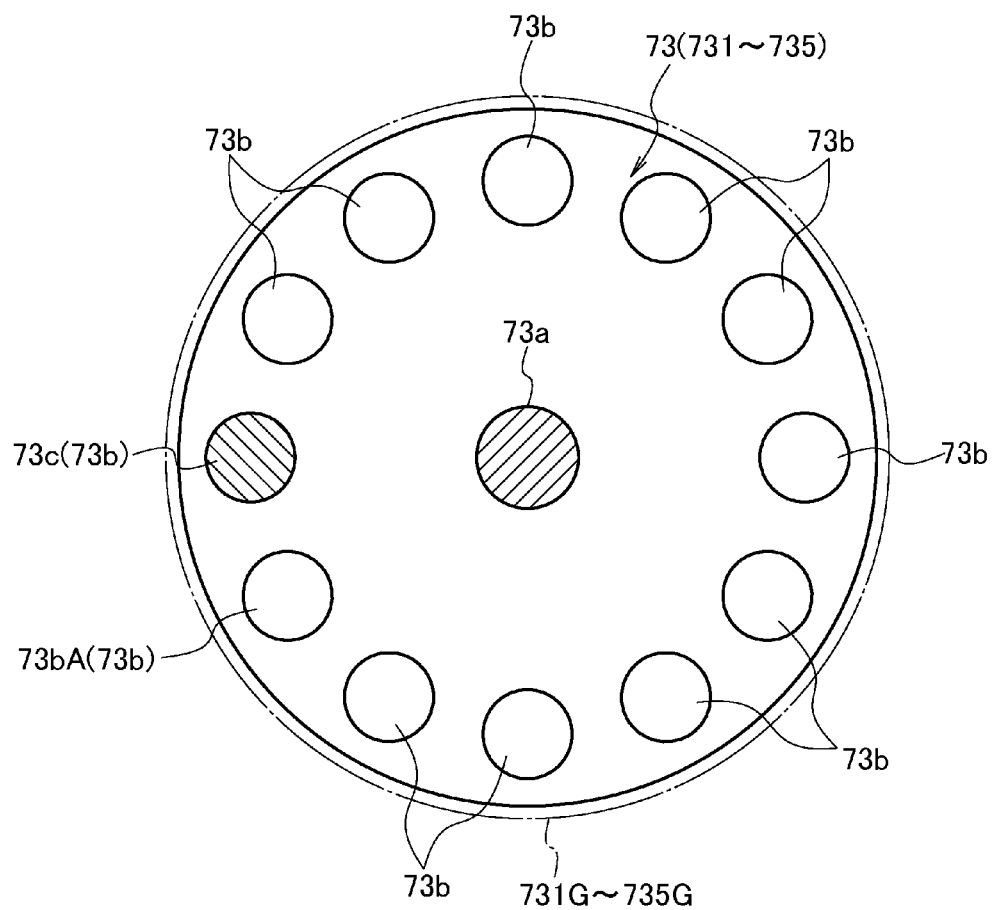
FIG. 16 is an explanatory view for explaining an arrangement of rotary discs installed in a phoropter of the subjective optometry apparatus according to Example 2.

The phoropter 71 has five rotary discs 73 (referred by 731 to 735 when mentioned individually (shown in FIG. 16)) which are rotatably provided around a rotary shaft 73a. As illustrated in FIG. 16, each rotary disc 73 has circular openings 73b disposed at regular intervals in the circumferential direction. Further, the outer peripheral edge of each rotary disc (731 to 735) forms a gear (731G to 735G). Each of the gears 731G to 735G is meshed with a driving gear (not shown) rotated by a pulse motor controlled by the calculation control circuit 76 (shown in FIG. 18) explained later. Each of the rotary discs 73 combines the corrective lenses installed in the circular openings 73b appropriately and disposes the combined lenses at the optometric windows 72.

On the rotary disc 731, spherical lenses (not shown) with spherical powers different from each other by, for example, 0.25 diopter are respectively provided to the circular openings 73b as optical elements for examination (inspection). Further, on the rotary disc 732, spherical lenses (not shown) with spherical powers different from each other by 3.00 diopters are respectively provided to the circular openings 73b. Further, on the rotary disc 733, cylindrical lenses (not shown) are respectively provided to the circular openings 73b as optical elements for inspection. Further, on the rotary disc 734, horizontal prisms for inspecting horizontal phoria, vertical prisms for inspecting vertical phoria, and inspection prisms for inspecting horizontal phoria with correction values different from each other are provided to the circular openings 73b. The horizontal prisms are used to split the presented eye chart in the horizontal direction, and the vertical prisms are used to split the presented eye chart in the vertical direction. On the rotary disc 735, inspection prisms (optical members, to be specific, inspection vertical prisms) for inspecting vertical phoria with correction values different from each other, Maddox rod lenses for inspecting phoria by Maddox rod test, and the like are provided to the circular openings 73*b*.

Additionally, a plain-glass lens is provided to at least one of the circular openings 73*b* on each of the rotary discs 73 for conducting the measurement without applying any correction to the eye to be examined E. On each of the rotary discs of Example 2, the circular opening 73*b* with a reference character 73*b*A has the plain-glass lens. Further, the circular opening 73*b* of each rotary disc 73 located next to the circular opening 73*b*A is installed with an occluder 73*c* for blocking the eye E of the subject 101 from seeing the eye charts 65.

The correction unit 62 is controlled by the calculation control circuit 76 (shown in FIG. 18) of the phoropter 71 to rotate the rotary discs 73 by driving the pulse motor so as to set the corrective lenses selected by the examiner to the optometric windows 72. With this, the correction unit 62 can adjust the power of the correction at the optometric windows 72. The calculation control circuit 76 adjusts the power of the correction by the correction unit 62 based on manipulations inputted to the controller 63.

Figure 17:
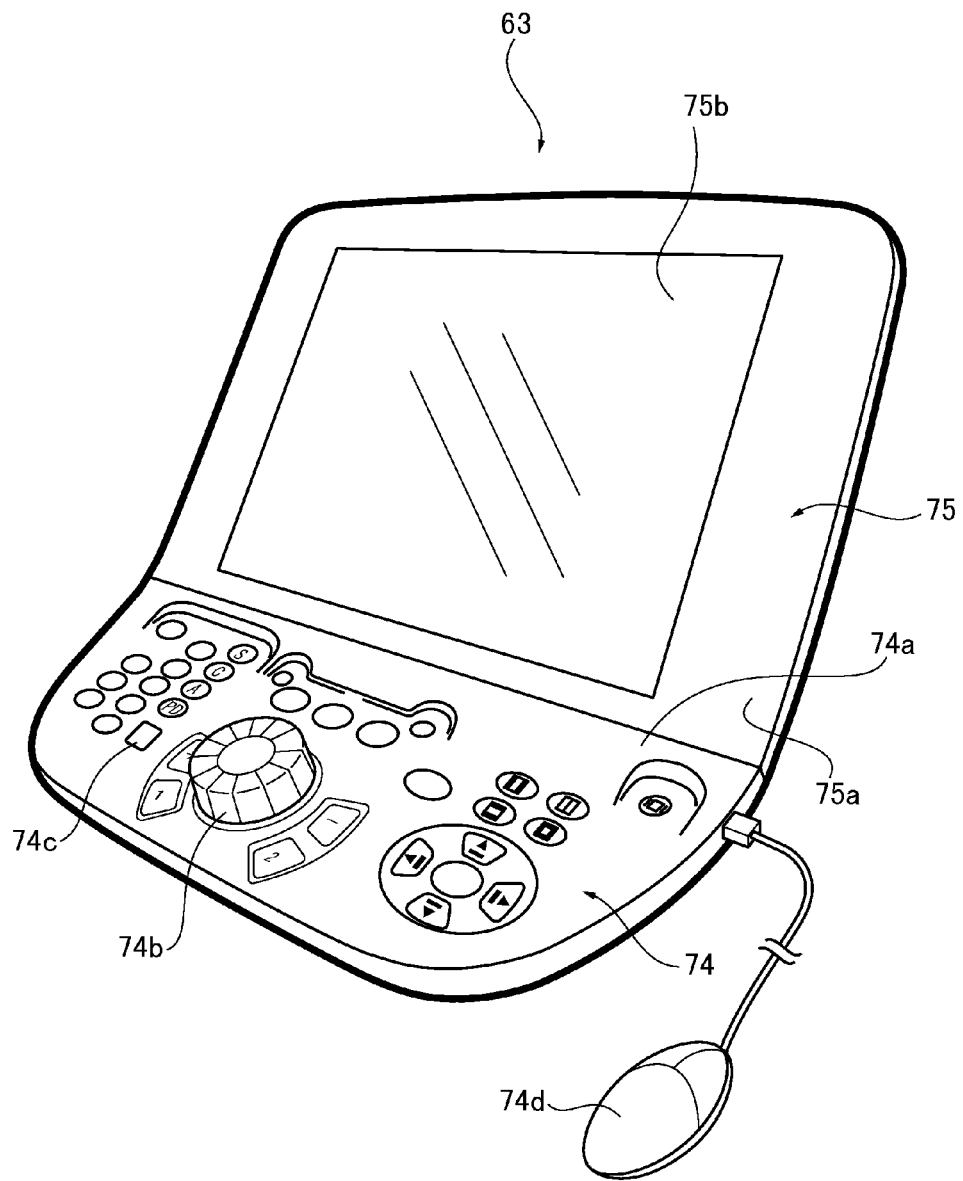
FIG. 17 is a schematic view showing a structure of a controller of the subjective optometry apparatus according to Example 2.

As shown in FIG. 17, the controller 63 has a manipulation section 74 manipulated by the examiner 102 (shown in FIG. 15) and a display section 75 to display a manipulation image showing inputted manipulation. An end portion 74*a* of the manipulation section 74 and a lower end portion 75*a* of the display section 75 are rotatably attached to each other via a shaft.

The manipulation section 74 has various switches, such as a dial 74*b*, display change switch 74*c*, and the like, for use in setting or execution of the examination. The dial 74*b* is adapted to select a corrective lens to be set to the optometric window 72. The display change switch 74*c* is adapted to switch an image displayed on the display section 75 between a first display mode for conducting a far-sight examination (shown in FIG. 19) and a second display mode for conducting a near-sight examination (shown in FIG. 20). A mouse 74*d* is connected to the manipulation section 74 for use in setting or execution of the examination in the same manner as the other switches.

The display section 75 has a screen 75*b* to display the manipulation inputted through the manipulation section 74, the eye charts 65, data of the examination, and the like. The first display mode (shown in FIG. 19) and the second display mode (shown in FIG. 20) are alternatively displayed on the screen 75*b*. The screen 75*b* of Example 2 is designed to be a touch panel screen, and the examiner can touch icons to execute below-mentioned manipulations in the first display mode and in the second display mode.

Figure 18:
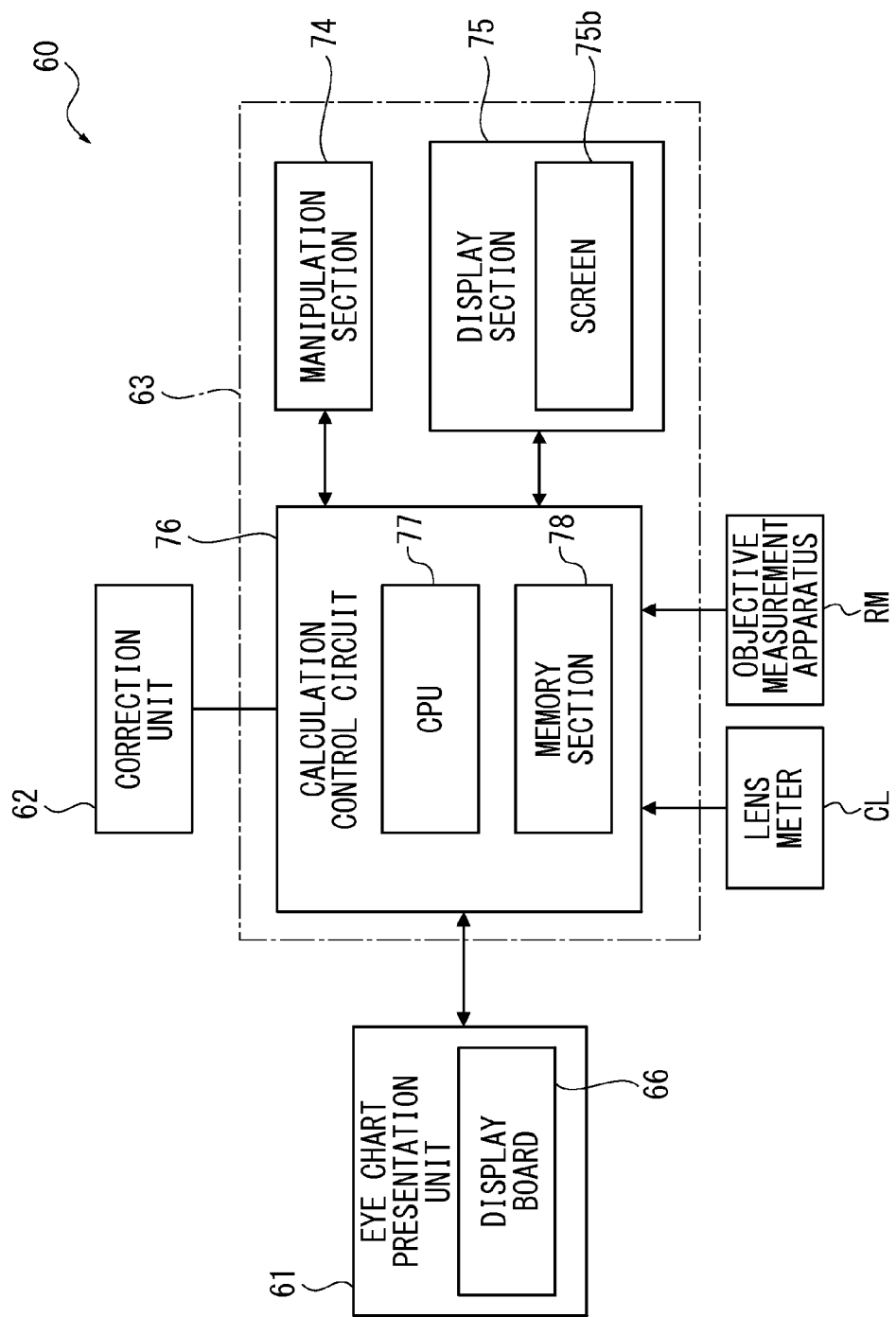
FIG. 18 is a block diagram of the subjective optometry apparatus according to Example 2.

In addition to the manipulation section 74 and the display section 75, the controller 63 has the calculation control circuit 76 as shown in FIG. 18. The calculation control circuit 76 is equipped with a CPU 77 and a memory section 78. The CPU 77 integrally controls the subjective optometry apparatus 60 in accordance with a program pre-installed into the memory section 78. The CPU 77 (the subjective optometry apparatus 60) is connected to the manipulation section 74 and the display section 75 and controls the operation (display) of the display section 75 (the screen 75*b* thereof) in response to a manipulation inputted to the manipulation section 74. The CPU 77 (subjective optometry apparatus 60) is further connected with a driving control unit of the eye chart presentation unit 61 and a driving control unit (specifically, the pulse motor thereof) of the correction unit 62 and controls the operations of the eye chart presentation unit 61 and correction unit 62. The CPU 77 (subjective optometry apparatus 60) is also connected to a lens meter CL and an objective measurement apparatus RM, i.e., other optical examination devices such that it can retrieve measurement data from the other optical examination. The measurement data include optical characteristics of the eye to be examined, optical characteristics of lenses of the eyeglasses, and data related to the examination such as an ID of the device, ID of the subject, name of the subject, data number, measurement time, and the like.

The memory section 78 stores the eye charts 65 used for the far-sight examination the eye charts 65 used for the near-sight examination and eye charts data of each. The CPU 77 displays the eye charts 65 on the eye chart presentation unit 61 (on the display board 66 thereof) and/or on the display section 75 (specifically, in an eye chart presentation window 91 on the screen 75*b* thereof) based on the stored eye chart images. Additionally, the memory section 78 stores manipulation image data representing the manipulation images (including the first display mode and the second display mode). The memory section 78 also stores lens data DL of the corrective lenses (shown in FIGS. 19 and 20), which include the spherical power, cylindrical power, cylinder axis angle, and refractive power such as prism diopters in the horizontal direction and in the vertical direction.

When the dial 74*b* of the manipulation section 74 is manipulated by the examiner, the CPU 77 retrieves the lens data DL of the refractive power corresponding to a position of the dial 74*b*. The CPU 77 then sends a control signal to the driving control unit (pulse motor thereof) of the correction unit 62 and sets the corrective lens having the refractive power of the retrieved lens data DL to the optometric window 72. Accordingly, the corrective lenses having the selected refractive power are set to the phoropter 71 of the correction unit 62 by manipulating the dial 74*b*. Further, the CPU 77 sends the signal representing the lens data DL retrieved from the memory section 78 to the display section 75 and displays the lens data DL on the screen 75*b* (see FIGS. 19 and 20).

When the display change switch 74*c* is manipulated to switch the display mode between the first display mode and the second display mode, the CPU 77 retrieves manipulation image data corresponding to the selected display mode from the memory section 78. The CPU 77 then sends a signal representing the retrieved manipulation image data to the display section 75 and displays the manipulation image corresponding to the display mode on the screen 75*b*.

Figure 19:
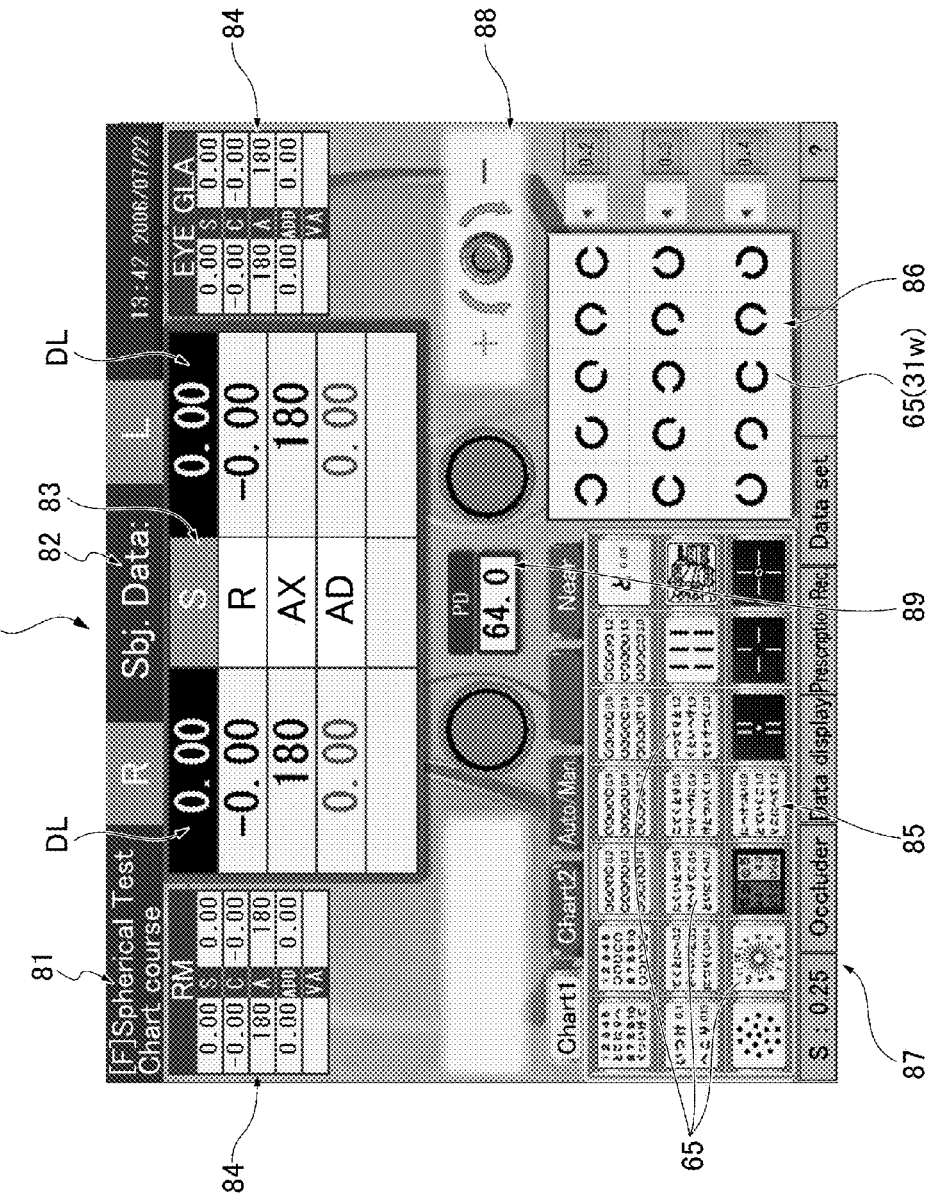
FIG. 19 is an explanatory view for explaining contents displayed on a screen of a display section in a first display mode of the subjective optometry apparatus according to Example 2.

The first display mode is displayed to conduct the far-sight examination for measuring the eye function when the eye to be examined E is seeing a far object. Specifically, the first display mode is displayed on the display section 75 (on the screen 75*b* thereof) to measure the eye function when the eye E is seeing the eye chart 65 displayed on the eye chart presentation unit 61 (on the display board 66 thereof) through the correction unit 62. As shown in FIG. 19, an examination type display field 81, an examination contents display field 82, a refractive power window 83, reference windows 84, an eye charts list window 85, an eye chart window 86, a manipulation icons display field 87, a dial display field 88, and a pupillary distance window 89 are displayed on the screen 75*b* of the display section 75 in the first display mode. These fields and windows are respectively stored in the memory section 78 as the image data. Further, the fields and windows also function as icons of the touch panel of the screen 75*b* (display section 75) such that the examiner can touch them for the manipulations. Accordingly, the CPU 77 (calculation control circuit 76) receives a detection signal, which is generated when the icon on the screen 75b is touched, from the display section 75, retrieves data corresponding to the detection signal from the memory section 78, and then sends the signals representing the retrieved data to the display section 75 and the eye chart presentation unit 61.

The examination type display field 81 displays the name of the currently conducted examination. In the example illustrated in FIG. 19, it shows that the spherical power test in the far-sight examination using a chart (eye chart) is being conducted. The examination contents display field 82 displays the name of the contents of the examination. In the example illustrated in FIG. 19, it displays "R" representing the right eye on the left end of the field and "L" representing the left eye on the right end thereof. Further, the center of the field shows that the data (measurement results) of the far-sight examination with the subjective measurement are being acquired. The refractive power window 83 displays the lens data DL of the corrective lens set by the correction unit 62 (the phoropter 71 thereof), specifically, it displays the optical characteristics data of the optical element set to the optometric windows 72, i.e., the spherical power, cylindrical power, cylinder axis angle, and the like of the corrective lens. As explained above, the corrective lens is selected and set in accordance with the manipulation on the dial 74b of the manipulation section 74. That is to say, the refractive power window 83 displays the manipulation results of the dial 74b. Accordingly, the CPU 77 (calculation control circuit 76) controls the correction unit 62 such that the optical elements corresponding to the optical characteristics data, which are to be displayed on the refractive power window 83, are set to the optometric windows 72. In the example illustrated in FIG. 19, the refractive power window 83 displays the spherical power, cylindrical power, cylinder axis angle, and additional power (ADD) of the corrective lens as the lens data DL and respectively displays the values of these optical characteristics data set to the optometric windows 72 for the left eye and right eye of the subject 101.

The reference windows 84 display the optical characteristics data which are comparable to the optical characteristics data displayed on the refractive power window 83, and are used to improve efficiency of the subjective measurement conducted by the examiner 102. The reference windows 84 are displayed on the right and left sides of the refractive power window 83 respectively, and each of them displays the optical characteristics data for the right eye or the left eye of the subject 101. In the example illustrated in FIG. 19, the reference window 84 on the left side displays measurement data retrieved from the objective measurement apparatus RM (shown in FIG. 18), specifically, it displays letters "RM" representing the title of the measurement data in the uppermost column and values of the measurement data in the lower columns. Also, in the example illustrated in FIG. 19, the reference window 84 on the right side displays the measurement data retrieved from the lens meter CL (shown in FIG. 18), specifically, it displays letters "CL" representing the title of the measurement data in the uppermost column and values of the measurement data in the lower columns.

The eye charts list window 85 displays a list of the eye charts 65 available for the subjective optometry apparatus 60, specifically, it displays selection tabs at the upper portion for selecting the list to be displayed and the eye charts 65 of the selected list below the selection tabs. In the example illustrated in FIG. 19, the selection tabs comprise, in order from the left, "Chart 1" and "Chart 2" tabs for displaying lists of the all eye charts 65, "Auto/Man." tab for displaying a list of the eye charts 65 used for automatic manipulations and manual manipulations, a blank tab having nothing, and "Near" tab for displaying a list of the eye charts 65 used for the near-sight examination. In the example illustrated in FIG. 19, the "Chart 1" tab, which is on the leftmost side, is selected and the list of the eye charts 65 in the "Chart 1" is displayed below the tabs. In the eye charts list window 85, the examiner can select the eye chart 65 by touching one of the eye charts 65 in the displayed list. The eye chart window 86 displays the eye chart 65 selected in the eye charts list window 85. In the example illustrated in FIG. 19, it displays the selected visual acuity test chart 31w. The CPU 77 (calculation control circuit 76) controls the eye chart presentation unit 61 to display the eye chart 65, which is selected in the eye charts list window 85 and displayed in the eye chart window 86, on the display board 66 (see FIG. 15).

The manipulation icons display field 87 displays icons for the various manipulations at the bottom of the screen 75b. In the example illustrated in FIG. 19, the manipulation icons display field 87 comprises, in order from the left, "S:0.25" icon as a stepwise button for changing the lens power by 0.25 diopter, "Occluder" icon for setting the occluder to the optometric window 72, "Data display" icon for displaying the various data, "Prescription:Rec." icon for recording a prescription data, and "Data set" icon for setting data such as subjective data, objective data, most recent prescription data, previous prescription data, naked-eye data, and the like. The dial display field 88 displays a dial image showing the condition of the dial 74b (shown in FIG. 17) of the manipulation section 74. The pupillary distance window 89 displays the optical axis distance between the right and left optometric windows 72 (shown in FIG. 15) which represents the pupillary distance between the right and left eyes to be examined of the subject 101.

Figure 20:
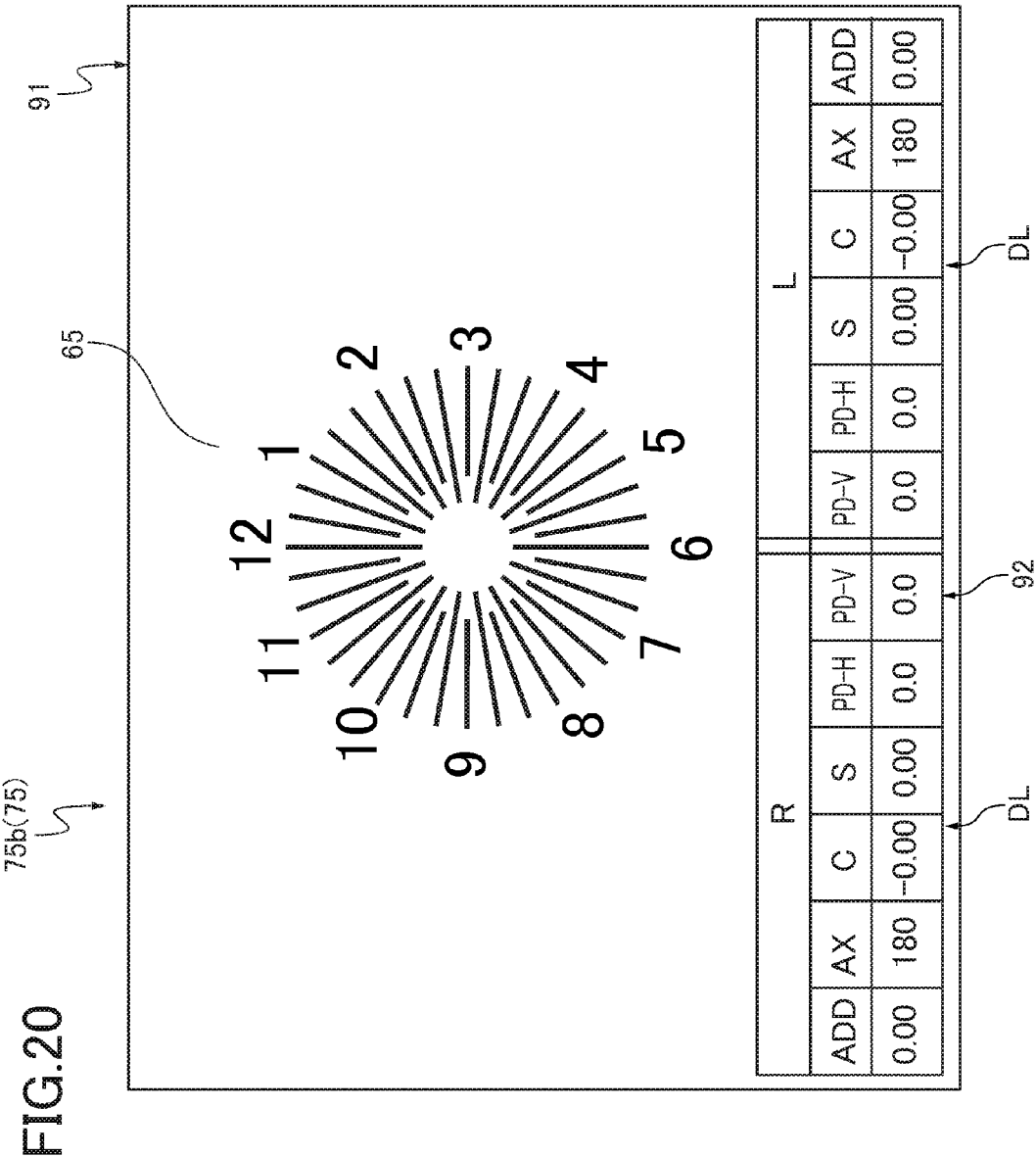
FIG. 20 is an explanatory view for explaining contents displayed on the screen of the display section in a second display mode of the subjective optometry apparatus according to Example 2.

The second display mode is displayed to conduct the near-sight examination for measuring the eye function when the eye to be examined E is seeing a near object. Specifically, the second display mode is displayed on the screen 75b of the display section 75 to examine the eye function when the eye E is seeing the eye chart 65 displayed on the screen 75b through the correction unit 62. As shown in FIG. 20, the eye chart presentation window 91 for presenting the eye chart 65 and a refractive power display field 92 for displaying the lens data DL of the corrective lens set in the correction unit 62 (phoropter 71 thereof) are displayed on the screen 75b of the display section 75 in the second display mode. The window 91 and field 92 are respectively stored in the memory section 78 (shown in FIG. 18) as the image data. The eye chart presentation window 91 displays the eye chart 65 to be seen by the subject 101 (eye to be examined E) in the near-sight examination.

The refractive power display field 92 displays the lens data DL of the corrective lenses set to the right and left sides of the phoropter 71 on the right and left sides on the field. Specifically, the refractive power display field 92 displays the letter "R" or "L" representing the right eye or left eye in the uppermost column, parameters of the lens data in the columns below the uppermost column, and the corresponding data in the lowermost columns. In the example illustrated in FIG. 20, the refractive power display field 92 displays, in order from the outside, the additional power (letter "ADD"), cylinder axis angle (letter "AX"), cylindrical power (letter "C"), spherical power (letter "S"), prism diopter in the horizontal direction (letter "PD-H"), and prism diopter in the vertical direction (letter "PD-V").

Further, the second display mode is controlled by the CPU 77 (calculation control circuit 76) to display each of the eye charts 65 on the eye chart presentation window 91 only for the instant presentation time or continuously. Accordingly, the display section 75 (the screen 75b thereof) can instantly or continuously present each of the eye charts 65 to the eye to be examined E of the subject 101.

As explained above, the CPU 77 (calculation control circuit 76) can execute the continuous presentation and instant presentation of the eye charts 65 (optometric charts) on the eye chart presentation unit 61 (display board 66 thereof) and on the display section 75 (the eye chart presentation window 91 on the screen 75b) of the controller 63. Since the eye chart presentation unit 61 (display board 66 thereof) and the display section 75 (screen 75b) are configured with a display device such as a display, it is easy to present the eye charts 65 (optometric charts). Further, the CPU 77 (calculation control circuit 76) is configured such that the examiner can select the continuous presentation and the instant presentation of the eye charts 65 (optometric charts). The selection of the continuous presentation or the instant presentation is achieved by displaying an icon corresponding to the presentation mode switching icon 45 (shown in FIGS. 6 and 7) of Example 1 on the display section 75 (screen 75b thereof) in the first display mode or the second display mode. Or, the selection of the continuous presentation and the instant presentation may be achieved by providing a switch, for example, in the controller 63, or by any other structures.

Furthermore, the CPU 77 (calculation control circuit 76) displays an icon corresponding to the presentation start icon 48 (shown in FIGS. 6 and 7) as an instant presentation starter, which is used for starting the instant presentation of the eye chart 65 (optometric chart) by using an eye chart presentation optical system (the eye chart presentation unit 61, the display section 75 of the controller 63) on the display section 75 (screen 75b thereof) in the first display mode or the second display mode when conducting the subjective measurement with the instant presentation. Accordingly, the subjective optometry apparatus 60 can start the instant presentation of the selected eye chart 65 (optometric chart) in the same manner as the ocular refractive power measurement apparatus 10 of Example 1. Note that instead of displaying the icon corresponding to the presentation start icon 48, the instant presentation starter may be achieved by providing a switch, for example, in the controller 63, or by any other structures.

Further, the CPU 77 (calculation control circuit 76) displays a presentation position marker for indicating a position to present the eye chart 65 (optometric chart) in the eye chart presentation window 91 on the display board 66 or on the screen 75b by using the eye chart presentation optical system (the eye chart presentation unit 61, the display section 75 of the controller 63) when conducting the subjective measurement with the instant presentation. The CPU 77 (calculation control circuit 76) forms bright points (central gazing point D1 and peripheral gazing points D2 to D5 (shown in FIG. 4)) as the presentation position markers on the eye chart presentation unit 61 (display board 66) or on the display section 75 (the eye chart presentation window of the screen 75b) of the controller 63 in the same manner as the ocular refractive power measurement apparatus 10 of Example 1. Note the presentation position marker should not be limited to that of Example 2. Specifically, as long as the presentation position marker can show the eye to be examined E (subject 101) the position to present the eye chart 65 (optometric chart), the shape, position, and form of the marker may be modified in accordance with the type of the optometric chart.

Additionally, the CPU 77 (calculation control circuit 76) displays an icon corresponding to the setting icon 50 (and the setting screen) of Example 1 as an instant presentation time setting unit, which is used for adjusting the instant presentation time for the subjective measurement, on the screen 75b of the display section 75 in the first display mode or the second display mode. With this, the subjective optometry apparatus 60 can adjust the instant presentation time to present the selected eye chart 65 (optometric chart) instantly in the same manner as the ocular refractive power measurement apparatus 10 of Example 1. Note that instead of displaying the icon corresponding to the setting icon 50 (and the setting screen), the instant presentation time may be adjusted by providing a switch in, for example, the controller 63, or by any other structures.

Further, the subjective optometry apparatus 60 is equipped with a reaction unit similar to the reaction unit 17 of Example 1 such that the subject 101 can input his/her reaction with respect to the subjective measurement. Accordingly, in the subjective optometry apparatus 60, the subject 101 does not have to give the examiner his/her reaction against the selected eye chart 65 (optometric chart) by oral, but can give it by using the reaction unit in the same manner as Example 1. Note that the reaction unit should not be limited to that of Example 2. For example, the reaction unit may be a mouse 74d, or the like.

Next, the far-sight examination and the near-sight examination will be explained. First, the examiner 102 manipulates the display change switch 74c (shown in FIG. 17) provided at the manipulation section 74 to change the image of the display section 75 (screen 75b thereof) into the first display mode for conducting the far-sight examination. The CPU 77 (calculation control circuit 76) then controls the subjective optometry apparatus 60 to display the manipulation image of the first display mode (shown in FIG. 19) on the screen 75b of the display section 75. The examiner 102 then selects one of the eye charts 65 of the far-sight examination from the eye charts list window 85 in the manipulation image of the first display mode. The CPU 77 (calculation control circuit 76) then controls the subjective optometry apparatus 60 to display the selected eye chart 65 on the eye chart window 86 of the display section 75 (shown in FIG. 19) and on the display board 66 of the eye chart presentation unit 61 (shown in FIG. 15). Accordingly, the examiner 102 can see the eye chart 65 displayed on the eye chart window 86 to confirm whether the eye chart 65 displayed on the display board 66 and on the eye chart window 86 are identical to the selected eye chart 65.

Under this condition, the subjective optometry apparatus 60 has the subject 101 see the eye chart 65 displayed on the display board 66 of the eye chart presentation unit 61 through the optometric windows 72 of the phoropter 71 (correction unit 62), as shown in FIG. 21. Here, the above setting may be carried out after having the subject 101 (eye to be examined E) see the optometric windows 72. Accordingly, the eye chart presentation unit 61 together with the correction unit 62 functions as the eye chart presentation optical system to present an optometric chart to the eye E as the subjective eye chart, which is gazed by the eye E for the subjective measurement. Further, the examiner 102 asks the subject 101 how he/she sees the eye chart 65 and changes the corrective lenses to be set to the phoropter 71 (optometric windows 72 thereof) by manipulating the dial 74b of the manipulation section 74. Simultaneously, the lens data DL of the corrective lenses selected by the manipulation of the dial 74b is displayed on the refractive power window 83 of the display section 75. Accordingly, the examiner 102 can manipulate the dial 74b as seeing the displayed lens data DL. This operation is repeated until the subject 101 can see the eye chart 65 clearly such that the examiner 102 can determine the refractive power of the eyeglasses to be made to properly correct the eye function of the eye.

Figure 22:
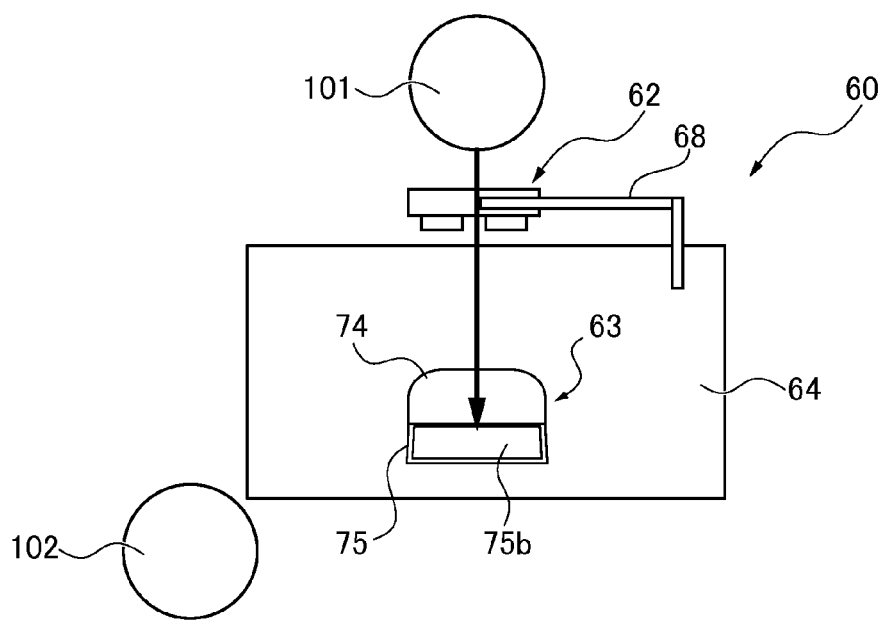
FIG. 22 is a schematic view showing a situation in near-sight examination using the subjective optometry apparatus according to Example 2.

As shown in FIG. 22, the examiner 102 puts the controller 63 in front of the subject 101 on the optometric table 64 such that the screen 75b of the display section 75 is faced to the phoropter 71 when the examination to measure the eye function in the near-sight is conducted. The examiner 102 then selects one of the eye charts 65 of the near-sight examination from the eye charts list window 85 and manipulates the display change switch 74c (shown in FIG. 17) provided at the manipulation section 74 to change the image on the screen 75b of the display section 75 into the second display mode. The CPU 77 (calculation control circuit 76) then controls the subjective optometry apparatus 60 to display the manipulation image of the second display mode (shown in FIG. 20) on the screen 75b of the display section 75. Further, the CPU 77 (calculation control circuit 76) controls the subjective optometry apparatus 60 to display the selected eye chart 65 in the eye chart presentation window 91 on the screen 75b of the display section 75 (shown in FIG. 20). Simultaneously, the CPU 77 (calculation control circuit 76) calculates a distance between the phoropter 71 and the screen 75b and adjusts the size of the eye chart 65 to be displayed on the screen 75b in accordance with the calculated distance and the visual acuity of the subject 101 (eye to be examined E).

Under this condition, the examiner 102 has the subject 101 see the eye chart 65 displayed on the screen 75b of the display section 75 of the controller 63 through the optometric windows 72 of the phoropter 71 (correction unit 62). Accordingly, the display section 75 of the controller 63 together with the correction unit 62 functions as the eye chart presentation optical system to present an optometric chart to the eye E as the subjective eye chart. Further, the examiner 102 asks the subject 101 how he/she sees the eye chart 65 and changes the corrective lenses to be set to the phoropter 71 (optometric windows 72 thereof) by manipulating the dial 74b of the manipulation section 74 in the same manner as the far-sight examination. This operation is repeated until the subject 101 can see the eye chart 65 clearly such that the examiner 102 can determine the refractive power of the eyeglasses to be made to properly correct the eye function of the eye to be examined E.

Further, the subjective optometry apparatus 60 can measure the phoria of the eye to be examined E by using a polarizing plate, a red/green filter, and/or a liquid crystal filter. Note measurements using them are conducted in the same manner as the conventional techniques.

Additionally, the CPU 77 (calculation control circuit 76) controls the subjective optometry apparatus 60 to present the eye chart 65 on the display board 66 of the eye chart presentation unit 61 only for the instant presentation time when conducting the far-sight examination. In this embodiment, the eye chart 65 is presented on the display board 66 of the eye chart presentation unit 61 for the instant presentation, i.e., compared to Example 1, only the place for presenting the eye chart 65 is changed to the eye chart presentation unit 61 (the display board 66 thereof) from the screen 14a of the display unit 14. Hence, the CPU 77 can execute the instant presentation in the same manner as Example 1 (Steps S7 to S10 in FIG. 8 flowchart). Further, the CPU 77 (calculation control circuit 76) controls the subjective optometry apparatus 60 to present the eye chart 65 in the eye chart presentation window 91 on the screen 75b of the display section 75 only for the instant presentation time when conducting the near-sight examination. In this embodiment, the eye chart 65 is presented on the screen 75b (eye chart presentation window 91), i.e., compared to Example 1, only the place for presenting the eye chart 65 is changed to the screen 75b of the display section 75 (eye chart presentation window 91) from the screen 14a of the display unit 14. Hence, the CPU 77 can execute the instant presentation in the same manner as Example 1 (Steps S7 to S10 in FIG. 8 flowchart). Accordingly, the CPU 77 (calculation control circuit 76) functions as a control unit to control the presentation of the optometric chart (eye chart 65) in the eye chart presentation optical system (the eye chart presentation unit 61, the display section 75 of the controller 63).

The subjective optometry apparatus 60 of Example 2 essentially has the same configuration as the ocular refractive power measurement apparatus 10 of Example 1. Therefore, it is basically possible to achieve the same effects as Example 1.

Additionally, the CPU 77 (calculation control circuit 76) controls the subjective optometry apparatus 60 to present the eye chart 65 instantly on the display board 66 of the eye chart presentation unit 61 or in the eye chart presentation window 91 of the display section 75 (screen 75b thereof). With this, the subjective optometry apparatus 60 can conduct the subjective measurement with the instant presentation using the eye charts 65 as the optometric charts for both the far-sight examination and the near-sight examination with a simple structure.

Consequently, the subjective optometry apparatus 60 of Example 2 can appropriately conduct the subjective measurement using the optometric chart.

Although the images displayed on the screen 75b in the first display mode and the second display mode are illustrated in FIGS. 19 and 20, they are only examples. So long as the first display mode displays an image for the far-sight examination and the second display mode displays an image for the near-sight examination, they should not be limited thereto.

Although the ocular refractive power measurement apparatus 10 and the subjective optometry apparatus 60 are described as examples of the optometry apparatus according to the present invention, they should not be limited thereto. Specifically, any optometry apparatus including an eye chart presentation optical system that presents an optometric chart to an eye to be examined and a control unit that controls the eye chart presentation optical system to present the optometric chart, wherein the control unit executes instant presentation of the optometric chart by controlling the eye chart presentation optical system to finish presenting the optometric chart when an instant presentation time has elapsed after the eye chart presentation optical system starts presenting the optometric chart can be applied to the present invention.

Further, although the apparatus according to each of the abovementioned embodiments is configured to execute both the instant presentation and the continuous presentation, it should not be limited thereto. Specifically, any apparatus that can present the optometric chart only for the instant presentation time can be applied to the present invention.

Besides, the apparatuses according to the abovementioned embodiments are configured such that the grid chart 31v is divided into four areas by the vertical and horizontal lines passing through the central gazing point D1 (central position), and the four gazing points (D2 to D5) are provided in the centers of the divided four areas respectively. However, these are only examples, and should not be limited thereto. The positions and the number of the gazing points can be modified. Any apparatus that can determine whether or not the eye to be examined E possibly has a disorder in an area larger than an area corresponding to the part of the grid chart 31v (Amsler grid chart) presented to the eye E can be applied to the present invention.

In the abovementioned embodiments, the gazing points (D1 to D5) are provided at the grid chart 31v in advance. However, they should not be limited thereto. For example, the apparatus may be configured to have a plurality of light sources (e.g., LEDs) in the eye chart projection optical system 31 at positions corresponding to the gazing points (D1 to D5), to form the gazing points by the corners of the grid chart (latticed pattern), or the like. Here, it is preferable that the gazing points are easily used for guiding the eye to be examined E by the examiner, and easily understood and gazed by the subject as the fixation target. When the gazing points (D1 to D5) are formed by the plurality of the light sources, the apparatus is configured such that the examiner touches the check mark (51a-51e (shown in FIG. 6)) of the chart test assisting icon 51 to turn on the corresponding light source and turn off the other light sources. With this, it becomes possible to switch the gazing points (D1 to D5) used as the fixation target by touching the check marks.

In the abovementioned embodiments, the grid chart 31v presented to the eye to be examined E is configured such that the lines of the latticed pattern are lighted in white color. However, so long as the grid chart 31v is presented to the eye E, the color of the lines of the latticed pattern may be changed to red, green, or blue color. This may be achieved for the ocular refractive power measurement apparatus 10 by having a plurality of color correction filters for various colors as the color correction filter 31b in the eye chart projection optical system 31 and providing one of the filters on the optical axis O2. Alternatively, it can be achieved by using a light source that can emit various colors of light (light fluxes) in place of the eye chart light source 31a. The light source that can emit the various colors of light may be achieved by having a plurality of light sources and changing the light sources appropriately. Specifically, it can emit light (light flux) of a number of colors if it includes a red light source, a green light source, and a blue light source. Further, it may be achieved for the subjective optometry apparatus 60 by providing a liquid crystal display capable of color display at the eye chart presentation unit 61 (display board 66) and the display section 75 (screen 75b). In such a case, the apparatus 60 can present the grid chart 31v (Amsler grid chart) to the eye E (subject) in various colors. Therefore, it becomes possible to determine whether or not the eye E possibly has a disorder even if the eye E has different reactions against colors (different feelings of how he/she sees the grid chart 31v). In other words, by presenting the grid chart 31v (Amsler grid chart) to the eye E (subject) in various colors, it can also determine a difference of the reactions against colors (different feelings of how he/she sees the grid chart 31v). Further, it becomes possible to determine how the subject sees the grid chart 31v (Amsler grid chart) more accurately by presenting the grid chart 31v (Amsler grid chart) in the color of the highest visibility so as to determine whether or not the eye E possibly has a disorder more accurately. Note that this can be applied to other optometric charts including the visual acuity test chart 31w.

In the abovementioned embodiments, the grid chart 31v (Amsler grid chart) is configured to have twenty boxes in each of the vertical and horizontal directions. However, it should not be limited thereto. Any grid chart with a latticed pattern capable of being used for the objective measurement (grid chart test (Amsler grid chart test)) can be applied. For instance, the size, the number of boxes, or the shape can be modified appropriately.

In the abovementioned embodiments, the subjective measurement method is exemplarily executed by the ocular refractive power measurement apparatus 10 and the subjective optometry apparatus 60. However, they should not be limited thereto. Specifically, any subjective measurement method measuring ocular characteristics of an eye to be examined of a subject by presenting an optometric chart to the eye and determining how the subject sees the presented optometric chart, the method including a step for starting presentation of the optometric chart, a step for determining whether or not an instant presentation time elapses after the presentation starts, and a step for finishing the presentation of the optometric chart when it is determined that the instant presentation time has elapsed can be applied to the present invention. For example, it may present an optometric chart (eye chart) illustrated on a paper to the eye E (subject) only for the instant presentation time, or it may present the optometric chart (eye chart) displayed on a tablet-computer to the eye E (subject) only for the instant presentation time.

Although the optometry apparatus and method for subjective measurement using the optometric chart according to the present invention has been described in terms of exemplary embodiments, it is not limited thereto. It should be appreciated that variations may be made in the embodiments described by persons skilled in the art without departing from the scope of the present invention as defined by the following claims.

What is claimed is:

1. An optometry apparatus comprising:
   an eye chart presentation optical system that presents an optometric chart to an eye to be examined; and
   a control unit that is configured to control the eye chart presentation optical system and to select a continuous presentation mode or an instantaneous presentation mode, the continuous presentation mode presenting the optometric chart to the eye continuously, and the instantaneous presentation mode presenting the optometric chart for an instantaneous presentation time only,
   wherein the control unit controls the eye chart presentation optical system in the instantaneous presentation mode to present a presentation position marker for showing a position for presenting the optometric chart and then to execute the instantaneous presentation of the optometric chart by starting presenting the optometric chart at the position shown by the presentation position marker and by finishing presenting the optometric chart when the instantaneous presentation time has elapsed after the eye chart presentation optical system starts presenting the optometric chart.

2. The apparatus as claimed in claim 1, wherein the instantaneous presentation time is set to prevent a brain from correcting an image representing nerve signals transmitted to the brain.

3. The apparatus as claimed in claim 1, further including an instantaneous presentation starter that starts the instantaneous presentation of the optometric chart by the eye chart presentation optical system, wherein the control unit starts the instantaneous presentation of the optometric chart at the position shown by the presentation position marker when the instantaneous presentation starter is manipulated while the presentation position marker is presented.

4. The apparatus as claimed in claim 1, further including a reaction unit that is manipulated to input a reaction against the optometric chart presented by the eye chart presentation optical system.

5. The apparatus as claimed in claim 1, further including an instantaneous presentation time setting unit that sets the instantaneous presentation time.

6. The apparatus as claimed in claim 1, wherein the optometric chart is an Amsler grid chart having a latticed pattern.

7. The apparatus as claimed in claim 1, further including a refractive power measurement light projection optical system that projects measurement light onto ocular fundus of the eye; and a refractive power measurement light receiving optical system that receives light reflected by the ocular fundus,
   wherein the control unit measures ocular refractive power of the eye based on the received light at the refractive power measurement light receiving optical system,
   wherein the eye chart presentation optical system presents the optometric chart to the eye.

8. The apparatus as claimed in claim 7, further including an ocular characteristics measurement light projection optical system that projects another measurement light onto the eye for measuring ocular characteristics other than the ocular refractive power; and an ocular characteristics measurement light receiving optical system that receives the another measurement light that is reflected at the eye.

9. The apparatus as claimed in claim 3, wherein the control unit starts the instantaneous presentation when the instantaneous presentation starter is manipulated and finishes the instantaneous presentation when the manipulation of the instantaneous presentation starter is stopped.

10. The apparatus as claimed in claim 4, wherein the reaction unit is configured to be manipulated to input a reaction when a subject is not able to see the optometric chart.

11. The apparatus as claimed in claim 1, further comprising a display,
    wherein the display displays a check mark that represents the position for presenting the optometric chart, and
    a form of the check mark is changed when a subject detects an abnormality in a view of the optometric chart.

12. The apparatus as claimed in claim 1,
    wherein the eye chart presentation optical system further comprises an eye chart light source and a direction indicating light source,
    wherein the eye chart light source is configured to emit light to present the optometric chart ,
    wherein the direction indicating light source is configured to emit light to present the position marker.

13. A subjective measurement method for measuring ocular characteristics of an eye to be examined of a subject by presenting an optometric chart to the eye and determining how the subject sees the presented optometric chart, the method comprising:
    selecting an operating mode from a continuous presentation mode in which the optometric chart is presented to the eye continuously, and an instantaneous presentation mode in which the optometric chart is presented for an instantaneous presentation time only;
    when the instantaneous presentation mode is selected, presenting a presentation position marker, for showing a position for presenting the optometric chart in the instantaneous presentation mode,
    starting presentation of the optometric chart at the position shown by the presentation position marker,
    determining whether or not the instantaneous presentation time has elapsed elapses after the presentation starts, and
    finishing the presentation of the optometric chart when it is determined that the instantaneous presentation time has elapsed.

* * * * *